United States Patent
Collins et al.

(10) Patent No.: US 12,054,705 B2
(45) Date of Patent: Aug. 6, 2024

(54) COMPOSITIONS AND METHODS FOR ORDERED AND CONTINUOUS COMPLEMENTARY DNA (cDNA) SYNTHESIS ACROSS NON-CONTINUOUS TEMPLATES

(71) Applicant: The Regents of the University of California, Oakland, CA (US)

(72) Inventors: Kathleen Collins, Berkeley, CA (US); Heather E. Upton, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 856 days.

(21) Appl. No.: 17/167,136

(22) Filed: Feb. 4, 2021

(65) Prior Publication Data
US 2021/0261944 A1 Aug. 26, 2021

Related U.S. Application Data

(63) Continuation of application No. PCT/US2019/045817, filed on Aug. 8, 2019.

(60) Provisional application No. 62/716,159, filed on Aug. 8, 2018.

(51) Int. Cl.
C12N 15/10 (2006.01)
C07K 14/435 (2006.01)
C12N 9/12 (2006.01)

(52) U.S. Cl.
CPC ........ *C12N 15/10* (2013.01); *C07K 14/43563* (2013.01); *C12N 9/1276* (2013.01); *C12N 2310/344* (2013.01); *C12N 2310/345* (2013.01); *C12N 2310/3517* (2013.01)

(58) Field of Classification Search
None
See application file for complete search history.

(56) References Cited

U.S. PATENT DOCUMENTS

2019/0071711 A1* 3/2019 Bibillo ............... C12N 15/1096

OTHER PUBLICATIONS

Yang ("Identification of the endonuclease domain encoded by R2 and other site-specific, non-long terminal repeat retrotransposable elements", PNAS, 1999, vol. 96, 7847-7852). (Year: 1999).*

* cited by examiner

*Primary Examiner* — Robert J Yamasaki
*Assistant Examiner* — Charles Zoltan Constantine
(74) *Attorney, Agent, or Firm* — Richard Aron Osman

(57) ABSTRACT

The invention provides compositions and methods for nucleic acid synthesis, including ordered and continuous complementary DNA (cDNA) synthesis across non-continuous templates using a modified eukaryotic non-long terminal repeat reverse transcriptase (non-LTR RT) protein.

12 Claims, 16 Drawing Sheets
Specification includes a Sequence Listing.

FIG. 1A
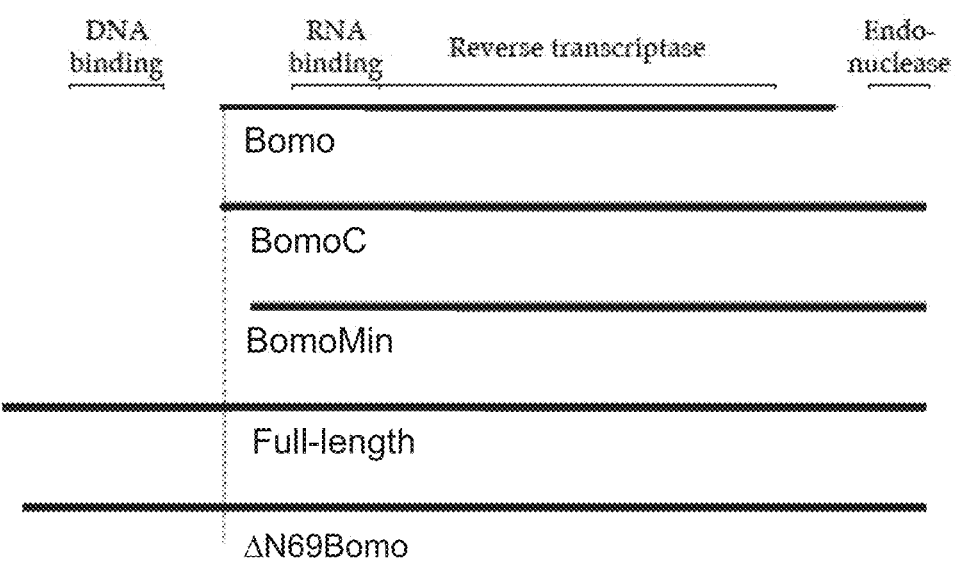
FIG. 1B
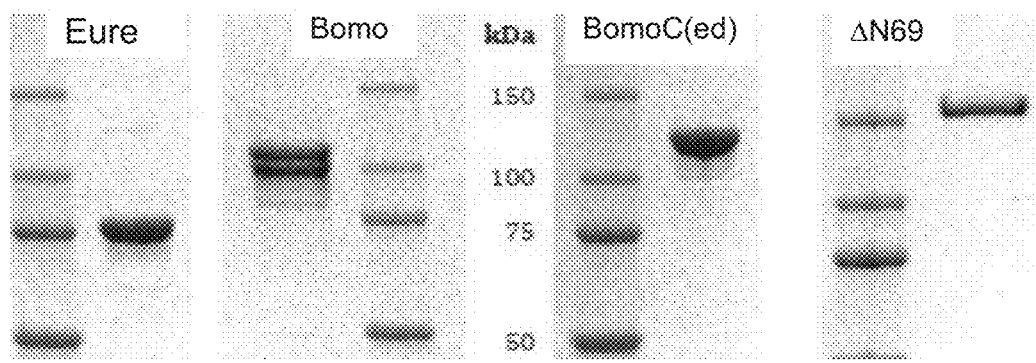
FIG. 1C
| Project | Sample | Void Ratio (260/280) | Monomer Peak Ratio (260/280) | Total protein yield (mg) |
|---|---|---|---|---|
| 1040 | ΔN69Bomo | 0.9 | 0.4 | 1.65 (*) / 5L |
| | BomoC(ed) | 0.9 | 0.5 | 40 / 2L |
| | Eure | nd | 0.5 | 14 / 2L |
| p911 | BomoC(ed) | nd | 0.5 | 34 / 2L |
| | Eure | 0.6 | 0.5 | 14 / 2L |
| p851 | Bomo | 0.8 | 0.5 | 2.2 / 2L |

FIG. 14A
FIG. 14B
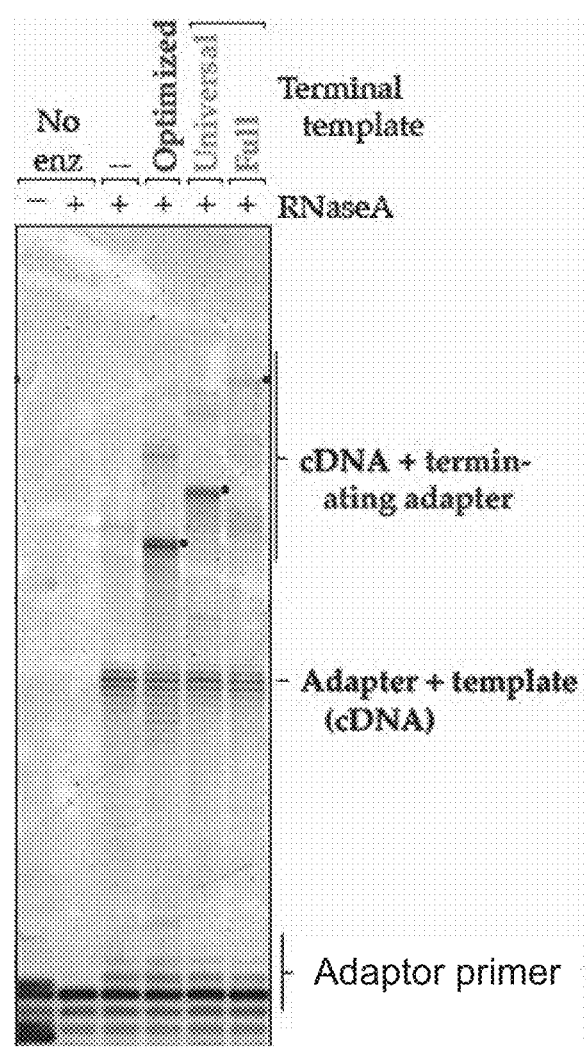
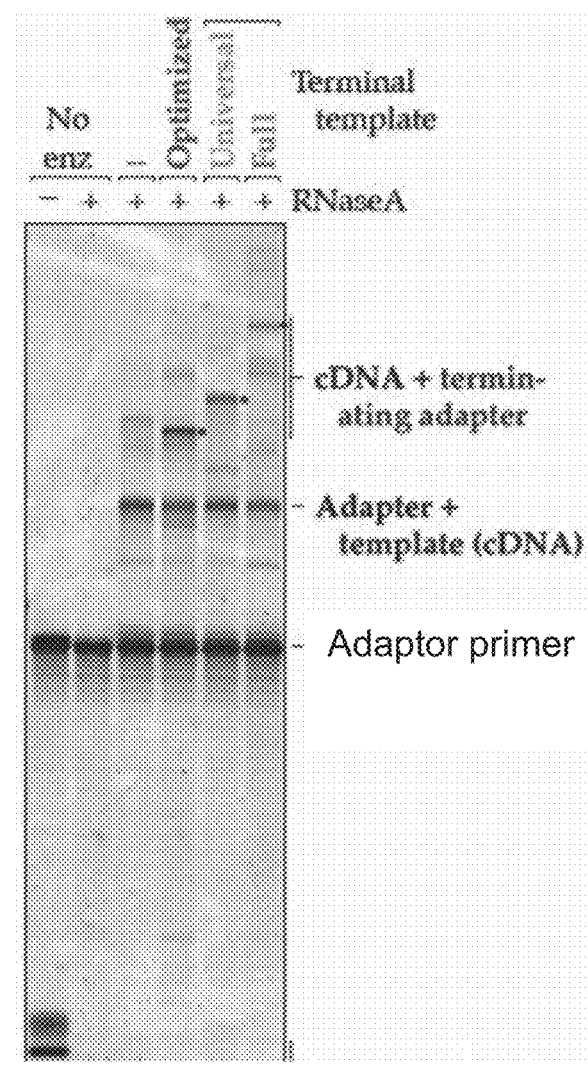

COMPOSITIONS AND METHODS FOR ORDERED AND CONTINUOUS COMPLEMENTARY DNA (cDNA) SYNTHESIS ACROSS NON-CONTINUOUS TEMPLATES

SEQUENCE LISTING

The instant application contains a Sequence Listing which has been submitted electronically in ASCII format and is hereby incorporated by reference in its entirety. Said ASCII copy, created on Mar. 15, 2021, is named SequenceListing2.txt and is 132,288 bytes in size.

FIELD OF THE INVENTION

This invention relates to methods and compositions for controlled nucleic acid synthesis, including ordered and continuous complementary DNA (cDNA) synthesis across non-continuous templates.

BACKGROUND OF THE INVENTION

RNA is the DNA genetic code, or the genomic code of viruses, in action. RNA contains relatively streamlined instructions for and consequences of a current state, rather than the difficult-to-interpret DNA encyclopedia of every possible state. However, unbiased and unaltered sequence recovery from information-rich RNA is challenged by methods for its conversion to cDNA, which is the substrate for PCR-based sequence detection (e.g., for the presence of HIV and other viruses), hybridization-based microarray profiling (e.g., for non-coding RNAs), high-throughput sequencing (e.g., for single-cell or bulk mRNA transcriptome profiling), and other read-outs.

Thus, there exists an unment need for technologies that are individually and collectively transformative for analysis of intact or fragmented RNA and/or DNA, of known or unknown nucleotide content, for research and clinical applications, including nucleic acid hybridization, PCR, and next-generation sequencing (NGS) using multiple platforms.

SUMMARY OF THE INVENTION

This invention relates to, inter alia, compositions and methods for controlled nucleic acid synthesis, including ordered and continuous complementary DNA (cDNA) synthesis across non-continuous templates and non-native terminal transferase activities of non-retroviral RT proteins.

In one aspect, the invention features an isolated eukaryotic non-long terminal repeat reverse transcriptase (non-LTR RT) protein comprising a truncated N-terminal region, an RNA binding domain, an RT domain, and an endonuclease domain, wherein the endonuclease domain comprises a mutation that abolishes endonuclease function. In some aspects, the eukaryotic non-LTR RT protein is an R2 retroelement RT (R2 RT) protein. In some aspects, the truncated N-terminal region results in a deletion of 69 to 303 amino acids from the N-terminus of the non-LTR RT protein as compared to a full-length non-LTR RT protein. In some aspects, the truncated N-terminal region results in a deletion of 69 to 274 amino acids from the N-terminus of the non-LTR RT protein as compared to a full-length non-LTR RT protein. In some aspects, the truncated N-terminal region results in the deletion of all or a portion of a sequence-specific DNA binding domain. In some aspects, the truncated N-terminal domain results in the deletion of all of a sequence-specific DNA binding domain. In some aspects, the truncated N-terminal region results in a deletion of 274 to 303 amino acids from the N-terminus of the non-LTR RT protein as compared to a full-length non-LTR RT protein. In some aspects, the eukaryotic non-LTR RT protein does not comprise a sequence-specific DNA binding domain. In some aspects, the eukaryotic non-LTR RT protein is derived from an arthropod. In some aspects, the arthropod is Bombyx mori.

In some aspects, the eukaryotic non-LTR RT protein is a Bombyx mori R2 RT protein.

In some aspects, the mutation that abolishes endonuclease function is a substitution mutation at amino acid residue D996, D1009, or K1026 of full-length Bombyx mori R2 RT (SEQ ID NO: 1). In some aspects, the substitution mutation is at amino acid residue D996. In some aspects, amino acid residue D996 is substituted by any amino acid, except Glu (E). In some aspects, the substitution mutation is a D996A mutation. In some aspects, the substitution mutation is at amino acid residue D1009. In some aspects, amino acid residue D1009 is substituted by any amino acid, except Glu (E). In some aspects, the substitution mutation is a D1009A mutation. In some aspects, the substitution mutation is at amino acid residue K1026. In some aspects, the substitution mutation is a K1026A, K1026D, or K1026E mutation. In some aspects, the substitution mutation is a K1 026A mutation.

In some aspects, the mutation that abolishes endonuclease function are substitution mutations at amino acid residues K1026 and K1029. In some aspects, the substitution mutations are K1026A and K1029A mutations.

In some aspects, the eukaryotic non-LTR RT protein comprises a stabilizer protein. In some aspects, the stabilizer protein is connected to the N-terminus or the C-terminus of the eukaryotic non-LTR RT protein. In some aspects, the stabilizer protein is connected to the eukaryotic non-LTR RT protein by a linker peptide. In some aspects, the stabilizer protein is a maltose binding protein (MBP), or variant thereof. In some aspects, the stabilizer protein is connected to the N-terminus of the eukaryotic non-LTR RT protein.

In some aspects, the eukaryotic non-LTR RT protein comprises a purification tag. In some aspects, the purification tag is connected to the N-terminus or the C-terminus of the eukaryotic non-LTR RT protein. In some aspects, the purification tag is connected to the eukaryotic non-LTR RT protein by a linker peptide. In some aspects, the purification tag is a histidine tag, a protein A tag, or a FLAG peptide tag. In some aspects, the histidine tag is a 6×-histidine tag. In some aspects, the protein A tag is a tandem protein A tag. In some aspects, the FLAG peptide tag is a 3×-FLAG peptide tag. In some aspects, the purification tag is connected to the C-terminus of the eukaryotic non-LTR RT protein. In some aspects, the linker peptide is a cleavable linker.

In another aspect, the invention features an isolated eukaryotic non-LTR RT protein comprising the amino acid sequence of SEQ ID NO: 2.

In another aspect, the invention features an isolated eukaryotic non-LTR RT protein comprising the amino acid sequence of SEQ ID NO: 3.

In some aspects, the eukaryotic non-LTR RT protein is substantially devoid of nucleic acid contaminants.

In another aspect, the invention features a method of extending the 3' end of a single-stranded or partially single-stranded nucleic acid by at least one nucleotide, the method comprising contacting the single-stranded or partially single-stranded nucleic acid with a non-retroviral RT protein having nucleotide polymerase activity in a buffer comprising manganese ions. The manganese ions are typically in a defined and/or predetermined concentration, suffient to support the polymerase activity, typically in the range of 0.1 to 10 mM or 0.5 to 5 mM. In some aspects, the single-stranded or partially single-stranded nucleic acid is DNA. In some aspects, the contacting is carried out in the absence of a terminal deoxynucleotidyl transferase (TdT), a retroviral RT protein, or any other non-RT protein. In some aspects, the single-stranded or partially single-stranded nucleic acid is RNA. In some aspects, the contacting is carried out in the absence of an RNA ligase or poly-adenosine RNA polymerase, poly-uridine RNA polymerase, or any other non-RT protein.

In another aspect, the invention features a method of extending the 3' ends of an A-form nucleic acid duplex by at least one nucleotide, the method comprising contacting the A-form nucleic acid duplex with a non-retroviral RT protein having nucleotide polymerase activity in a buffer comprising manganese ions. In some aspects, the A-form nucleic acid duplex is an RNA-RNA nucleic acid duplex, a partially RNA-RNA nucleic acid duplex, or a modified form thereof. In some aspects, one or both ends of the RNA-RNA nucleic acid duplex, partially RNA-RNA nucleic acid duplex, or modified form thereof, are blunt-ended or comprise a one-nucleotide or other short 3' overhang. In some aspects, the A-form nucleic acid duplex is an RNA-DNA nucleic acid duplex, a partially RNA-DNA nucleic acid duplex, or a modified form thereof. In some aspects, one or both ends of RNA-DNA nucleic acid duplex, partially RNA-DNA nucleic acid duplex, or modified form thereof, are blunt-ended or comprise a one-nucleotide or other short 3' overhang.

In some aspects, the non-retroviral RT protein is a eukaryotic non-LTR RT protein or a prokaryotic or organellar intron RT protein. In some aspects, the non-retroviral RT protein is a eukaryotic non-LTR RT protein. In some aspects, the non-retroviral RT protein is a eukaryotic non-LTR RT protein of an aspect described herein. In some aspects, the eukaryotic non-LTR RT protein is an R2 RT protein. In some aspects, the R2 RT protein is a *Bombyx mori* R2 RT protein. In some aspects, the non-retroviral RT protein is a prokaryotic or organellar intron RT protein. In some aspects, the prokaryotic or organellar intron RT is a *Eubacterium* rectale group II intron RT protein.

In some aspects, the buffer comprises one or more ribonucleoside triphosphates (NTPs), deoxyribonucleoside triphosphates (dNTPs), or dideoxyribonucleoside triphosphates (ddNTPs), or nucleotide analogs thereof. In some aspects, the contacting is carried out at a temperature of between about 4° C. and about 50° C. In some aspects, the contacting is carried out at a temperature of about 37° C.

In another aspect, the invention features a method of preparing a complementary DNA (cDNA) molecule comprising: (a) providing a primer duplex comprising a primer strand and a non-extended strand, wherein the 3' end of the primer strand comprises a +1 pyrimidine nucleotide overhang; (b) providing an RNA template comprising a purine nucleotide at its 3' end; and (c) contacting the primer duplex and the RNA template with a RT in a buffer comprising magnesium ions, wherein the contacting is carried out under conditions effective for production of a cDNA molecule that is substantially complementary to the RNA template. In some aspects, the buffer comprises one or more dNTPs or analogs thereof. In some aspects, the primer strand is a DNA primer strand. In some aspects, the primer strand comprises a 5' overhang. In some aspects, the 5' end of the primer strand or internal site comprises a modification. In some aspects, the modification allows for immobilization or purification of the primer strand or the primer duplex. In some aspects, the modification is a linkage to biotin. In some aspects, the primer strand is a 5' adapter sequence. In some aspects, the non-extended strand comprises DNA, RNA, hybrid DNA and RNA, or a modified form thereof. In some aspects, the 3' end of the non-extended strand comprises a modification. In some aspects, the modification blocks 3' extension. In some aspects, the modification is a 3' C3 spacer or a 3' monophosphate. In some aspects, the RNA template is prepared by the method of an aspect described herein. In some aspects, the primer duplex is prepared by the method of an aspect described herein. In some aspects, the RT is a eukaryotic non-LTR RT protein. In some aspects, the eukaryotic non-LTR RT protein is an R2 RT protein. In some aspects, the R2 RT protein is a *Bombyx mori* R2 RT protein. In some aspects, the eukaryotic non-LTR RT protein is the eukaryotic non-LTR RT protein of an aspect described herein. In some aspects, the RNA template comprises a purine dNTP, NTP, ddNTP, or nucleotide analog at its 3' end. In some aspects, the 5' end of the RNA template comprises a modification. In some aspects, the modification is an irreversible modification. In some aspects, the irreversible modification is a 5' C6 spacer or biotin. In some aspects, the modification is a reversible modification. In some aspects, the reversible modification is a 5' adenylylation. In some aspects, the contacting is carried out in the presence of a second template, wherein the second template comprises a pyrimidine nucleotide at its 3' end. In some aspects, the second template comprises DNA, RNA, hybrid DNA and RNA, or a modified form thereof. In some aspects, the second template comprises a pyrimidine ribonucleotide at its 3' end. In some aspects, the second template is a complement of a 3' adapter sequence. In some aspects, the contacting is carried out under conditions effective for production of a cDNA molecule that comprises the 5' adapter sequence, a sequence substantially complementary to the RNA template, and the 3' adapter sequence. In some aspects, the 5' end of the second template comprises a modification. In some aspects, the modification is an irreversible modification. In some aspects, the irreversible modification is a 5' C6 spacer or biotin. In some aspects, the modification is a reversible modification. In some aspects, the reversible modification is a 5' adenylylation. In some aspects, the contacting is carried out at a temperature of between about 4° C. and about 50° C. In some aspects, the contacting is carried out at a temperature of about 37° C. In some aspects, the method is carried out in a single container.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 1A. High-yield production of various RT proteins: line lengths indicate relative length of R2 RT amino acid sequence among recombinant RT proteins. Above the lines, regions of the full-length protein are indicated from left (N-terminus) to right (C-terminus): sequence-specific DNA binding domains, RNA binding region, RT region, and endonuclease domain.

FIG. 1B. SDS-PAGE and Coomassie staining demonstrate that purified MBP- and 6x-Histidine-tagged RT proteins used for activity assays described herein are suitably free of protein contaminants.

FIG. 1C. Representative 3-column purification yields per volume of bacteria harvested. Different projects were different experimental replicates. Asterisk indicates first step done as batch binding; otherwise all purification steps were done using pre-packed commercial columns. Higher 260 to 280 nm absorbance ratio from the Void volume fraction compared to the pooled protein monomer peak of the final gel filtration column is an indication of nucleic acid contamination.

A or 3' G, in the presence of all 4 dNTP. Products were analyzed by denaturing PAGE and SYBR Gold staining. First lane after the marker at left has no enzyme added. Lane +/−indicates presence or absence of RNase A after product denaturation, which removes the non-extended strand of the primer duplex and the templates. Only the 3' A template was used for cDNA synthesis.

Figure 12:
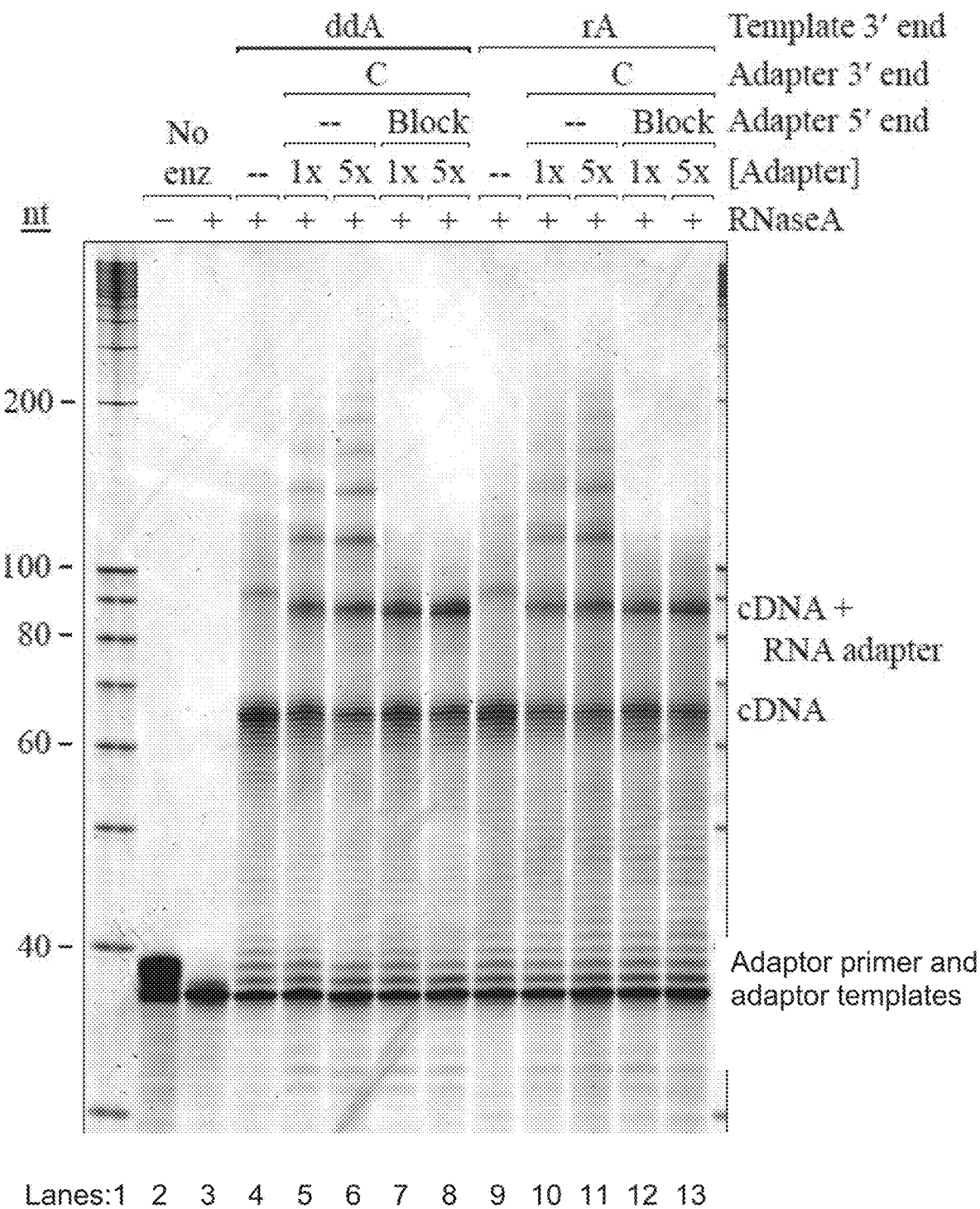

FIG. 12. Use of a 5' blocking group on the cDNA 3' adaptor template for synthesis termination after ordered template relay. Products from reactions containing 400 nM of duplexed 35-nt primer with a +1T overhang, 200 nM of a 27-nt RNA oligonucleotide template with 3' A ribonucleotide or 3' ddA, a 23-nt cDNA 3' adaptor template with 3' C, all 4 dNTPs (250 micromolar each), and BomoC(ed) were analyzed by denaturing PAGE and SYBR Gold staining. Two versions of the 3' adaptor template sequence were tested differing only by the absence or presence of a 5' blocking group (amino modifier C6, IDT) to terminate cDNA synthesis; for each, two adaptor template concentrations were used (400 and 2000 nM for 1× and 5×, respectively). "No enz" lanes show migration of the strands of the duplex primer, which has a non-extended RNA strand with a 3' block to extension. Lane +/−indicates presence or absence of RNase A after product denaturation; RNase A removes the non-extended strand of the primer duplex and the templates, which migrate in a region of the gel below the DNA primer and products shown. Product of primer elongation across a single 3' A or 3' ddA template migrates at "cDNA," product of additional cDNA elongation across a single 3' adaptor template migrates at "cDNA+RNA adapter" and longer products have tandem repeats of 3' adaptor template synthesis.

Figure 13A:
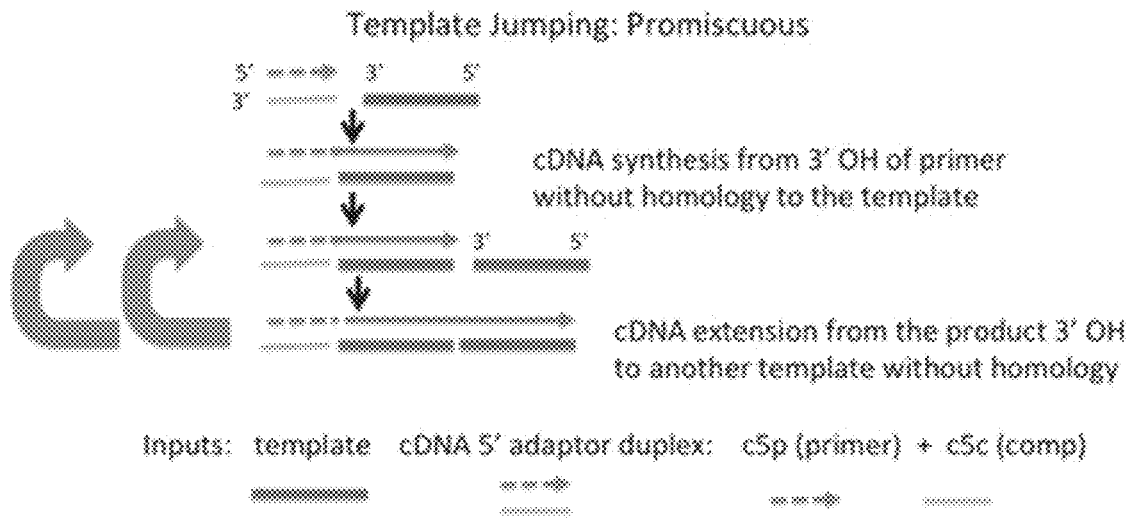
Figure 13B:
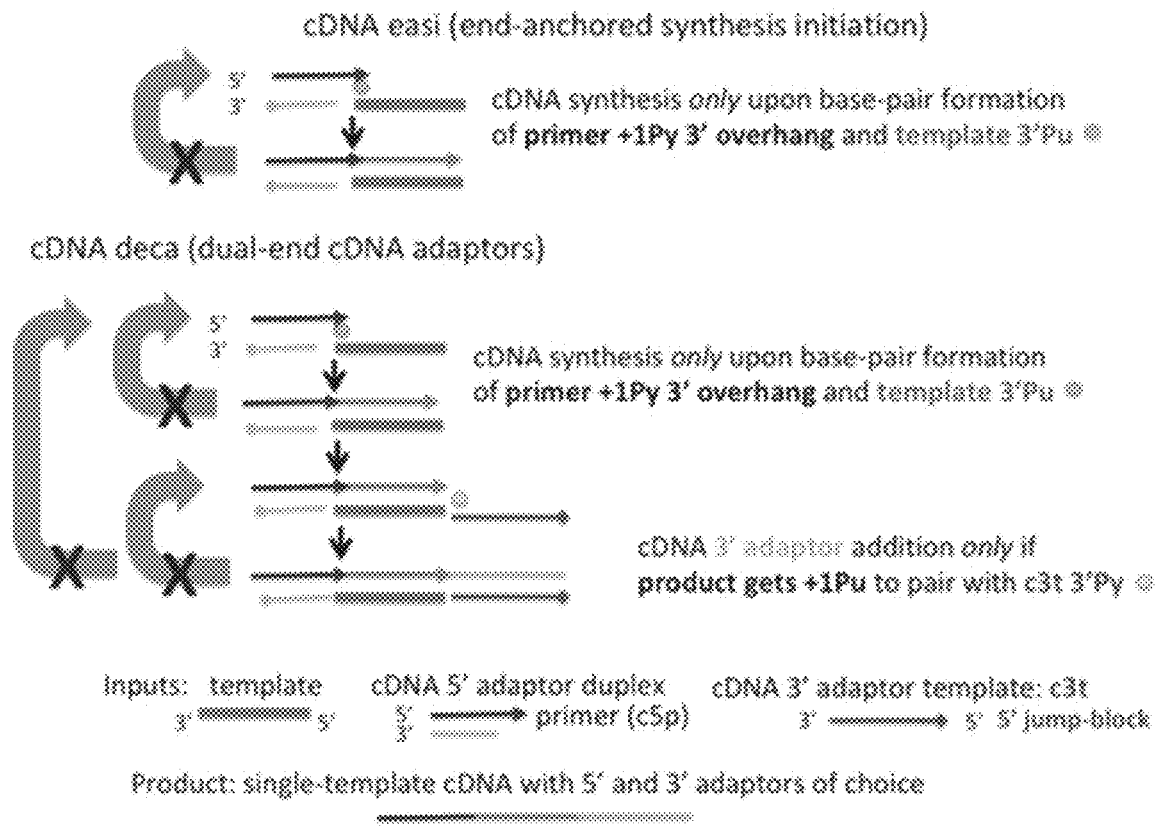

FIG. 13A and FIG. 13B show a set of schematic diagrams showing specificity principles and outcomes that differentiate semi-random template jumping, and ordered template relay. In FIG. 13B, the first step of ordered template relay primes cDNA synthesis across a molecule from the template pool (one-template relay=cDNAeasi). Then second step uses the cDNA 3' end as primer to copy a molecule of 3' adaptor template (two-template relays=cDNAdeca).

FIG. 14A. cDNA synthesis by ordered template relay using adaptor sequences for Illumina NGS. Products from reactions with BomoC(ed), primers with +1T overhang 3' end, and 3' C adaptor templates with 5' block to template relay synthesis were analyzed by denaturing PAGE and SYBR Gold staining. Template was a unique-sequence RNA oligonucleotide with appended 3' ddA. Lane —/+indicates absence or presence of RNase A after product denaturation, which removes the non-extended strand of the primer duplex and the templates. "No enz" is the no enzyme control. Terminal template indicates the cDNA 3' adaptor template used in the reaction: no adaptor template (—), a random sequence (Optimal), an ~35 nt primer containing Illumina Read1 (Universal), or the full-length ~70 nt Illumina NGS adaptor comprised of P5, bar code i5, and Read1 (Full). Demonstration of ordered template relay cDNA synthesis using the ~35 nt Universal cDNA 5' adaptor primer (containing the complement of Read2).

FIG. 14B. Demonstration of ordered template relay cDNA synthesis using the ~70 nt cDNA 5' adaptor primer (containing the complement of P7, bar code i7, and Read2). Product of primer elongation across a single template migrates at "cDNA," and product of additional cDNA elongation across a single 3' adaptor template migrates at "cDNA+terminating adapter."

Figure 15A:
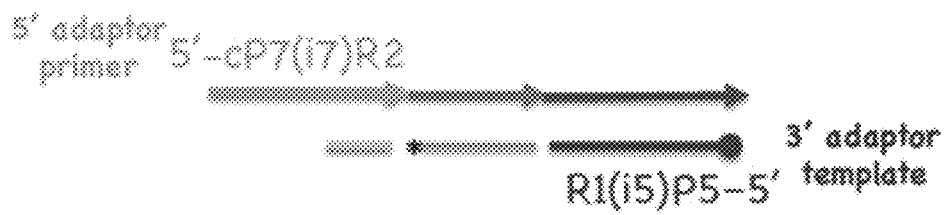

FIG. 15A. PCR-free ordered template relay cDNA library. Library is made using ~70 nt cDNA 5' adaptor primer with +1T overhang and ~70 nt cDNA 3' adaptor template with 3'C and 5' cDNA synthesis block The schematic depicts the oligonucleotides of the partial-duplex primer (primer strand is complement of P7(i7)R2 Illumina NGS adaptor) and the adaptor template (sense P5(i5)R2 Illumina NGS adaptor). The template RNA pool was tailed with 3' ddA (indicated as *) during the ordered template relay workflow.

Figure 15B:
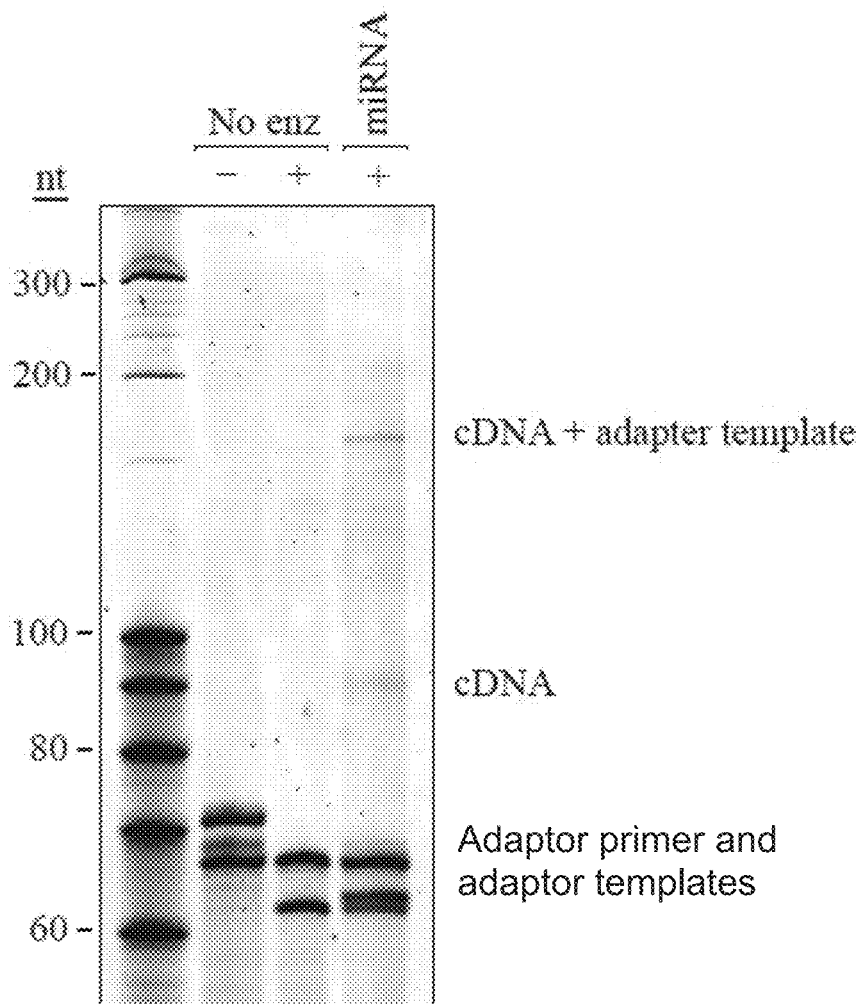

FIG. 15B. Analysis of reaction products by denaturing PAGE and SYBR Gold staining using a template RNA pool of 963 equimolar miRNA sequences (miRXplore). The full-length cDNA library (labeled cDNA+adaptor template) and some cDNA product from copying of the miRNA template only (labeled cDNA) are the predominant products. Excess adaptor primer and adaptor template are also stained. "No enz" is the no enzyme control. Lane +/−indicates addition of RNase A after product denaturation, which removes the non-extended strand of the primer duplex and truncates the ~70 nt 3' adaptor template. The library was sequenced with results shown in comparison to a low-cycle-PCR library in FIG. 16B.

Figure 16A:
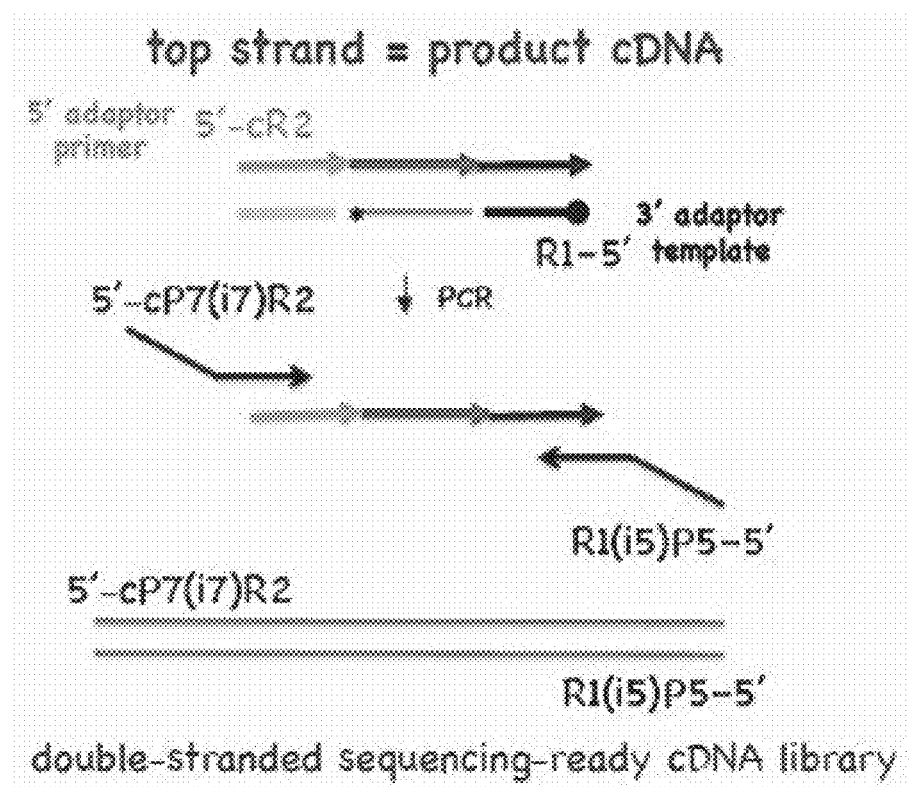

FIG. 16A. Low-cycle PCR ordered template relay cDNA library. Schematic showing use of ~35 nt cDNA 5' adaptor primer with +1T overhang (primer label cR2=complement of Illumina Read2) and ~35 nt cDNA 3' adaptor template with 3'C and 5' cDNA synthesis block (adaptor template label R1=Illumina Read 1; 5' block=filled circle). Template pool is the thin line with asterisk indicating 3' ddA. Arrowheads point 5' to 3' on the cDNA (top strand). Subsequent PCR incorporate indexing (i) bar codes and the P5/P7 sequences.

Figure 16B:
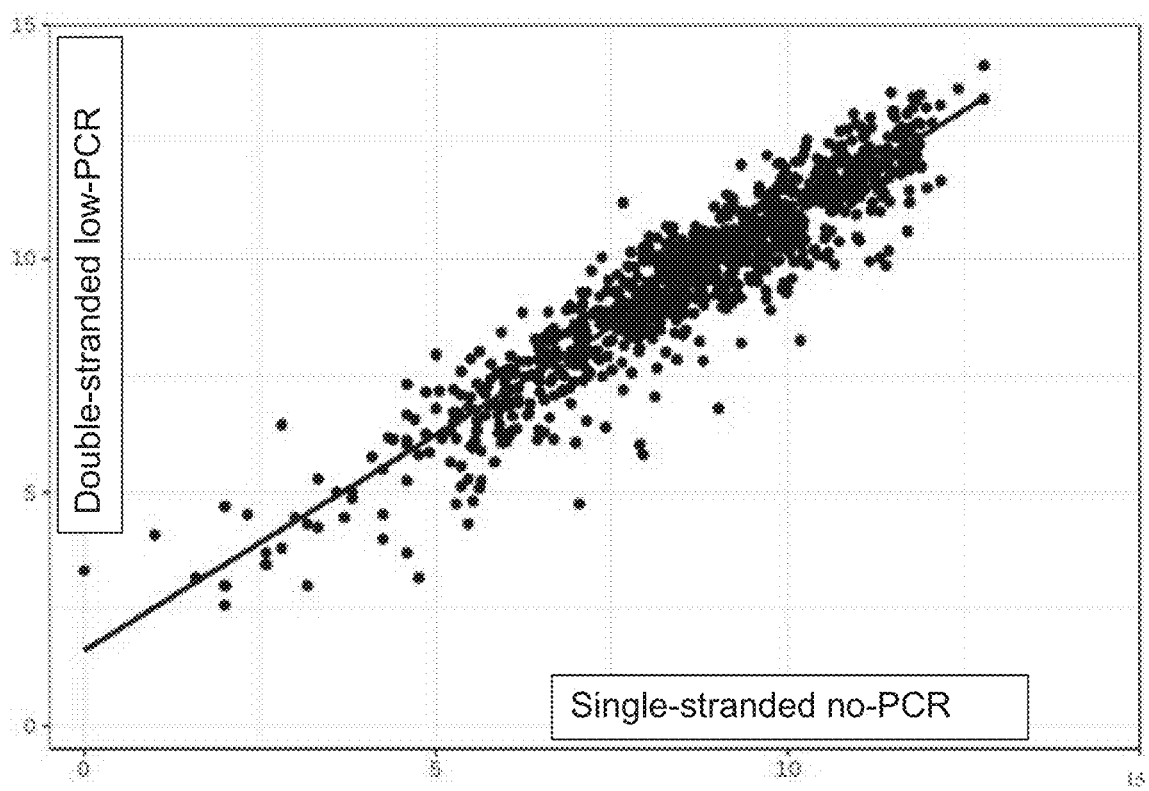

FIG. 16B. Plot showing read counts for each of the 963 equimolar miRNA sequences (miRXplore standard) comparing log 2 scale of relative read count obtained by sequencing low-PCR library (dsDNA, Y axis scale; 8 cycles PCR) versus no-PCR library (ssDNA, X axis scale). Each miRNA represented by a black dot. The log 2 scale apparent zero count for one miRNA in the PCR-free library is a false zero. Perfect agreement would place each dot on the line that was fit through the actual data.

DETAILED DESCRIPTION OF EMBODIMENTS OF THE INVENTION

Introduction

The present invention features compositions and methods for controlled nucleic acid synthesis, including ordered and continuous complementary DNA (cDNA) synthesis across non-continuous templates and non-native terminal transferase activities of non-retroviral RT proteins. Importantly, these methods can be performed in a single container, without any partitioning or immobilization steps.

Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a," "an," and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

The term "A-form" as used herein refers the structure of nucleic acid duplexes containing at least some RNA nature (typically, RNA-RNA duplexes or RNA-DNA duplexes), which is distinguishable from the structure of nucleic acid duplexes comprised of DNA only, which under typical cellular and physiological buffer conditions adopt a distinct B-form structure. DNA-DNA duplexes may be favored to adopt A-form geometry in certain environments or when bound by some proteins, but duplexes containing an RNA strand are not observed to adopt B-form due to impediment from the extra hydroxyl group of the ribose sugar.

"Amplification," as used herein generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

Throughout this specification and claims, the word "comprise," or variations such as "comprises" or "comprising," will be understood to imply the inclusion of a stated integer or group of integers but not the exclusion of any other integer or group of integers.

As used herein, the term "cognate" is meant to indicate the presence of base(s) that are able to form base-pairing consistent with canonical geometry of nucleic acid duplexes.

By "container" is meant a shaped article with a top, bottom, and sides, wherein the top contains an opening for access to an interior that is able to contain liquid, gaseous, and/or solid samples (e.g., a reaction mixture). In some embodiments, the container may have an openable top surface, for example, a lid, cover, or cap. In some embodiments, the container is a tube (e.g., a polypropylene tube).

As used herein, the term "enzyme" includes proteins produced by a cell capable of catalyzing biochemical reactions. Further, unless context dictates otherwise, as used herein "enzyme" includes protein fragments that retain the relevant catalytic activity and may include artificial enzymes synthesized to retain the relevant catalytic activity.

"Isolated," when used to describe various reverse transcriptase (RT) proteins or protein fragments disclosed herein, means a protein that has been identified and separated and/or recovered from a cell or cell culture from which it was expressed. Contaminant components (e.g., nucleic acid contaminants) from an expression environment are materials that remain present in the isolated protein and could typically interfere with its uses. In some aspects, the proteins will be purified to substantial homogeneity, for example, by at least one purification step.

By "linked" or "links" as used herein is meant either a direct peptide bond linkage between a first and second protein or polypeptide, or a linkage that involves a third amino acid sequence that is peptide bonded to and between the first and second proteins or polypeptides. For example, amino acids may link the C-terminal end of one protein or polypeptide and to the N-terminal end of the other protein or polypeptide.

By "linker" as used herein is meant an amino acid sequence of two or more amino acids in length. The linker can consist of neutral, polar, or nonpolar amino acids. A linker can be, for example, 2 to 100 amino acids in length, such as between 2 and 50 amino acids in length, for example, 3, 5, 10, 15, 20, 25, 30, 35, 40, 45, or 50 amino acids in length. A linker can be "cleavable," for example, by enzymatic or chemical cleavage that may be self-mediated or mediated by a physically separate agent. Cleavage sites in amino acid sequences and enzymes and chemicals that cleave at such sites are well known in the art and are also described herein. In some aspects, a linker covalently links one molecule and another molecule through peptide bonds. In some aspects, a linker is a region that promotes folding of the adjacent protein(s) or polypeptide(s) as described in Smyth et al. *Protein Science*. 12: 1313-1322, 2003.

The term "package insert" is used to refer to instructions, customarily included in commercial packages of products such as kits, that contain information about the usage of such products.

As used herein, the term "reverse transcriptase" or "RT" refers to a protein polymerase that in an intact, unmutated state can catalyze the polymerization of deoxynucleoside triphosphates (dNTPs) cognate to an RNA template. Many RTs also can use a DNA template. Some RTs have degenerated evolutionarily to inactive form yet have a discernable phylogenetic relationship to active RTs. RTs have uses including using RNA to template synthesis of a complementary DNA (cDNA), which can then with additional steps be cloned into a vector for further manipulation or used in various amplification methods such as polymerase chain reaction (PCR), isothermal amplification (e.g., nucleic acid sequence-based amplification (NASBA)), transcription-mediated amplification (TMA), and self-sustained sequence replication (3SR). cDNA synthesis by RT is used for diverse primer extension reaction protocols, rapid amplification of cDNA ends (RACE), detection of chemical modifications, and other techniques that benefit from cDNA readout of RNA and/or sometimes also DNA templates.

As used herein, the term "intron RT protein" or "bacterial intron RT protein" refers to a naturally occurring RT protein encoded within an intron (iRT), typically found in prokaryotic cells or eukaryotic cellular organelles, not restricted to bacterial species but best characterized in those organisms.

As used herein, the term "non-long terminal repeat reverse transcriptase protein" or "non-LTR RT protein" refers to a naturally occurring protein encoded by a eukaryotic non-LTR retrotransposon, polypeptide fragment thereof that possesses DNA polymerase activity, as well as a polypeptide variant derived therefrom that contains one or more amino acid substitutions, additions, or deletions that preserve or enhance RT activity (e.g., specific activity) and/or purification yield. A preferred class of non-LTR RT proteins are R2 and R2-related, or R2-like, retroelement RT (R2 RT) proteins. Thus, as used herein, "R2 RT protein" or "R2 RT polypeptide" refers to a naturally occurring protein encoded by R2 elements or a polypeptide fragment thereof that possesses some property of the intact RT protein, as well as a polypeptide variant derived therefrom that contains one or more amino acid substitutions, additions, or deletions that preserve or enhance a desirable property or activity (e.g., specific activity) and/or purification yield. The R2 RT protein variant may, for example, contain one or more amino acid substitutions, additions, or deletions that preserve or enhance RT activity and/or terminal transferase activity. In some aspects, the R2 RT protein is a R2 RT protein from an arthropod, such as a *Bombyx mori* R2 RT protein (e.g., a *Bombyx mori* R2 RT protein having a truncated N-terminal region (e.g., a truncated N-terminal region that results in a deletion of 70 to 303 amino acids (e.g., a deletion of 70 to 274 amino acids and/or a deletion of 274 to 303 amino acids) from the N-terminus of the *Bombyx mori* R2 RT protein as compared to full-length *Bombyx mori* R2 RT (SEQ ID NO: 1)), an RNA binding domain, an RT domain, and an endonuclease domain, wherein the endonuclease domain comprises a mutation that abolishes endonuclease function (e.g., a substitution mutation at amino acid residue D996, D1009, or K1026 and K1029 of full-length *Bombyx mori* R2 RT (SEQ ID NO: 1), e.g., a D996A mutation).

As used herein, the term "non-retroviral reverse transcriptase protein" or "non-retroviral RT protein" is inclusive of RTs and RT-related proteins evolved in a cellular genome, which include non-LTR RT proteins and bacterial or organellar intron RT (iRT) proteins, but which do not include RTs that evolved in retrovirus genomes. In contrast to typical retrovirus RTs, some cellular RTs do not require extensive base pairing of primer with template to initiate synthesis. Examples of non-retroviral RT proteins include non-LTR RT proteins, telomerase, and iRTs from self-splicing group II introns. Further bacterial RT proteins are described by Simon and Zimmerly. *Nucleic Acids Res.* 36(22):7219-7229, 2008 and Kojima and Kanehisa. *Mol Biol Evol.* 25:1395-1404, 2008, which describe many additional classes of non-retroviral reverse transcriptases (i.e., RTs from retrons and diversity-generating retroelements among others).

The technique of "polymerase chain reaction" or "PCR" as used herein generally refers to a procedure wherein minute amounts of a specific piece of nucleic acid, RNA and/or DNA, are amplified as described, for example, in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., Cold Spring Harbor Symp. Quant. Biol. 51:263 (1987) and Erlich, ed., PCR Technology, (Stockton Press, N Y, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

"Polynucleotide" or "nucleic acid," as used interchangeably herein, refers to polymers of nucleotides of any length (e.g., at least 2, 3, 4, 5, 6, 7, 8, 9, 10, 20, 30, 40, 50, 100, 150, 200, 250, 500, 1000, or more nucleic acids), and include DNA and RNA, fragments, or analogs thereof. The nucleotides can be deoxyribonucleotides, ribonucleotides, modified nucleotides or bases, and/or their analogs, or any substrate that can be incorporated into a polymer by a DNA or RNA polymerase or a functionally active polymerase domain, or by a synthetic reaction. The following are non-limiting examples of polynucleotides: coding or noncoding regions of a gene or gene fragment, loci (locus) defined from linkage analysis, exons, introns, messenger RNA (mRNA), transfer RNA, transfer-messenger RNA, ribosomal RNA, antisense RNA, small nuclear RNA (snRNA), small nucleolar RNA (snoRNA), micro-RNA (miRNA), small interfering RNA (siRNA), ribozymes, cDNA, recombinant polynucleotide open reading frames (ORFs), branched polynucleotides, plasmids, vectors, isolated DNA of any sequence, isolated RNA of any sequence, nucleic acid probes, and primers.

As noted above, a polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after synthesis/polymerization, such as by conjugation with a label. Other types of modifications include, for example, "caps," substitution of one or more of the naturally occurring nucleotides with an analog, internucleotide modifications such as, for example, those with linkages not observed in nature (e.g., methyl phosphonates, phosphotriesters, phosphoamidates, carbamates, phosphorothioates, phosphorodithioates, etc.), those containing pendant moieties, such as, for example, polypeptides (e.g., nucleases, toxins, antibodies, signal peptides, poly-L-lysine, etc.), those with intercalators (e.g., acridine, psoralen, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms or more.

Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses, pyranose sugars, furanose sugars, and acyclic analogs.

A nucleic acid described herein can contain phosphodiester bonds, although the term "nucleic acid" also encompasses nucleic acid analogs having other types of linkages or backbones (e.g., phosphoramide, phosphorothioate, phosphorodithioate, O-methylphosphoroamidate, morpholino, locked nucleic acid (LNA), glycerol nucleic acid (GNA), threose nucleic acid (TNA), and peptide nucleic acid (PNA) linkages or backbones, among others). In some embodiments, the nucleic acids can be DNA (including, e.g., genomic DNA, mitochondrial DNA, cDNA, cell-free DNA (cfDNA), ancient DNA, damaged DNA from formaldehyde-fixed paraffin-embedded (FFPE) tissue samples or cells, as well as fragments of any of the DNAs), RNA (including, e.g., mRNA, rRNA, tRNA, miRNA, cell-free RNA (cfRNA), and RNA from FFPE tissue samples or cells, as well as fragments of any of the RNAs) or a hybrid (also described as "chimera"), where the nucleic acid contains any combination of deoxyribonucleotides and ribonucleotides, and any combination of bases, including uracil, adenine, thymine, cytosine, guanine, inosine, and modified or non-canonical bases (including, e.g., hypoxanthine, xanthine, 7-methylguanine, 5,6-dihydrouracil, 5-methylcytosine, and 5 hydroxymethylcytosine). A polynucleotide is intended to encompass a singular nucleic acid as well as plural nucleic acids. The polynucleotide may be composed of any polyribonucleotide or polydeoxyribonucleotide, which may be unmodified RNA or DNA or modified RNA or DNA. For example, polynucleotides may be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The preceding description applies to all polynucleotides referred to herein, including RNA and DNA.

By "polypeptide" or "protein" is meant any natural or synthetic chain of amino acids at least two amino acids (e.g., 5, 10, 20, 30, 40, 50, 60, 70, 80, 90, 100, 125, 150, 175, 200, 225, 250, 275, 300, 325, 350, 375, 400, 425, 450, 475, 500, 525, 550, 575, 600, 700, 800, or more amino acids) in length, including those having natural or induced modification by enzymes or chemical agents (e.g, glycosylation or phosphorylation).

By "portion" or "fragment" is meant a part of a whole. A portion may comprise at least 10%, 20%, 30%, 40%, 50%, 60%, 70%, 80%, 90%, 95%, 99%, 99.1%, 99.2%, 99.3%, 99.4%, 99.5%, 99.6%, 99.7%, 99.8%, or 99.9% of the entire length of a polynucleotide or polypeptide sequence region. For polynucleotides, for example, a portion may include at least 5, 6, 7, 8, 9, 10, 20, 30, 40, 50, 60, 70, 80, 90, 100, 200, 300, 400, 500, 600, 700, 800, 900, 1000, 2000, or more contiguous nucleotides of a reference polynucleotide molecule. For polypeptides, for example, a portion may include at least 3,4,5,6,7,8,9,10,11,12,13,14,15,16,17,18,19,20,25, 50,75,90,100, 125, 150, 175, 200, 225, 250, 275, 300, 350, 400, 450, 500, 550, 600, 650, 700, 750 or more contiguous amino acids of a reference polypeptide molecule. In the context of truncated variants of a given protein (e.g., a non-LTR RT protein having a truncated region), the truncation may be from the N-terminus and/or from the C-terminus of the protein and results in a deletion of one or more contiguous amino acids from the respective terminus or termini as compared to a full-length version of the given protein (e.g., a full-length non-LTR RT protein). An N-terminal truncation will lack, for example, all of the full-length protein amino acids 1-4, 1-10, 1-200, 1-250, 1-500 or intermediate or larger numbers of amino acids.

By "sequence identity" or "sequence similarity" is meant that the identity or similarity between two or more amino acid sequences, or two or more nucleotide sequences, is expressed in terms of the identity or similarity between the sequences. Sequence identity can be measured in terms of "percentage (%) identity," wherein the higher the percentage, the more identity shared between the sequences. Sequence similarity can be measured in terms of percentage similarity (which takes into account conservative amino acid substitutions); the higher the percentage, the more similarity shared between the sequences. Homologs or orthologs of nucleic acid or amino acid sequences possess a relatively high degree of sequence identity/similarity when aligned using standard methods. An optimal alignment of sequences can be determined in various ways that are within the skill in the art, for instance, the Smith Waterman alignment algorithm (Smith et al. *J. Mol. Biol.* 147:195-7, 1981) and BLAST (Basic Local Alignment Search Tool; Altschul et al. *J. Mol. Biol.* 215: 403-10, 1990). These and other alignment algorithms are accessible using publicly available computer software such as "Best Fit" (Smith and Waterman, Advances in Applied Mathematics, 482-489, 1981) as incorporated into GENEMATCHER PLUS™ (Schwarz and Dayhof, Atlas of Protein Sequence and Structure, Dayhoff, M. O., Ed pp 353-358, 1979), BLAST, BLAST-2, BLAST-P, BLAST-N, BLAST-X, WU-BLAST-2, ALIGN, ALIGN-2, CLUSTAL, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, 800 or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, 2200, 2300, 2400 or more nucleotides, up to the entire length of the nucleic acid molecule. It is understood that for the purposes of determining sequence identity when comparing a DNA sequence to an RNA sequence, a thymidine nucleotide (T) is equivalent to a uridine nucleotide (U). Other naturally occurring nucleotides include, but are not limited to, adenosine (A), cytidine (C), guanosine (G), and inosine (I). Furthermore, homology and similarity can be compared by propensity to adopt the same fold (secondary and/or tertiary structure) using modeling programs such as PHYRE2 (Kelly et al. *Nat. Protocols.* 10: 845-858, 2015) and Mfold (Zuker. *Nucleic Acids Res.* 31(13): 3406-3415, 2003).

A "stabilizer polypeptide" or "stabilizer protein," as defined herein, is a protein forming part of a fusion protein that functions to increase the overall stability of the fusion protein by, for example, increasing the overall stability of another protein of the fusion protein. Stability includes the ability of the protein to retain its conformation and activity. In addition, the stabilizer protein may enhance the solubility of the fusion protein or another protein of the fusion protein. The use of a stabilizer protein can also provide other advantages such as increased protein expression, improved protein folding, and short-term or long-term storage with retained specific activity. Inclusion of a linker peptide between a stabilizer protein and a non-LTR RT protein can further enhance these advantages. In some aspects, a stabilizer protein is connected to a eukaryotic non-LTR RT protein of the invention for expression of the fusion protein in bacterial cells. In some aspects, the stabilizer protein is maltose binding protein (MBP).

The modified RT proteins of the present invention are generally purified to substantial homogeneity. The phrases "substantially homogeneous," "substantially homogeneous form" and "substantial homogeneity" are used to indicate that the product (i.e., the isolated RT protein) is substantially devoid of contaminants from the expression context, such as tightly associated nucleic acids, associated proteins, and/or other heterologous contaminating material. For example, the modified RT proteins may exhibit a 95% or greater (e.g., 96%, 97%, 98%, 99%, or 99.5% or greater) reduction in contaminants from the expression context as compared to a similar, but unmodified, RT protein following the same or nearly identical purification protocol(s).

As used herein, the terms "variant," "modified," "non-naturally occurring," and "mutant" are synonymous and refer to a polypeptide or nucleic acid differing from a specifically recited polypeptide or nucleic acid by one or more amino acid or nucleotide insertions, deletions, mutations, substitutions, modifications or fusions created using, e.g., recombinant DNA techniques, such as site-specific mutagenesis. Guidance in determining which residues may be replaced, added, or deleted without abolishing activities of interest, may be found by comparing the sequence of the particular polypeptide with that of homologous polypeptides, e.g., phylogenetically related sequences, and minimizing the number of changes made in regions of high homology (conserved regions) or by replacing with consensus sequences. In some embodiments, the terms "derivative," "variant," "modified," "non-naturally occurring," and "mutant" are used interchangeably.

Modified Eukaryotic Non-Long Terminal Repeat Reverse Transcriptase (non-LTR RT) Proteins Provided herein are isolated eukaryotic non-long terminal repeat reverse transcriptase (non-LTR RT) proteins for use in methods and compositions of the present disclosure. The isolated eukaryotic non-LTR RT proteins exhibit robust expression, high-yield purification free of nucleic acids, cDNA synthesis activity on an annealed primer-template substrate such as used in a retroviral RT assay, and template "jumping" activity allowing processive copying of multiple physically separate templates to generate a single covalently continuous cDNA. Such isolated eukaryotic non-LTR RT proteins include a truncated N-terminal region, an RNA binding domain, an RT domain, and an endonuclease domain, wherein the endonuclease domain includes a mutation that abolishes endonuclease function.

In some instances, the eukaryotic non-LTR RT protein is an R2-like retroelement RT (R2-like RT) protein (e.g., an R2-like RT protein). An R2-like protein would share the general principles of protein architecture including, in linear order from the protein N- to C-terminus: one or more sequence-specific DNA binding domains not present in intron or retroviral RTs, a RNA binding region present in intron RTs but not present in retroviral RTs, a shared RT domain with intact or degenerate signature motifs of the RT active site, and a C-terminal endonuclease domain from the restriction-like endonuclease (RLE) family. Other non-retroviral RTs that are not R2-like either lack an endonuclease domain or have an endonuclease domain from a different structural family. In some instances, the eukaryotic non-LTR RT protein is an R2 retroelement RT (R2 RT) protein. In some instances, the eukaryotic non-LTR RT protein is derived from an arthropod. In some instances, the arthropod is *Bombyx mori*, and the protein is a *Bombyx mori* R2 RT protein.

In some instances, the truncated N-terminal region results in a deletion of 69 (i.e., amino acids 1-69) to 303 (i.e., amino acids 1-303) amino acids from the N-terminus of the non-LTR RT protein as compared to a full-length non-LTR RT protein. For example, the truncated N-terminal region may result in a deletion of the N-terminal 69 amino acids (i.e., amino acids 1-69) of the non-LTR RT protein as compared to an untruncated, full-length non-LTR RT protein. Accordingly, in some instances, the truncated N-terminal region may result in a deletion of the N-terminal 69 amino acids (i.e., amino acids 1-69) of a *Bombyx mori* R2 RT protein as compared to an untruncated, full-length *Bombyx mori* R2 RT protein having an amino acid sequence of SEQ ID NO: 1. Thus, in one instance, the eukaryotic non-LTR RT protein having a truncated N-terminal region resulting in a deletion of the N-terminal 69 amino acids (i.e., amino acids 1-69) of a *Bombyx mori* R2 RT protein as compared to an untruncated, full-length *Bombyx mori* R2 RT protein having an amino acid sequence of SEQ ID NO: 1 may include the amino acid sequence of SEQ ID NO: 9. An isolated eukaryotic non-LTR RT protein including the amino acid sequence of SEQ ID NO: 9 is, for example, the ΔN69 R2 RT protein, described in detail in the present disclosure.

Alternatively, the non-LTR RT protein having a truncated N-terminal region may be a variant of SEQ ID NO: 9 having an amino acid sequence having at least 90% sequence identity (e.g., at least 91%, 92%, 93%, 94%, 95%, 96%, 97%, 98%, 99%, or 99.5% sequence identity) to SEQ ID NO: 9. Another example of an isolated eukaryotic non-LTR RT protein including the amino acid sequence of SEQ ID NO: 9 is the ΔN69 R2 RT protein with an N-terminal MBP tag and C-terminal 6×His tag having the amino acid sequence of SEQ ID NO: 6.

Other examples of a eukaryotic non-LTR RT protein having a truncated N-terminal region resulting in a deletion of the N-terminal 69 amino acids of a *Bombyx mori* R2 RT protein, as compared to an untruncated, full-length *Bombyx mori* R2 RT protein having an amino acid sequence of SEQ ID NO: 1, include the ΔN69(ed) R2 RT protein having the amino acid sequence of SEQ ID NO: 14. Alternatively, the non-LTR RT protein having a truncated N-terminal region may be a variant of SEQ ID NO: 14 having an amino acid sequence having at least 90% sequence identity (e.g., at least 91%, 92%, 93%, 94%, 95%, 96%, 97%, 98%, 99%, or 99.5% sequence identity) to SEQ ID NO: 14, wherein the variant includes a D996A substitution mutation, at amino acid residue D996 of full-length *Bombyx mori* R2 RT (SEQ ID NO: 1). Another example of an isolated eukaryotic non-LTR RT protein including the amino acid sequence of SEQ ID NO: 14 is the ΔN69(ed) R2 RT protein with an N-terminal MBP tag and C-terminal 6×His tag having the amino acid sequence of SEQ ID NO: 13.

In another example, the truncated N-terminal region may result in a deletion of the N-terminal 303 amino acids (i.e., amino acids 1-303) of the non-LTR RT protein as compared to an untruncated, full-length non-LTR RT protein. Accordingly, in some instances, the truncated N-terminal region may result in a deletion of the N-terminal 303 amino acids (i.e., amino acids 1-303) of a *Bombyx mori* R2 RT protein as compared to an untruncated, full-length *Bombyx mori* R2 RT protein having an amino acid sequence of SEQ ID NO: 1. Thus, in one instance, the eukaryotic non-LTR RT protein having a truncated N-terminal region resulting in a deletion of the N-terminal 303 amino acids (i.e., amino acids 1-303) of a *Bombyx mori* R2 RT protein as compared to an untruncated, full-length *Bombyx mori* R2 RT protein having an amino acid sequence of SEQ ID NO: 1 may include the amino acid sequence of SEQ ID NO: 11. An isolated eukaryotic non-LTR RT protein including the amino acid sequence of SEQ ID NO: 11 is, for example, the BomoMin (ed) protein, described in the present disclosure.

Alternatively, the non-LTR RT protein having a truncated N-terminal region may be a variant of SEQ ID NO: 11 having an amino acid sequence having at least 90% sequence identity (e.g., at least 91%, 92%, 93%, 94%, 95%, 96%, 97%, 98%, 99%, or 99.5% sequence identity) to SEQ ID NO: 11, wherein the variant includes a D996A substitution mutation, at amino acid residue D996 of full-length *Bombyx mori* R2 RT (SEQ ID NO: 1). An isolated eukaryotic non-LTR RT protein including the amino acid sequence of SEQ ID NO: 11 is, for example, the BomoMin(ed) R2 RT protein, described in detail in the present disclosure. Another example of an isolated eukaryotic non-LTR RT protein including the amino acid sequence of SEQ ID NO: 11 is the BomoMin(ed) R2 RT protein with an N-terminal MBP tag and C-terminal 6×His tag having the amino acid sequence of SEQ ID NO: 12.

In some instances, the truncated N-terminal region results in a deletion of 69 (i.e., amino acids 1-69) to 274 amino acids (i.e., amino acids 1-274) from the N-terminus of the non-LTR RT protein as compared to a full-length non-LTR RT protein. For example, the truncated N-terminal region may result in a deletion of the N-terminal 274 amino acids (i.e., amino acids 1-274) of the non-LTR RT protein as compared to an untruncated, full-length non-LTR RT protein. Accordingly, in some instances, the truncated N-terminal region may result in a deletion of the N-terminal 274 amino acids (i.e., amino acids 1-274) of a *Bombyx mori* R2 RT protein as compared to an untruncated, full-length *Bombyx mori* R2 RT protein having an amino acid sequence of SEQ ID NO: 1. Thus, in one instance, the eukaryotic non-LTR RT protein having a truncated N-terminal region resulting in a deletion of the N-terminal 274 amino acids (i.e., amino acids 1-274) of a *Bombyx mori* R2 RT protein as compared to an untruncated, full-length *Bombyx mori* R2 RT protein having an amino acid sequence of SEQ ID NO: 1 may include the amino acid sequence of SEQ ID NO: 10. An isolated eukaryotic non-LTR RT protein including the amino acid sequence of SEQ ID NO: 10 is, for example, the BomoC R2 RT protein, described in detail in the present disclosure.

Alternatively, the non-LTR RT protein having a truncated N-terminal region may be a variant of SEQ ID NO: 10 having an amino acid sequence having at least 90% sequence identity (e.g., at least 91%, 92%, 93%, 94%, 95%, 96%, 97%, 98%, 99%, or 99.5% sequence identity) to SEQ ID NO: 10. Another example of an isolated eukaryotic non-LTR RT protein including the amino acid sequence of SEQ ID NO: 10 is the BomoC R2 RT protein with an N-terminal MBP tag and C-terminal 6×His tag having the amino acid sequence of SEQ ID NO: 7.

Other examples of a eukaryotic non-LTR RT protein having a truncated N-terminal region resulting in a deletion of the N-terminal 274 amino acids (i.e., amino acids 1-274) of a *Bombyx mori* R2 RT protein, as compared to an untruncated, full-length *Bombyx mori* R2 RT protein having an amino acid sequence of SEQ ID NO: 1, include the BomoC(ed) R2 RT protein having the amino acid sequence of SEQ ID NO: 2. Alternatively, the non-LTR RT protein having a truncated N-terminal region may be a variant of SEQ ID NO: 2 having an amino acid sequence having at least 90% sequence identity (e.g., at least 91%, 92%, 93%, 94%, 95%, 96%, 97%, 98%, 99%, or 99.5% sequence identity) to SEQ ID NO: 2, wherein the variant includes a D996A substitution mutation at amino acid residue D996 of full-length *Bombyx mori* R2 RT (SEQ ID NO: 1). Another example of an isolated eukaryotic non-LTR RT protein including the amino acid sequence of SEQ ID NO: 2 is the BomoC(ed) R2 RT protein with an N-terminal MBP tag and C-terminal 6×His tag having the amino acid sequence of SEQ ID NO: 3.

In some instances, the truncated N-terminal region results in a deletion of 274 (i.e., amino acids 1-274) to 303 amino acids (i.e., amino acids 1-303) from the N-terminus of the non-LTR RT protein as compared to a full-length non-LTR RT protein.

In some instances, isolated N-terminal truncated eukaryotic non-LTR RT protein variants having a mutation that abolishes endonuclease function and additionally one or more amino acid substitutions relative to any one of SEQ ID NOs: 2, 3, and 6-14 are provided. Conservative substitutions are shown in Table 1 under the heading of "preferred substitutions." More substantial changes are provided in Table 1 under the heading of "exemplary substitutions," and as further described below in reference to amino acid side chain classes.

TABLE 1

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino Acids May be Grouped According to Common Side-Chain Properties:
  hydrophobic: Norleucine, Met, Ala, Val, Leu, Ile;
  neutral hydrophilic: Cys, Ser, Thr, Asn, Gln;
  acidic: Asp, Glu;
  basic: His, Lys, Arg;
  residues that influence chain orientation: Gly, Pro;
  aromatic: Trp, Tyr, Phe.

Non-conservative substitutions will entail exchanging a member of one of these classes for another class.

In some instances, the truncated N-terminal region results in the deletion of all or a portion of one or more (e.g., one, two, three, or four or more) sequence-specific DNA binding domain(s). In some instances, the truncated N-terminal domain results in the deletion of all of one or more (e.g., one, two, three, or four or more) sequence-specific DNA binding domain(s). In some instances, the eukaryotic non-LTR RT protein does not comprise a sequence-specific DNA binding domain. In some instances, the eukaryotic non-LTR RT protein does not comprise an autonomous sequence-specific DNA binding domain.

In some instances, the isolated eukaryotic non-LTR RT protein is purified to substantial homogeneity. Therefore, in some instances, the eukaryotic non-LTR RT protein is substantially devoid of nucleic acid contaminants.

Endonuclease-Inactivating Mutations

As described above, the isolated eukaryotic non-LTR RT proteins include an endonuclease domain having one or more mutations that abolish endonuclease function. Such mutations may include substitution mutations, deletion mutations (including truncation mutations), or insertional mutations. For example, one or more substitution mutations (e.g., substitution of one or more amino acids with one or more different amino acids) may be used to construct a modified eukaryotic non-LTR RT protein having an inactivated endonuclease domain for use in the present disclosure. Endonuclease domain families have been extensively characterized, including the endonuclease domain from R2-like RT proteins, which is shared with a large number of restriction endonucleases among other proteins (Pingoud et al. *Cell Mol Life Sci.* 62(6):685-707 2005). Numerous high-resolution protein structures and mutagenesis experiments reveal the principles of and amino acid requirements for this endonuclease domain activity.

In instances in which the eukaryotic non-LTR RT protein is a *Bombyx mori* R2 RT protein, the mutation that abolishes endonuclease function may be a substitution mutation at amino acid residue D996, D1009, or K1026 of full-length *Bombyx mori* R2 RT protein having an amino acid sequence of SEQ ID NO: 1. In some instances, the substitution mutation is at amino acid residue D996. In some instances, amino acid residue D996 is substituted by any amino acid, except Glu (E). Therefore, in some instances, the amino acid residue D996 is substituted by an Ala (A), Ile (I), Leu (L), Met (M), Phe (F), Val (V), Pro (P), Gly (G), Arg (R), Lys (K), Gln (Q), Asn (N), His (H), Ser (S), Thr (T), Tyr (Y), Cys (C), Trp (W), or Tyr (Y). In some instances, the substitution mutation is a D996A mutation. In some instances, the substitution mutation is at amino acid residue D1009. In some instances, amino acid residue D1009 is substituted by any amino acid, except Glu (E). In some instances, the amino acid residue D1009 is substituted by Ala (A), Ile (I), Leu (L), Met (M), Phe (F), Val (V), Pro (P), Gly (G), Arg (R), Lys (K), Gln (Q), Asn (N), His (H), Ser (S), Thr (T), Tyr (Y), Cys (C), Trp (W), or Tyr (Y). In some instances, the substitution mutation is a D1 009A mutation. In some instances, the substitution mutation is at amino acid residue K1026. In some instances, the substitution mutation is a K1026A, K1026D, or K1026E mutation. In some instances, the substitution mutation is a K1 026A mutation. In some instances, mutations that abolishes endonuclease function are substitution mutations at amino acid residues K1026 and K1029. In some instances, the substitution mutations are K1026A and K1 029A mutations.

Stabilizer Proteins

The isolated eukaryotic non-LTR RT proteins may include one or more stabilizer proteins. A stabilizer protein that forms part of a non-LTR RT protein functions to increase the overall stability and/or proper structure of the modified non-LTR RT protein. Stability includes the ability of the protein to retain its conformation and activity.

Attaching a stabilizer protein to the eukaryotic non-LTR RT proteins can provide one or more advantages. A modified eukaryotic non-LTR RT protein including a stabilizer protein can, for example, have increased stability at elevated temperatures, increased solubility, increased protein expression, improved protein folding, and/or short-term or long-term storage with retained specific activity. In some instances, a modified eukaryotic non-LTR RT protein of the invention including a stabilizer protein may have one or more of the properties listed above. For example, the modified eukaryotic non-LTR RT protein may have increased thermostability and/or increased solubility. In another example, the modified eukaryotic non-LTR RT protein may have increased protein expression and exhibit improved protein folding.

Inclusion of a linker peptide between the stabilizer protein and the eukaryotic non-LTR RT protein can further enhance these advantages. However, the eukaryotic non-LTR RT protein and the stabilizer protein could alternatively be directly fused to one another with minimal if any linker. Accordingly, the stabilizer protein can be positioned N-terminal or C-terminal to the eukaryotic non-LTR RT protein, with or without an intervening linker peptide.

In some instances, a stabilizer protein is connected to a eukaryotic non-LTR RT protein of the invention for expression of the fusion protein in bacterial cells. In some instances, the stabilizer protein is maltose binding protein (MBP), or a variant thereof. Other examples of stabilizer proteins include Small Ubiquitin-like Modifier (SUMO) or Protein A domain(s), or variants thereof.

In any of the above instances in which the isolated eukaryotic non-LTR RT protein includes one or more stabilizer proteins, the improved/increased overall stability of the protein is reflected by an increase in recombinant protein solubility upon cellular expression, purification yield, fraction of protein that is monomeric, half-life of the enzyme in biochemical reactions, and/or retention of activity upon storage at room temperature or 4, −20, and/or −80° C.

Purification Tags

The isolated eukaryotic non-LTR RT proteins may, in addition to one or more stabilizer proteins, include one or more purification tags.

Inclusion of a linker peptide between the purification tag and the eukaryotic non-LTR RT protein can be desirable. However, the eukaryotic non-LTR RT protein and the purification tag could alternatively be directly fused to one another. Accordingly, the purification tag can be positioned N-terminal or C-terminal to the eukaryotic non-LTR RT protein, with or without an intervening linker peptide.

In some instances, a purification tag is connected to a eukaryotic non-LTR RT protein of the invention for expression and subsequent purification of the fusion protein from bacterial cells. In some instances, particularly for purification from bacterial cells, the purification tag is a histidine tag, such as a 6×-His tag. In some instances, the histidine tag (e.g., 6×-His tag) is positioned C-terminal to the eukaryotic non-LTR RT protein, with or without an intervening linker peptide. In some instances, the histidine tag (e.g., 6×-His tag) is positioned C-terminal to the eukaryotic non-LTR RT protein, with or without an intervening linker peptide, and a stabilizer protein (e.g., MBP) is positioned N-terminal to the eukaryotic non-LTR RT protein, with or without an intervening linker peptide. In some instances, the histidine tag (e.g., 6×-His tag) is positioned C-terminal to the eukaryotic non-LTR RT protein, with an intervening linker peptide, and a stabilizer protein (e.g., MBP) is positioned N-terminal to the eukaryotic non-LTR RT protein, with or without an intervening linker peptide.

In some instances, a purification tag is connected to a eukaryotic non-LTR RT protein of the invention for expression and subsequent purification of the fusion protein from eukaryotic cells. In some instances, particularly for purification from eukaryotic cells, the purification tag is a Protein A tag or a FLAG peptide tag. In some instances, the purification tag is a tandem Protein A tag. In some instances, the purification tag is a 3×-FLAG peptide tag. In some instances, the purification tag (e.g., Protein A or FLAG peptide tag) is positioned C-terminal to the eukaryotic non-LTR RT protein, with or without an intervening linker peptide, and the eukaryotic non-LTR RT protein does not include a separate stabilizer protein. In other instances, the purification tag (e.g., Protein A or FLAG peptide tag) is positioned N-terminal to the eukaryotic non-LTR RT protein, with or without an intervening linker peptide, and the eukaryotic non-LTR RT protein does not include a separate stabilizer protein. In some instances, the purification tag (e.g., Protein A or FLAG peptide tag) is positioned C-terminal to the eukaryotic non-LTR RT protein, with or without an intervening linker peptide, and the eukaryotic non-LTR RT protein does include a separate stabilizer protein. In other instances, the purification tag (e.g., Protein A or FLAG peptide tag) is positioned N-terminal to the eukaryotic non-LTR RT protein, with or without an intervening linker peptide, and the eukaryotic non-LTR RT protein does include a separate stabilizer protein.

Other examples of purification tags include the Twin-Strep-tag, myc peptide tag, acyl carrier protein tag, and others, or variants thereof.

Linker Peptides

In instances in which a linker peptide is used to connect a stabilizer protein and/or purification tag with the eukaryotic non-LTR RT protein, the linker(s) can be two or more amino acids in length. The linker can consist of neutral, polar, or nonpolar amino acids. The linker can be, for example, 2 to 100 amino acids in length, such as between 2 and 50 amino acids in length, for example, 3, 5, 10, 15, 20, 25, 30, 35, 40, 45, or 50 amino acids in length. In some instances, a linker is a region that promotes folding of the adjacent protein(s) or polypeptide(s), as described in Smyth et al. Protein Science. 12: 1313-1322, 2003.

A linker can be cleavable, for example, by enzymatic or chemical cleavage that may be self-mediated or mediated by a physically separate agent. Cleavage sites in amino acid sequences and enzymes and chemicals that cleave at such sites are well known. For example, enzymatic cleavage of a linker may involve the use of an endopeptidase such as, for example, furin, urokinase, Lys-C, Asp-N, Arg-C, V8, Glu-C, chymotrypsin, trypsin, pepsin, papain, thrombin, tissue plasminogen activator (tPa), genenase, Factor Xa, TEV (tobacco etch virus) cysteine protease, the SUMO protease Ulp1, enterokinase, HRV C3 (human rhinovirus C3 protease), kininogenase, as well as subtilisin-like proprotein convertases (e.g., furin (PC1), PC2, or PC3) or N-arginine dibasic convertase.

Chemical cleavage may involve a disulfide cleavable by reducing agent or a self-cleaving protein motif.

Methods for Extension of a Polynucleotide 3' End in a Manner not Determined by Template Copying Polynucleotide 3' extension by nucleotide addition without the constraints of template copying (also referred to as polynucleotide tailing) is a widely useful method for covalently appending molecular tags. Enzymes with nucleotide transferase activity include terminal deoxynucleotidyl transferase (TdT), specialized for tailing single-stranded DNA substrates with semi-random deoxynucleotides, and RNA polymerases specialized for tailing single-stranded RNA substrates with homopolymer tails, predominantly A or U. With the discovery of a terminal transferase activity of non-retroviral RT enzymes stimulated by the presence of $Mn^{2+}$, it becomes possible to tail RNA and DNA of single- or double-stranded composition using NTP, dNTP, or other nucleotide analog substrates, greatly broadening the capacity to covalently append molecular tags to a polynucleotide 3' end.

Provided herein are methods of extending the 3' end of a single-stranded or partially single-stranded nucleic acid by at least one nucleotide, the method including contacting the single-stranded or partially single-stranded nucleic acid with a non-retroviral RT protein having nucleotide polymerase activity in a buffer comprising manganese ions. In some instances, the single-stranded or partially single-stranded nucleic acid is DNA. In some instances, the contacting is carried out in the absence of a terminal deoxynucleotidyl transferase (TdT), a retroviral RT protein, or any other non-RT protein. In some instances, the single-stranded or partially single-stranded nucleic acid is RNA. In some instances, the contacting is carried out in the absence of an RNA ligase or poly-adenosine RNA polymerase, poly-uridine RNA polymerase, or any other non-RT protein.

Also provided are methods of extending the 3' ends of an A-form nucleic acid duplex by at least one nucleotide, the method including contacting the A-form nucleic acid duplex with a non-retroviral RT protein having nucleotide polymerase activity in a buffer comprising manganese ions. In some instances, the A-form nucleic acid duplex is an RNA-RNA nucleic acid duplex, a partially RNA-RNA nucleic acid duplex, or a modified form thereof. In some instances, one or both ends of the RNA-RNA nucleic acid duplex, partially RNA-RNA nucleic acid duplex, or modified form thereof, are blunt-ended or comprise a one-nucleotide or other short 3' overhang. In some instances, the A-form nucleic acid duplex is an RNA-DNA nucleic acid duplex, a partially RNA-DNA nucleic acid duplex, or a modified form thereof. In some instances, one or both ends of RNA-DNA nucleic acid duplex, partially RNA-DNA nucleic acid duplex, or modified form thereof, are blunt-ended or comprise a one-nucleotide or other short 3' overhang.

In some instances, the non-retroviral RT terminal transferase activity can be used to tag nucleic acid molecules with moieties that comprise a signal for binding or covalent attachment to a ligand, surface, or other molecule. This method enables attachment specificities including, but not restricted to, a purification resin, microarray plate, or flow cell. Further, this method enables binding specificities including, but not restricted to, enzymes that recognize the appended moiety and other nucleic acids that will be increased in local concentration by non-covalent binding.

In some instances, the non-retroviral RT terminal transferase activity can be used to tag nucleic acid molecules with a detection signal, for uses including, but not restricted to, generating a hybridization probe for microarray profiling or a method of nucleic acid quantification. In some instances, the non-retroviral RT terminal transferase activity can be used to alter the nature of the polynucleotide 3' end. For example, the 3' end may be blocked from recognition by an exonuclease, blocked from acting as a primer for template-dependent synthesis, or activated for chemical concatemerization or enzymatic ligation. The 3' end may confer favorable properties of polynucleotide solubility, stability, or permeability (e.g., increased half-life in plasma, increased cell penetration, or targeting to a cell surface receptor molecule).

In some instances, the non-retroviral RT terminal transferase activity can be used for oligonucleotide synthesis by cycles of addition and unblocking of reversibly chain-terminating nucleotide analogs. In some instances, the non-retroviral RT terminal transferase activity can be used to add distinct unique molecular identifier sequences (UMI) to each molecule in a pool of polynucleotides, or to add distinct bar codes to separate pools of polynucleotides. In some instances, the 3' tailing reaction can create a spacer that ultimately separates the tailed polynucleotide sequences after concatemerization. In some instances, the 3' tailing will be a reversible block to additional 3' extension by non-templated or templated extension. In some instances, the reversible block will be used for serial rounds of differently combinatorial bar-coding, for example, for spatial transcriptomics (Moor et al. *Curr Opin Biotechnol.* 46:126-133, 2017). In some instances, the non-retroviral RT protein will be used to append a non-native nucleotide such as iso-dG or iso-dC, to generate a 3' end that will base-pair with a specific other non-native nucleotide. In this manner, template molecules tailed for example with iso-dG could pair with a cognate single-nucleotide overhang distinct from all native (for example, iso-dG, pairs with iso-dC but not A, C, G, T or U).

In some instances, the non-retroviral RT terminal transferase activity can be used to extend a relatively homogenous population of molecules, such as a synthetic oligonucleotide. In some instances, the non-retroviral RT terminal transferase activity can be used to extend a mixed population of molecules, such as in a patient sample of cell-free nucleic acids obtained by liquid biopsy.

In some instances, the polynucleotides can be modified prior to their tailing by non-retroviral RT terminal transferase activity. For example, if the 3' group is not OH, repair enzymes such as T4 polynucleotide kinase (PNK) may be used to generate a 3' OH from 3' monophosphate or 2'3' cyclic monophosphate. Polynucleotides may or may not be denatured to remove secondary structure, and may or may not be subject to depletion or enrichment for particular nucleic acids or other components.

In some instances, the non-retroviral RT terminal transferase activity can be used to tail nucleic acids as a step to generating a sample for sequencing. In some instances, the non-retroviral RT terminal transferase activity can be used to tail single-stranded RNA or DNA or a mixture of those for sequencing using the Illumina platform. In some instances, the non-retroviral RT terminal transferase activity can be used to tail RNA or DNA or a mixture of those for sequencing using the Pacific Biosciences platform, or others.

In some instances, the non-retroviral RT protein is a eukaryotic non-LTR RT protein or a prokaryotic or organellar intron RT protein. In some instances, the non-retroviral RT protein is a eukaryotic non-LTR RT protein. In some instances, the non-retroviral RT protein is a eukaryotic non-LTR RT protein of an aspect of the invention described herein. In some instances, the eukaryotic non-LTR RT protein is an R2 RT protein. In some instances, the R2 RT protein is a *Bombyx mori* R2 RT protein. In some instances, the non-retroviral RT protein is a prokaryotic or organellar intron RT protein. In some instances, the prokaryotic or organellar intron RT is a *Eubacterium* rectale group II intron RT protein.

In some instances, the non-retroviral RT terminal transferase activity can be performed by variously modified RT proteins. For example, enzyme mutations can broaden or narrow the range of nucleotide or nucleotide-like substrates and the divalent metal ion requirement specificity. Also, enzyme mutations can broaden or narrow the range of polynucleotide substrates. In addition, the non-retroviral RT protein may be covalently or non-covalently fused to protein or other modules for binding desired polynucleotide substrates. Further, the non-retroviral RT protein may be engineered or selected to have higher or lower error rate, processivity, synthesis rate, temperature range of activity, compatibility with other compounds present in reaction mixtures, stability, solubility, or other relevant property for use.

In some instances, non-retroviral RT reactions containing $Mn^{2+}$ can be used to alter the specificity of template-dependent cDNA synthesis as well as allow non-templated synthesis, for example, eliminating the uncontrolled single-stranded RNA priming on single-stranded RNA templates (Luan, Eickbush *Mol Cell Bio.* 1996 16(9): 4726-34).

In some instances, the buffer comprises one or more ribonucleoside triphosphates (NTPs), deoxyribonucleoside triphosphates (dNTPs), or dideoxyribonucleoside triphosphates (ddNTPs), or nucleotide analogs thereof. In some instances, the contacting is carried out at a temperature of between about 4° C. and about 50° C. In some instances, the contacting is carried out at a temperature of about 37° C.

Because the previously unanticipated terminal transferase activity of non-retroviral RTs described herein is a shared feature of eukaryotic and prokaryotic non-retroviral RTs, other non-retroviral RTs would be expected to demonstrate this type of activity and could substitute for the RTs used in applications described here. The large diversity of non-retroviral RTs across bacterial, archaeal, and eukaryotic organellar and nuclear genomes provides a functional diversity of terminal transferase specificities, as judged from the differences as well as similarities described herein between prokaryotic intron RT proteins and eukaryotic non-LTR retroelement RT proteins.

Methods for Continuous cDNA Synthesis Across Discontinuous Templates by Principles of Ordered Template Relay (OTR)

The most efficient synthesis of a cDNA library would add, using a single tube, a single reaction, a convenient reaction temperature, and entirely storage-stable components, all of the 5' and 3' adaptor elements and other sample preparation necessary to accomplish (i) quantifying, amplifying, circularizing, and/or tagging molecules according to the platform requirements for input library (for example Illumina, Pacific Biosciences, Nanopore, BGI, and others); (ii) indexing different libraries combined into a sequencing run, for example using bar codes, if that is part of the platform technology; (iii) denaturing the input library according to any platform requirements; and (iv) providing base-pairing sites for the primers that will initiate sequencing by synthesis, when that is part of the platform technology. In a typical library preparation for the market-dominant Illumina platform, for example, cDNA sequences must be flanked adaptors with three component segments: 5'-P5, index(i)5, Read (R)1-3' or 5'-P7, i7, R2-3'. These two composite adaptor sequences must be present on opposite sides of the cDNA. Furthermore, because PCR is typically used to add the index, P5, and P7 modules of sequence, libraries must be denatured prior to flow cell loading then diluted about 100-fold to neutralize the denaturation, which results in the loss of typically ~80-90% of the library produced due to the restricted loading volume of the flow cell. Also, because the adaptor sequences used for NGS are evolving with innovation, a method for library production that is readily amenable to changes in the module sequences is essential for general utility. Methods described herein provide all of these improvements.

In some instances, template relay is restricted in specificity by specific combinations of primer and template sequences and other features. These combinations may promote the accuracy or efficiency of production of intended cDNA library products and/or reduce the production or alter the nature of non-desired side-reaction products such as result from promiscuous priming and template copying within the reaction. "Template jumping" allows near-comprehensive or relatively unbiased use of templates in a sequence mixture for cDNA synthesis, and, in conditions of serial template copying, also allows different numbers of templates to be represented in a cDNA concatemer. Methods described herein provide improvements of selective template copying and control of the number of copied templates in a cDNA product.

In one aspect, the invention provides methods of preparing a complementary DNA (cDNA) molecule comprising: (a) providing a primer duplex comprising a primer strand and a non-extended strand, wherein the 3' end of the primer strand comprises a +1 pyrimidine nucleotide overhang; (b) providing an RNA template comprising a purine nucleotide at its 3' end; and (c) contacting the primer duplex and the RNA template with a RT in a buffer comprising magnesium ions and one or more dNTPs or analogs thereof, wherein the contacting is carried out under conditions effective for production of a cDNA molecule that is substantially complementary to the RNA template.

Accordingly, in some instances, primer with a +1T and/or +1C 3' overhang is combined with templates containing 3' cognate purine(s), for example A and/or G attached to a nucleotide sugar moiety with or without various OH groups.

In some instances, primer strand is a DNA primer strand. In some instances, the primer strand comprises a 5' overhang. In some instances, the 5' end of the primer strand or internal site comprises a modification. In some instances, the modification allows for immobilization or purification of the primer strand or the primer duplex. In some instances, the modification is a linkage to biotin. In some instances, the primer strand is a 5' adapter sequence. In some instances, the non-extended strand comprises DNA, RNA, hybrid DNA and RNA, or a modified form thereof. In some instances, the 3' end of the non-extended strand comprises a modification. In some instances, the modification blocks 3' extension. In some instances, the modification is a 3' C3 spacer or a 3' monophosphate. In some instances, the RNA template is prepared by a method described in Section IV above. The RNA template may include a purine dNTP, NTP, ddNTP, or nucleotide analog at its 3' end. Similarly, in some instances, the primer duplex is prepared by a method described in Section IV above. In some instances, the 5' end of the RNA template comprises a modification. In some instances, the modification is an irreversible modification. In some instances, the irreversible modification is a 5' C6 spacer or biotin. In some instances, the modification is a reversible modification. In some instances, the reversible modification is a 5' adenylylation.

In some instances, the contacting is carried out in the presence of a second template, wherein the second template comprises a pyrimidine nucleotide at its 3' end. The second template with a 3' pyrimidine base is preferred as a template only after cDNA synthesis across the 3' purine template. In some instances, the primer has a modified+1 pyrimidine, such as iso-dC, and the first template pool has 3' iso-dG. In some instances, the reaction is supplemented with a purine nucleotide analog that will be used for non-templated extension of the first-template cDNA, along with a second template with 3' purine that can base-pair to the forementioned purine nucleotide analog.

In some instances, the second template comprises DNA, RNA, hybrid DNA and RNA, or a modified form thereof. In some instances, the second template comprises a pyrimidine ribonucleotide at its 3' end. In some instances, the second template is a complement of a 3' adapter sequence. In some instances, the contacting is carried out under conditions effective for production of a cDNA molecule that comprises the 5' adapter sequence, a sequence substantially complementary to the RNA template, and the 3' adapter sequence. In some instances, the 5' end of the second template comprises a modification. In some instances, the modification is an irreversible modification. In some instances, the irreversible modification is a 5' C6 spacer or biotin. In some instances, the modification is a reversible modification. In some instances, the reversible modification is a 5' adenylylation.

By the methods described herein, the execution of ordered template relay allows 5' adaptor, cDNA template, and 3' adaptor template, for example, to be combined in a single tube, supplemented with favorable ions and dNTPs and other buffer components, and introduced to a non-retroviral RT protein capable of continuous cDNA synthesis across discontinuous templates.

In some instances, the initial primer and second template are comprised of adaptor sequences. In some instances, those adaptor sequences are necessary module(s) for NGS. In some instances, the NGS adaptor sequences are for the Illumina NGS platform. In some instances, the module(s) for 5'-P5, index(i)5, Read(R)1-3' are represented on the cDNA 5' adaptor and the 5'-P7, i7, R2-3' modules are represented on the second template. In some instances, the representation is reversed. In some instances, the NGS adaptor sequence(s) are for the Pacific Biosciences or other platform. In some instances, the adaptor sequences are for cDNA use for PCR. In some instances, the adaptor sequences are for cDNA use for microarray hybridization or other hybridization application. In some instances, the adaptors contain moieties that enable cDNA library binding or attachment to a matrix, surface, molecule, or other compound. In some instances, the adaptors allow for amplification of the cDNA by T7 or other RNA polymerase.

In some instances, the adaptors contain moieties that enable cDNA library binding or attachment to a matrix, surface, molecule, or other compound. In some instances, adaptors contain moieties that alter the nature of the cDNA library 5' end. For example, the 5' end may be blocked from recognition by an exonuclease, blocked from phosphorylation or dephosphorylation, or activated for chemical concatemerization or enzymatic ligation. The 5' end may confer favorable properties of polynucleotide solubility, stability, or permeability, for example increased half-life in plasma, increased cell penetration, or targeting to a cell surface receptor molecule. In one instance, a sequencing-ready library is prepared within about 2-3 hours. Rapid preparation time compared to currently favored protocols reduces the necessary time lag between sample collection for disease diagnosis or non-invasive pre-natal testing (NIPT) and use of the obtained sequence for therapy, surgery, and/or other choices. In one instance, a sequencing-ready library is prepared in a more reproducible and less technically demanding manner by using a single container rather than container transfers and/or eliminating sample partitioning by introducing a matrix or other surface for fractionation of product molecules. Furthermore, it would be ideal to have an option to produce libraries either without PCR, for example to prevent representation skew from PCR bias, or with PCR, when necessary due to low input or indexing considerations. Methods described herein provide all of these improvements.

In some instances, the non-retroviral RT is a non-LTR RT protein with serial template relay activity. In some instances, the non-retroviral RT is an R2-like RT protein. In some instances, the non-retroviral RT protein is a modified R2 RT protein from *Bombxy mori*, such as a *Bombxy mori* R2 RT protein described herein, for example, in Section III above. In some instances, other non-retroviral RT proteins discovered or engineered to have serial template relay activity can substitute for the R2 RT protein in template relay reactions.

In some instances, ordered template relay will be performed by variously modified non-retroviral RT proteins. For example, enzyme mutations can broaden or narrow the range of nucleotide or nucleotide-like substrates. Also, enzyme mutations can broaden or narrow the range of polynucleotide substrates. In addition, the non-retroviral RT protein may be covalently or non-covalently fused to protein or other modules for binding desired polynucleotide substrates. Further, the non-retroviral RT protein may be engineered or selected to have higher or lower error rate, processivity, synthesis rate, temperature range of activity, compatibility with other compounds present in reaction mixtures, stability, solubility, or other relevant property for use.

Because the previously unanticipated terminal transferase activity of non-retroviral RTs described herein is a shared feature of eukaryotic and prokaryotic non-retroviral RTs, other non-retroviral RTs would be expected to demonstrate this type of activity and could substitute for the RTs used in applications described here. The large diversity of non-retroviral RTs across bacterial, archaeal, and eukaryotic organellar and nuclear genomes provides a functional diversity of terminal transferase specificities, as judged from the differences as well as similarities described herein between prokaryotic intron RT and eukaryotic non-LTR retroelement RT. In some instances, non-retroviral RT enzyme fusions to other proteins or compounds can tune the affinity and specificity of binding and reaction properties, for example by promoting binding of a category of primer and/or template molecules. In some instances, different non-retroviral RT proteins can be combined or used individually in different stages of cDNA library preparation.

In some instances, polynucleotides can be modified prior to their use for template relay. For example, if the 3' group is not OH, repair enzymes such as T4 polynucleotide kinase (PNK) may be used to generate a 3' OH from 3' monophosphate or 2'3' cyclic monophosphate. Polynucleotides may or may not be denatured to remove secondary structure, and may or may not be subject to depletion or enrichment for particular nucleic acids or other components. Polynucleotides may be subject to fragmentation or ligation, in the same reaction container or separately.

In some instances, polynucleotides are from cell-free patient samples, tissue biopsies, microbiome collection, salt or fresh water samples, forensic material, single live or fixed cells, blood plasma or enriched exosomes, fragmented genomic DNA, ancient DNA, or other biological material. In some instances, the process of cDNA library preparation is automated.

In some instances, template relay specificity will be influenced by suppression of non-productive, cDNA intermediate tailing, for example with dNTP concentration changes or dNTP analogs. In addition, efficiency of the second step of template relay may be increased by increasing the local concentration of the second template relative to the intermediate cDNA product from first-template copying. In some instances, this increase in local concentration may be mediated by surface immobilization or droplet technologies among others.

In some instances, the contacting is carried out at a temperature of between about 4° C. and about 50° C. In some instances, the contacting is carried out at a temperature of about 37° C.

In some instances, as noted above, the method is carried out in a single container or vessel.

Articles of Manufacture or Kits

Another aspect of the invention is an article of manufacture containing one or more isolated eukaryotic non-long terminal repeat reverse transcriptase (non-LTR RT) proteins described herein and materials useful for the practice of nucleic acid detection, quantification, or sequencing, and, in particular, materials useful for the accomplishing ordered and continuous complementary DNA (cDNA) synthesis across non-continuous templates and/or non-native terminal transferase activities of non-retroviral RT proteins.

The practice of nucleic acid detection, quantification, or sequencing often require practitioners skilled in the art, due to technical complexity. A goal for bringing the precision of molecular diagnostics to the forefront of pathogen, health status, and cancer detection and therapy is the reproducible, largely hands-off acquisition of biomarker profiles. Nucleic acids offer this opportunity, if their content could be read comprehensively and with limited bias. The inventions described herein are enabling for research and clinical applications that require reproducible, standard operating procedure (SOP) protocols for readout of nucleic acid information. In some aspects, such enablement is provided in the form of a kit.

The article of manufacture may include a container and a label or package insert on or associated with the container. Suitable containers include, for example, bottles, vials, syringes, etc. The containers may be formed from a variety of materials, such as glass or plastic. In some instances, the container holds a composition, such as one or more isolated eukaryotic non-LTR RT proteins, that are useful or required for carrying out the methods of nucleic acid labeling using the terminal transferase activity of non-retroviral RTs and/or nucleic acid sequencing using ordered template replay by non-retroviral RTs.

In some instances, nucleic acid labeling using the terminal transferase activity of non-retroviral RTs will generate a probe for detection of pathogen or mutation. In some instances, this practice will detect a signal of interest in cell-free nucleic acid liquid biopsy, tumor biopsy with or without fixative, infected tissue, environmental sample, dried blood spot, microbiome material, or plasma. In some instances, such enablement is provided in the form of a kit.

In some instances, nucleic acid sequencing using ordered template replay by non-retroviral RTs will generate a profile of nucleic acids informative for the condition of cells or for the presence of a normal or aberrant molecule of interest. In some instances, this sequencing will have single-cell resolution. In some instances, such enablement is provided in the form of a kit.

The articles of manufacture may further include other materials considered from a commercial and user standpoint, including other buffers, diluents, and other reagents useful or required, for example, for nucleic acid detection and/or labeling.

Kits are also provided that contain one or more isolated eukaryotic non-LTR RT proteins or other reagents (e.g., primers) useful for various purposes, e.g., the practice of nucleic acid detection, quantification, or sequencing. As with the article of manufacture, the kit comprises a container and a label or package insert on or associated with the container. The container holds a composition comprising at least one eukaryotic non-LTR RT protein of the invention, or, alternatively, at least one reagent useful for various purposes, e.g., the practice of nucleic acid detection, quantification, or sequencing. Additional containers may be included that contain, e.g., diluents and buffers. The label or package insert may provide a description of the composition as well as instructions for the intended in vitro or diagnostic use.

The specification is considered to be sufficient to enable one skilled in the art to practice the invention. Various modifications of the invention in addition to those shown and described herein will become apparent to those skilled in the art from the foregoing description and fall within the scope of the appended claims.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: High-Yield Production of a Highly Purified RT with Processive Template Relay Retroviral RTs were discovered as RNA-templated DNA synthesis enzymes about 50 years ago, and subsequent decades have witnessed a constant flurry of improvements to their utility for molecular applications including RT-PCR and RNA-seq (Coffin J M, Fan H Annu Rev Virol. 2016 3(1):29-51). Retroviral RTs evolved relatively recently, in animal hosts, with loss of many of the nucleic acid binding properties of the cellular RTs from which they evolved. In particular, retroviral RTs rely on binding to primer-template duplex to recognize a template, whereas typical eukaryotic cellular retroelement RTs initiate cDNA synthesis without homology between their template and a physically separate duplex primer (Eickbush T H, Jamburuthugoda V K_Virus Res. 2008 134(1-2):221-34). In this manner, eukaryotic retroelement RTs differ from the typical prokaryotic and organellar RTs encoded by mobile self-splicing introns, which copy their templates after template reverse-splicing into DNA (Lambowitz A M Zimmerly S Cold Spring Harb Perspect Biol. 2011 3(8):a003616). Eukaryotic retroelement RTs have been challenging to purify free of associated nucleic acids, such that many activity conclusions about "purified" retroelement RT reflected activity of an RNP, not an RT protein devoid of pre-bound RNA (Christensen S M, Ye J, Eickbush T H Proc Natl Acad Sci USA. 2006 103(47): 17602-7). Nonetheless, retroelement RT biological and biochemical activities could be uniquely useful tools in developing research and clinical applications, if the enzyme could be produced at high yield in contaminant-free, storage-stable form.

In this example, RTs encoded by the genomes of prokaryotic and eukaryotic cells were screened for (a) robust expression, (b) high-yield purification free of nucleic acids, (c) cDNA synthesis activity on an annealed primer-template substrate such as used in a retroviral RT assay, and (d) template "jumping" activity allowing processive copying of multiple physically separate templates to generate a single covalently continuous cDNA.

Methods

RT polypeptides were expressed with N-terminal maltose binding protein (MBP) tag containing an MBP sequence variant (Smyth et al. Protein Sci. 12(7):1313-22, 2003) and a C-terminal 6x-Histidine tag. Examples of expressed tagged RT polypeptides described herein include tagged full-length R2 RT from Bombyx mori (SEQ ID NO: 5), tagged ΔN69 R2 RT from Bombyx mori (SEQ ID NO: 6; also referred to as NBomoC), tagged ΔN274 R2 RT from Bombyx mori (SEQ ID NO: 7; also referred to as BomoC), tagged ΔN274 R2 RT from Bombyx mori with a C-terminal truncation to remove the endonuclease domain (SEQ ID NO: 12; also referred to as Bomo), tagged ΔN274 R2 RT from Bombyx mori having a D996A mutation that abolishes endonuclease function (SEQ ID NO: 3; also referred to as BomoC(ed)), tagged ΔN69 R2 RT from Bombyx mori having a D996A mutation that abolishes endonuclease function (SEQ ID NO: 13; also referred to as NBomoC(ed)), and tagged full-length RT from the bacterium Eubacterium rectale (SEQ ID NO: 8; also referred to as Eure or EuRe).

The enzyme purification method detailed here is scaled for a 2 L bacterial culture. Induce protein expression in 2 L Rosetta2(DE3)pLysS cells grown in 2YT medium when they reach OD600 =0.9. Use 0.5 mM IPTG shaking at 16° C. overnight. After harvesting the cell pellet, resuspend in 20 mM Tris-HCl pH 7.4, 1 M NaCl, 10% glycerol, 1 mM $MgCl_2$, DNase I (Roche 04716728001, 5 microgram/mL), RNase A (Sigma R6513, 5 microgram/mL), and protease inhibitors. Lyse cells by sonication for 3.5 min (10 s on, 10 s off on ice). Remove insoluble material by centrifugation (Sorval SS34 rotor, 15,000 rpm for 30 min, 4° C.).

Perform nickel affinity chromatography by automated program on 5 ml HisTrap FF Crude: equilibrate in Buffer A, load sample, wash with 5 column volumes (CV) wash buffer, elute with 5 CV elution buffer. Buffer A: 20 mM Tris-HCl pH 7.4, 1 M NaCl, 10% glycerol, 1 mM beta-mercaptoethanol. Wash Buffer: 20 mM Tris-HCl pH 7.4, 1 M KCl, 20 mM imidazole, 10% glycerol, 1 mM beta-mercaptoethanol. Elution Buffer: 20 mM Tris-HCl pH 7.4, 1 M KCl, 400 mM imidazole, 10% glycerol, 1 mM beta-mercaptoethanol.

Pool elutions according to absorbance, desalt to 400 mM KCl using an FLPC HiPrep 26/10, and apply to 5 ml HiTrap Heparin HP. Equilibrate column, load sample, and wash in 20% Heparin Buffer B. First run of heparin column was step-eluted to 100% Heparin Buffer B. The peak was pooled and diluted back to approximately 400 mM KCl (about 2-fold dilution). Second run was parallel to first except for elution with a gradient of 20-100% Buffer B over 15 CV until protein eluted. Heparin Buffer A: 25 mM HEPES-KOH pH 7.5, 10% glycerol, 1 mM DTT. Heparin Buffer B: 25 mM HEPES-KOH pH 7.5, 2 M KCl, 10% glycerol, 1 mM DTT.

Pooled heparin column elutions were further resolved by size exclusion chromatography using HiPrep 16/60 Sephacryl S-200HR by automated program. Size-exclusion column buffer: 25 mM HEPES-KOH pH 7.5, 0.8 M KCl, 10% glycerol, 1 mM DTT. The monomer protein peak was pooled (typical concentration 7-8 mg/mL), supplemented to 2-5 mM DTT, aliquoted, frozen by liquid nitrogen, and stored at −80° C. with no evident loss of activity over at least a year. Working stock is diluted with the same buffer adjusted to 50% glycercol and stored at −20° C. at 1.25 mg/mL=about 10 micromolar. No evident loss of activity occurred over the maximal storage time tested (about 4-6 months).

Typical assays for RT primer-extension activity used chemically synthesized DNA primer annealed to an RNA template purified after T7 RNA polymerase transcription, which together generated a template 5' overhang substrate for primer extension. Reaction conditions were typically 20 mM Tris-HCl pH 7.5, 150 mM KCl, 2 mM $MgCl_2$, 10% glycerol with incubations at room temperature or 37° C. Nucleic acids were typically used at final concentrations ranging from 20 to 200 nM. RT protein was typically added at about 0.1-1.0 micromolar. Nucleotide concentrations varied (2.5 to 500 micromolar). Typically products were detected by SYBR Gold staining and imaging on a Typhoon Trio after denaturing PAGE.

Typical assays for cDNA synthesis by processive use of multiple template molecules (i.e., serial template copying) used a DNA primer that was annealed in full or part to a second strand, usually RNA, to generate a primer 3' end that was blunt duplex or a short 3' overhang of defined sequence. Templates included chemically synthesized RNA or DNA oligonucleotides and/or RNAs purified after T7 RNA polymerase transcription; templates were also isolated from biological sources. Reaction conditions were typically 20 mM Tris-HCl pH 7.5, 150 mM KCl, 2 mM $MgCl_2$, 10% glycerol with incubations at room temperature or 37° C. Nucleic acids were typically used at final concentrations of 20-90 nM pre-annealed primer duplex, 20-200 nM template, and if present 20-90 nM of a second, cDNA 3' adaptor template. RT protein was typically added at about 0.1-1.0 micromolar.

Results

The tagged full-length eukaryotic RT protein (SEQ ID NO: 5) and ΔN69Bomo RT protein (SEQ ID NO: 6) could not be purified at high yield and contaminant-free. In comparison, tagged N-terminally truncated BomoC, lacking all R2 RT sequence prior to and including the sequence-specific DNA binding domains (SEQ ID NOs: 3 and 7)(FIG. 1A), could be produced at even higher yield than intron RTs. For purified MBP- and 6×Histidine-tagged proteins eluted from the gel filtration column at their predicted monomer molecular weights (FIG. 1B), the ratios of absorbance at 260 and 280 nM indicate pure protein without contaminating nucleic acid (FIG. 1C), which was confirmed by attempts at nucleic acid detection.

Figure 2:
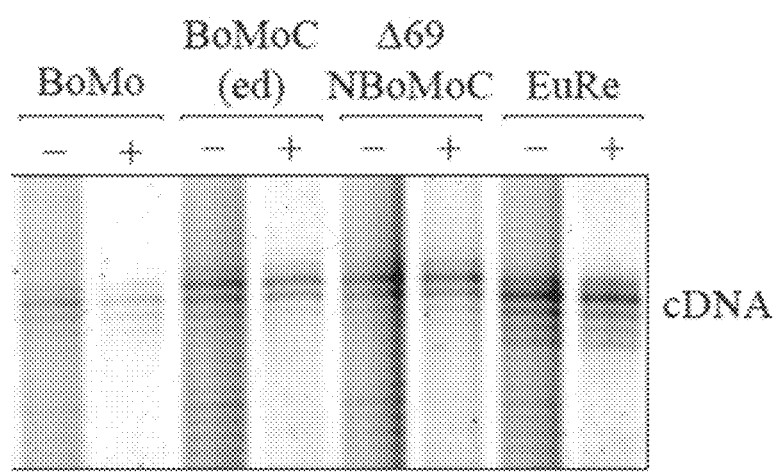
FIG. 2. Results of a primer-extension assay for MBP- and 6x-Histidine-tagged, purified RT proteins. DNA primer was annealed to a complementary region within a purified RNA template and incubated with the indicated enzyme and all 4 dNTPs. The RT proteins were used at the same molar concentration. Lane +/−indicates presence or absence of RNase A after product denaturation, before denaturing PAGE and SYBR Gold staining. The expected cDNA products from complete extension to the template 5' end are indicated, with the size range resulting from non-templated nucleotide (nt) addition to the template-paired cDNA 3' end.

The purified RT proteins could catalyze the extension of a template-annealed DNA primer, the typical assay for a retroviral RT (FIG. 2). No RNA or DNA nuclease activity beyond that inherent to the wild-type sequence of R2 RT was detected for single- or double-stranded structures across diverse buffer conditions, including $Mg^{2+}$ and $Mn^{2+}$ buffers essential to the RT-protein applications described herein. The same expression context and purification protocol has been used reproducibly for multiple N-terminally truncated R2 RT and multiple intron RT purifications, including a tagged ΔN303 R2 RT variant from Bombyx mori having a D996A mutation that abolishes endonuclease function (SEQ ID NO: 12; also referred to as BomoMin(ed)), which purifies with yield and activities comparable to BomoC(ed).

Among the enzymes screened, the best-produced eukaryotic RT was much more efficient at serial template copying than the best-produced intron RT with an untagged, full-length sequence of SEQ ID NO: 4 (FIG. 3), even though this intron RT has been described as the most processive intron RTs for synthesis across a long template (Zhao C, Liu F, Pyle AM RNA. 2018 24(2):183-195). Because the active site of the R2 RT C-terminal endonuclease domain catalyzed non-specific single-stranded nucleic acid degradation that was particularly extreme in buffers with $Mn^{2+}$ (FIG. 4A), yet that domain substantially contributed to high-yield protein production, solution stability, and purified protein activity (FIGS. 1 and 2), N-terminally truncated R2 RT variants were additionally modified to eliminate nuclease activity, as accomplished by endonuclease-domain active-site mutation described above (referred to as "(ed)" by abbreviation of endonuclease catalytic dead).

Example 2: Single-Stranded and/or Duplexed RNA 3'-End Extension by $Mn^{2+}$-Stimulated Terminal Transferase Activity of Non-Retroviral RTs Diverse molecular biology applications have been greatly enabled by use of the enzyme Terminal deoxynucleotidyl Transferase (TdT), which catalyzes deoxynucleotide addition to DNA 3' ends. TdT can utilize any of the four dNTPs and a variety of other unmodified or modified nucleotides to extend the 3' OH of its preferred single-stranded DNA substrate (Sarac and Hollenstein Chembiochem. 20(7):860-871, 2019). This activity is central to a large number of research and clinical protocols, because it allows a pool of DNA ends (for example single-stranded cDNA ends) to be tailed with a platform for adaptor base-pairing. Also, it can utilize a nucleotide analog with an attached detection or purification signal (fluorescent, radioactive, biotin, or other). Recent applications include its use for de novo oligonucleotide synthesis with reversibly chain-terminating nucleotide analogs.

Unfortunately, no natural variant or engineered form of TdT has been produced to use for extension of single-stranded RNA 3' ends. Instead, single-stranded RNA can be extended by nucleotide-restricted polymerases such as RNA poly(A) polymerase (Eckmann et al. Wiley Interdiscip Rev RNA. 2(3):348-61, 2011). Commercially available RNA poly(A) polymerases typically have high processivity of ribonucleotide addition rather than the distributive deoxynucleotide addition of TdT, resulting in some substrates getting long poly(A) tails while other substrates in the same reaction remain unextended. Furthermore, it is not possible to add different tail sequences to each molecule within one reaction (for example as a unique molecular identifier) or to different pools of molecules in separate reactions later to be combined (for example as a bar code). Additionally, limiting their utility, RNA polymerases such as described above do not 3'-extend double-stranded RNA. Described herein is a TdT-like broad nucleotide substrate terminal transferase activity for 3' extension (also referred to as 3' tailing) of single-stranded RNA utilizing dNTPs, NTPs, and/or ddNTPs, enabling for a breadth of current and future research and clinical applications including some new RNA-seq methods described in this application.

Methods

Combine nucleic acid substrates to be modified in a suitable buffer of the desired pH (typically in the range of pH 6 to pH 9, for example 20 mM Tris-HCl pH 7.5) with $MnCl_2$ (typically in the range of 0.5 to 5 mM, for example 2 mM). Add the NTP, dNTP, ddNTP and/or triphosphate form of nucleotide analog intended to be utilized to extend the 3' OH group(s) of the substrate (for example, dTTP+dCTP+dGTP+dATP+ddATP). Add non-retroviral RT enzyme (e.g., R2 RT or intron RT, typically to a final concentration of 0.2-1 micromolar, for example 0.5 micromolar). Other buffer additives are permissive and/or stimulating to the reaction, excepting chelators of $Mn^2$, such as EDTA. Incubate the assembled reaction at a convenient temperature (typically between 4° C. and 50° C., for example, room temperature or 37° C.) for as long as necessary for reaction to proceed to the desired fraction of substrate extended and/or extent of 3' tailing. Reactions may be stopped by addition of a chelator such as EDTA, or thermal inactivation of the RT (for example 5 min at 65° C.), or hydrolysis of the unused nucleotide substrates (for example using shrimp alkaline phosphatase, NEB). Products may be detected directly by signal generated from 3' tailing (for example, by intercalating dye, absorbance, or FRET), purified to detect incorporated signal (for example, by filter binding or precipitation), used in subsequent reactions (for example, array hybridization or RNA-seq), or resolved (for example, by PAGE or chromatography) among other options.

RNA may be intact or fragmented, chimeric in composition with DNA or other non-RNA, and partially or fully duplexed with RNA or DNA. The protocol above is for RNA ends of 3' OH; if RNA has a 3' group other than OH, repair enzymes may be used to generate a 3' OH prior to 3' tailing. For example, 3' monophosphate or 2'3' cyclic monophosphate is converted to 3' OH by numerous commercially available phosphatase enzymes (for example, T4 PNK). Templates may or may not be denatured to remove secondary structure. Reactions may be supplemented with nucleic acid binding proteins or other compounds that favor access of RNA 3' ends to the enzyme active site.

Reaction conditions may be adjusted to tune processivity. Enzyme active site mutations can provide additional reaction flexibility and scope, for example alter activity dependence on $Mn^{2+}$ to a different divalent cation or to allow use of desired nucleotide analogs.

Results

Figure 4A:
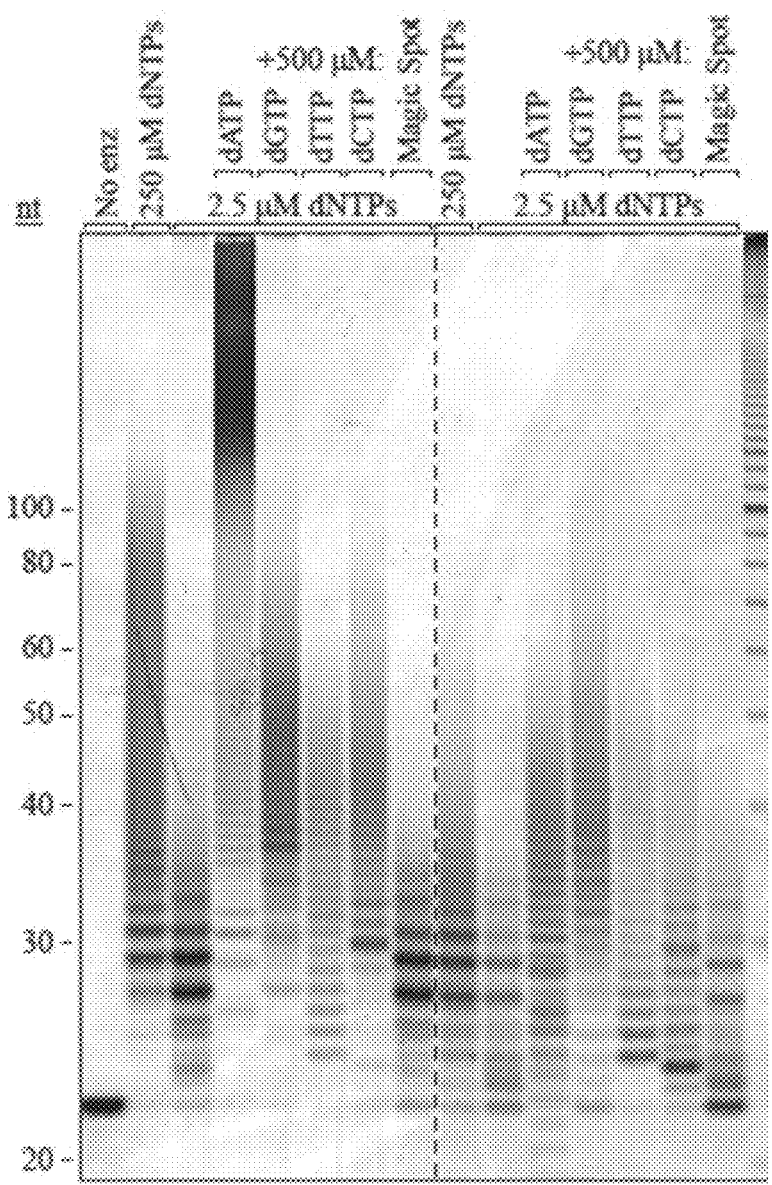
FIG. 4A. Extension of single-stranded RNA 3' ends in the presence of manganese ions, analyzed by denaturing PAGE and SYBR Gold staining. Lane +/−indicates presence or absence of RNase A after product denaturation. "No enz" lane is input RNA oligonucleotide. Gel lanes left of the dashed line were from reactions containing BomoC(ed) endonuclease-inactivated RT proteinwhereas gel lanes to the right of the dashed line contained NBomoC without the endonuclease-inactivating mutation. BomoC(ed) reactions lack the general nucleic acid degradation consistently observed for NBomoC in 3'-tailing buffer conditions with $Mn^{2+}$, which was less pronounced for products with 3' tails of G that fold to G-quadruplex. The product degradation in reactions with NBoMoC was eliminated by endonuclease-inactivating mutation in NBoMoC(ed).
Figure 4B:
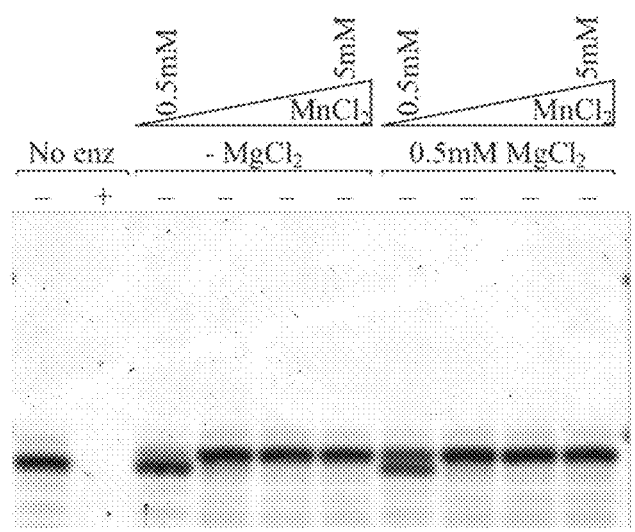
FIG. 4B. BomoC(ed) can utilize ddATP to extend RNA 3' ends in reactions with $Mn^{2+}$ +/−$Mg^{2+}$. The titration of $MnCl_2$ was 0.5, 1, 2, 5 mM for each set.
Figure 5:
FIG. 5 is an image showing Eure RT non-templated extension of single-stranded RNA in the presence of $Mn^{2+}$, analyzed by denaturing PAGE and SYBR Gold staining. RNA oligonucleotide was extended in the presence of $Mn^{2+}$ and different nucleotide triphosphate combinations, including high concentration (500 micromolar) of dATP or each of dTTP and dCTP, either with or without ddNTPs indicated.

Both R2 RT and intron RT demonstrate $Mn^{2+}$-stimulated terminal transferase activity capable of extending RNA substrates (FIGS. 4-6). Because the active site of the R2 RT C-terminal endonuclease domain catalyzed non-specific single-stranded nucleic acid degradation that was particularly extreme in buffers with $Mn^{2+}$ (FIG. 4A), yet that domain substantially contributed to high-yield protein production, solution stability, and purified protein activity (FIGS. 1 and 2), N-terminally truncated R2 RT variants were additionally modified to eliminate nuclease activity, which was accomplished by mutation of the endonuclease-domain active site (see SEQ ID NOs: 3, 12, and 13).

Figures 6A, 6B:
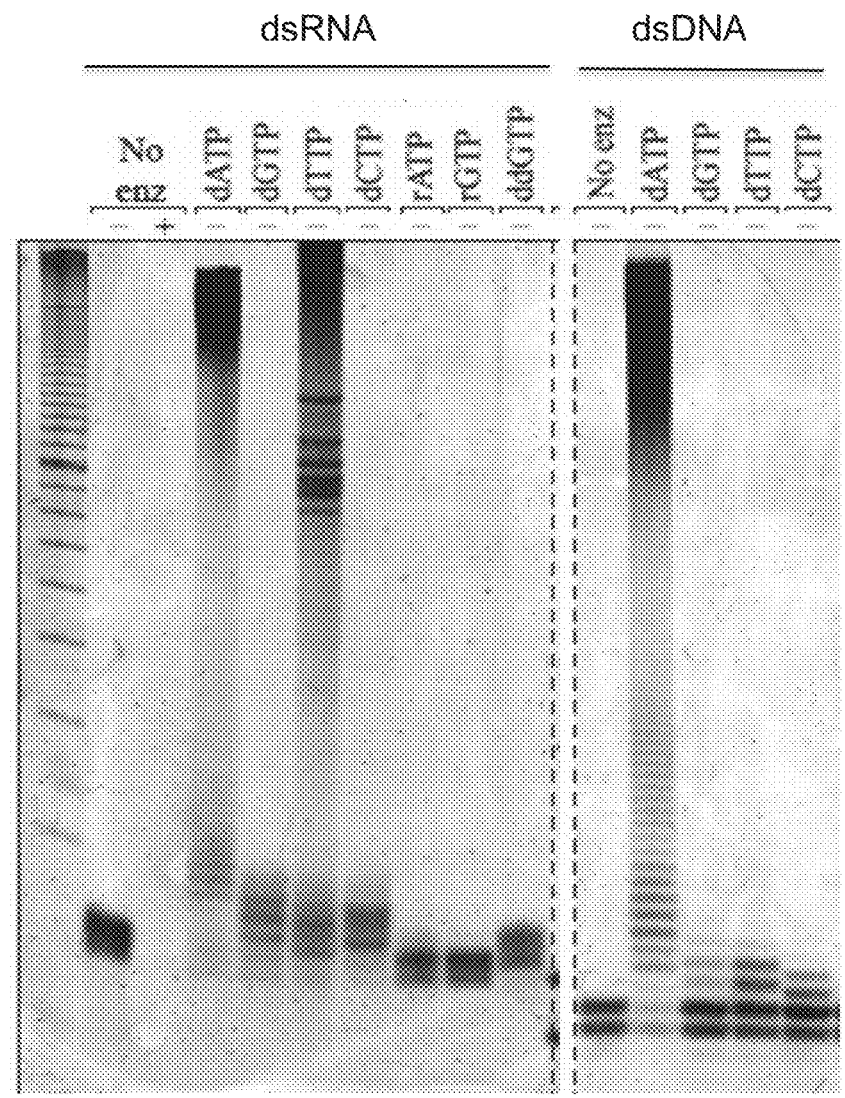
FIG. 6A. Non-templated extension of duplex nucleic acid 3 ends, analyzed by denaturing PAGE and SYBR Gold staining. Assays used BomoC(ed) enzyme. "No enz" lane is input duplex. Lane +/−indicates presence or absence of RNase A after product denaturation. Blunt duplex RNA (dsRNA) or duplex DNA (dsDNA) was extended with the indicated nucleotides, each at 500 micromolar, in reactions with $Mn^{2+}$. The high molecular weight products in "dTTP" lane of the dsRNA set are irreproducible artifact.
FIG. 6B. Blunt duplex RNA (dsRNA) was extended with 500 micromolar of each of 4 dNTPs or dATP only, in buffer with $Mg^{2+}$ or $Mn^{2+}$ as indicated.

The preferences of modified R2 RT and intron RT for particular oligonucleotide and nucleotide substrates differ. This, and additional variants of the enzymes engineered to further tune terminal transferase activity, broaden the possible range of distinct specificities of sequence addition. For both R2 RT and intron RT, different dNTPs or NTPs or nucleotide combinations promote different efficiencies and lengths of 3' extension. For example: dATP is the nucleotide of choice for long overhang generation by R2 RT or intron RT, whereas for short overhang generation dTTP would be a better choice (see FIG. 4A for BomoC(ed) and FIG. 5 for Eure reactions); labeling by addition of a single ddNTP is efficient in reactions with 1-2 mM $MnCl_2$ with or without less than 1 mM $MgCl_2$ present (FIG. 4B); and R2 RT end-labeling of double-stranded RNA to generate long 3' overhangs occurs using dATP while short-overhang synthesis appears ideal in dGTP or dCTP (FIG. 6A). Although double-stranded RNA 3' tailing occurs to a limited extent in buffer with $Mg^{2+}$, it is much more efficient in buffer with $Mn^{2+}$ (FIG. 6B). A feature of reactions containing $Mn^{2+}$ is the lack of uncontrolled single-stranded RNA priming of cDNA synthesis on single-stranded RNA templates with little or no homology, a "self-priming" activity previously described for full-length R2 RT (Luan, Eickbush Mol Cell Biol. 1996 16(9): 4726-34) that in reactions with $Mg^{2+}$ alone creates aberrant product molecules and depletes intact template molecules. Reactions with single-stranded RNA, all dNTPs, and R2 RT in $Mg^{2+}$ buffer sometimes generate ladders of products from an initial non-specific priming event followed by cDNA 3' extension by additional rounds of serial template copying, but that product profile is always distinct from the $Mn^{2+}$-induced non-retroviral RT terminal transferase activity products.

One useful application of the non-retroviral RT ability to extend the 3' end of RNA molecules is to add a uniform 3'-end nucleotide to all of the RNA molecules in a complex mixture, which can promote the equal use of the different molecules by enzymes that bind an RNA 3' end (polymerase, ligase, nuclease, and other). This application allows improvements in sequential template copying for cDNA concatemerization (see Example 4) and also is used to enforce ordered template relay instead of semi-random-order template jumping to create a cDNA library with uniform 5' adaptor and 3' adaptor sequences (see Examples 6-9). Another useful application would be to add signal-coupled nucleotides to a pool of input RNA to generate a hybridization probe useful for example for microarray profiling of a sequence mixture.

Because the previously unanticipated terminal transferase activity of non-retroviral RTs acting on RNA substrates described herein is shared feature of the eukaryotic and prokaryotic RTs, other non-retroviral RTs would be expected to demonstrate this type of activity and could substitute for the RTs used in applications described here. Enzyme fusions can provide additional binding affinity for substrates, for example by covalent or non-covalent joining of RT to single-stranded or double-stranded nucleic acid binding domain(s), enzymes that act to remove secondary structure, or other components.

Example 3: Single-Stranded and/or Duplexed DNA 3' Extension by $Mn^{2+}$-Stimulated Terminal Transferase Activity of Eukaryotic and Bacterial Non-LTR RTs TdT is currently the enzyme of choice for 3' tailing single-stranded DNA. However, its versatility is limited by bias. For example, TdT shows much higher activity incorporating dGTP, dCTP and dTTP than dATP (Berdis et al. Chembiochem. 8(12):1399-408, 2007). With the increased awareness of single-stranded DNA presence in plasma, ancient DNA, and other sources, additional tools for modification and sequencing of this DNA become more critical to develop. This invention addresses this need by providing a terminal transferase for extending DNA 3' ends that is distinct in specificity from TdT or other non-RT-protein polymerases that demonstrate terminal transferase activity.

Methods

Combine nucleic acid substrates to be modified in a suitable buffer of the desired pH (typically in the range of pH 6 to pH 9, for example 20 mM Tris-HCl pH 7.5) with $MnCl_2$ (typically in the range of 0.5 to 5 mM, for example 2 mM). Add the NTP, dNTP, ddNTP and/or nucleotide analog intended to be utilized to extend the 3' OH group(s) of the substrate (for example, dTTP+dCTP+dGTP+dATP+ddATP). Add non-retroviral RT enzyme (e.g., R2 RT or intron RT, typically to a final concentration of 0.2-1 micromolar, for example 0.5 micromolar). Other buffer additives are permissive and/or stimulating to the reaction, excepting chelators of $Mn^{2+}$ such as EDTA. Incubate the assembled reaction at a convenient temperature (typically between 4° C. and 50° C., for example room temperature or 37° C.) for as long as necessary for reaction to proceed to the desired fraction of substrate extended and/or extent of 3' tailing. Reactions may be stopped by addition of a chelator such as EDTA, or by thermal inactivation of the RT (for example 5 min at 65° C.), or by hydrolysis of the unused nucleotide substrates (for example, using shrimp alkaline phosphatase, NEB). Products may be detected directly by signal generated from 3' tailing (for example, by intercalating dye, absorbance, or FRET), purified to detect incorporated signal (for example, by filter binding or precipitation), used in subsequent reactions (for example, array hybridization or RNA-seq), or resolved (for example, by PAGE or chromatography) among other options.

DNA may be intact or fragmented, chimeric in composition with RNA or other non-DNA, and partially or fully duplexed with RNA or DNA. The protocol above is for DNA ends of 3' OH; if DNA has a 3' group other than OH, repair enzymes may be used to generate a 3' OH prior to 3' tailing. For example, 3' monophosphate or 2'3' cyclic monophosphate is converted to 3' OH by numerous commercially available phosphatase enzymes (for example, T4 PNK). Templates may or may not be denatured to remove secondary structure. Reactions may be supplemented with nucleic acid binding proteins or other compounds that favor access of DNA 3' ends to the enzyme active site. Reaction conditions may be adjusted to tune processivity. Enzyme active site mutations can provide additional reaction flexibility and scope, for example alter activity dependence on $Mn^{2+}$ to a different divalent cation or to allow use of desired nucleotide analogs.

Results

Figure 7A:
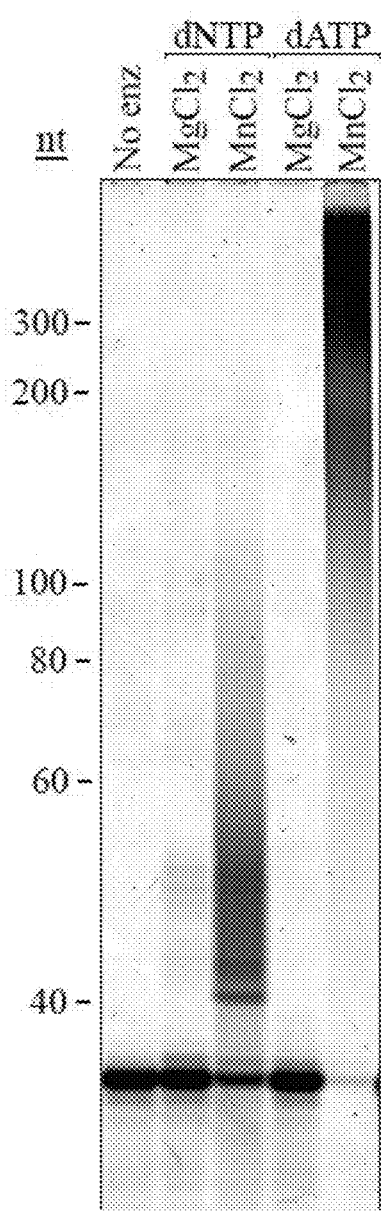
FIG. 7A. BomoC(ed) non-templated extension of single-stranded DNA, analyzed by denaturing PAGE and SYBR Gold staining. "No enz" lane is input DNA. (A) DNA oligonucleotide was extended with 500 micromolar of each of 4 dNTPs or dATP only, in buffer with $Mg^{2+}$ or $Mn^{2+}$ as indicated.
Figure 7B:
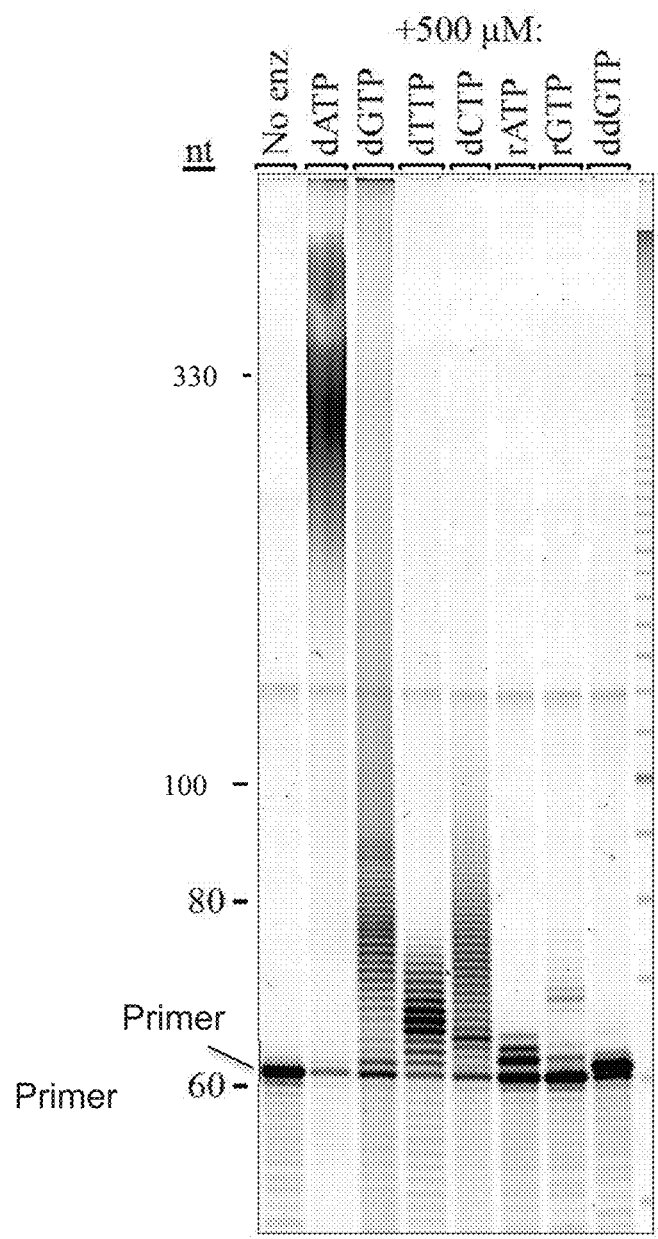
FIG. 7B. DNA oligonucleotide was extended in the presence of $Mn^{2+}$ and different nucleotides as indicated.
Figure 8:
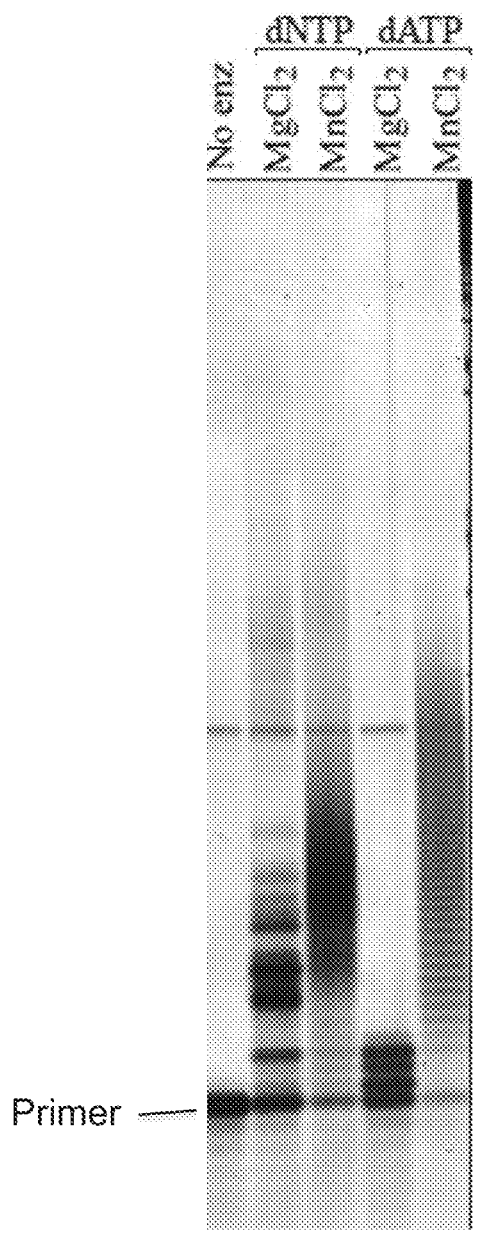
FIG. 8 is an image showing Eure RT non-templated extension of single-stranded DNA. DNA oligonucleotide was extended with 500 micromolar of each of 4 dNTPs or dATP only, in buffer with $Mg^{2+}$ or $Mn^{2+}$ as indicated. "No enz" lane is input DNA. Most products detected in $Mg^{2+}$ buffer with all 4 dNTP represent non-specific oligonucleotide 3' end priming of cDNA synthesis on another oligonucleotide.

Processive terminal transferase activity of the non-retroviral RT occurs in buffers with $Mn^{2+}$ but not $Mg^{2+}$ (see FIG. 7A for BomoC(ed) and FIG. 8 for Eure). In $Mg^{2+}$, intron RT can add 1-3 dATP to a single-stranded DNA 3' end (FIG. 8), but this activity was not detected for R2 RT (FIG. 7A). Reactions with single-stranded DNA, all dNTPs, and R2 RT or intron RT sometimes generate products from DNA synthesis by limited base-pairing of a DNA 3' end with another molecule of DNA in the reaction, but these are distinct from the products of non-retroviral RT terminal transferase activity. The preferences of modified R2 RT and intron RT for particular oligonucleotide and nucleotide substrates differ. This, and additional variants of the enzymes engineered to further tune terminal transferase activity, broaden the possible range of distinct specificities of sequence addition. For example: dATP is the nucleotide of choice for processive 3' tailing of duplexed DNA (FIG. 6A). Also dATP is the nucleotide of choice for long overhang generation on single-stranded DNA, whereas for short overhang generation dTTP would be a better choice (FIG. 7B).

One useful application of the non-retroviral RT ability to extend the 3' end of DNA molecules is to add a uniform 3' end nucleotide to all of the DNA molecules in a complex mixture, which can promote the equal use of the different molecules by enzymes that bind a DNA 3' end (polymerase, ligase, nuclease, and other). This application allows improvements in sequential template copying for cDNA concatemerization (see Example 4) and also is used to enforce ordered template relay instead of semi-random-order template jumping to create a cDNA library with uniform 5' adaptor and 3' adaptor sequences (Examples 6-9). Another useful application would be to add signal-coupled nucleotides to a pool of input DNA to generate a hybridization probe useful for example for microarray profiling of a sequence mixture.

Because the efficient terminal transferase activity of non-retroviral RTs described herein is shared feature of the eukaryotic and prokaryotic RTs, other non-retroviral RTs would be expected to demonstrate this type of activity and could substitute for the RTs used in applications described here. Enzyme fusions can provide additional binding affinity for substrates, for example by covalent or non-covalent joining of RT to single-stranded or double-stranded nucleic acid binding domain(s), enzymes that act to remove secondary structure, or other components.

Example 4: Synthesis of Template-Complementary cDNA Concatemers from Homogeneous or Mixed Templates Tandem sequence arrays have applications in DNA nanotechnology and genome engineering among other purposes (Endo et al. *Current Protoc. Nucleic Acid Chem.* 2011 Chapter 12: Unit12.8; Zhang et al. *Plant J.* 70(2): 357-365, 2012). Their construction and maintenance in cells, on plasmids or chromosomes, is limited by recombination- and repair-mediated deletions and mutations. The typical creation of these arrays by a purified DNA ligase requires duplex segments of DNA, and their creation by PCR requires sequence overlap. A synthetically less expensive and less sequence-constraining method would use single-stranded oligonucleotide DNA templates without sequence overlap. Also, the scope of possible templates would be increased if RNA in addition to DNA was suitable as a template, allowing for example use of biological RNA material or RNA polymerase amplification to create templates. Sequence concatemerization by reiterative template copying could be used to capture the sequence of many molecules into the same adaptor-flanked cDNA product for applications such as PCR or sequencing (for example Pacific Biosciences or Nanopore). Provided herein is a mechanism for these improvements and expansions in scope, as well as others.

Methods

Dilute an array-initiating duplexed primer in a suitable buffer of the desired pH (typically in the range of pH 6 to pH 9, for example 20 mM Tris-HCl pH 7.5). Adjust the reaction to have a desired ratio of the primer duplex to the templates (for example, each in the 45-1000 nM range), a concentration of monovalent ion that stimulates the desired amount of concatemerization (for example in the range of 150-450 mM KCl), $MgCl_2$ (for example 2 mM), and enzyme-stabilizing glycerol (for example 10%) and DTT (for example 1-2 mM). Add the NTP, dNTP and/or triphosphate form of nucleotide analogs (for example, a mixture of dTTP+dCTP+dGTP+dATP+aminoallyl dUTP). Add non-LTR RT enzyme (e.g., R2 RT, typically to a final concentration of 0.1-1 micromolar, for example 0.5 micromolar). Other buffer additives are permissive and/or stimulating to the reaction, excepting many divalent ion chelators such as EDTA. Incubate the assembled reaction at a convenient temperature (typically between 4° C. and 50° C., for example room temperature or 37° C.) for as long as necessary for reaction to proceed to the desired fraction of substrate extended and/or length of cDNA synthesis. Reactions may be stopped by addition of a chelator such as EDTA, or by thermal inactivation of the RT (for example, 5 min at 65° C.), or by hydrolysis of the unused nucleotide substrates (for example, using shrimp alkaline phosphatase, NEB). Products may be detected directly by signal generated from 3' tailing (for example, by intercalating dye, absorbance, or FRET), purified to detect incorporated signal (for example, by filter binding or precipitation), used in subsequent reactions (for example, array hybridization or RNA-seq), or resolved (for example, by PAGE or chromatography) among other options.

The duplex initiating primer can be modified, including modified in sequence to share complementary to template(s). If templates of unknown sequence are 3' tailed with one or several nucleotide additions prior to cDNA synthesis (for example using the terminal transferase activity of R2 RT), the 3' tailing reaction will create a spacer separating cDNA sequence modules.

Results

Figure 3:
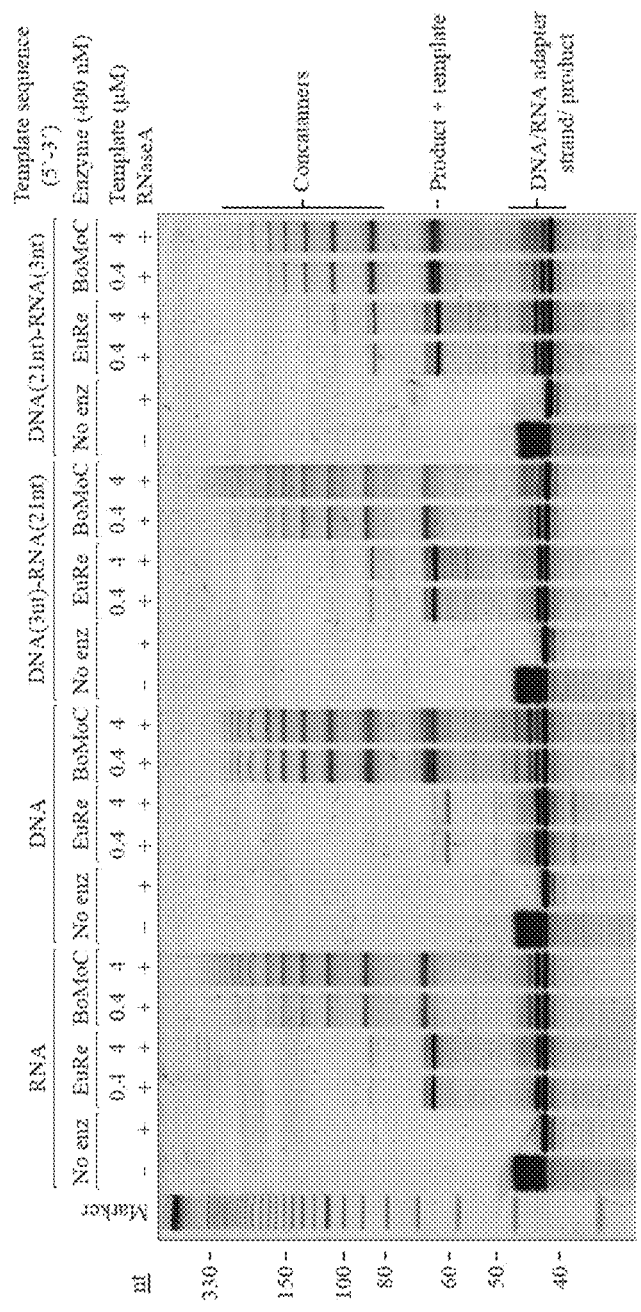
FIG. 3. Processive, serial template copying assayed for purified RT proteins. Primer was DNA with +1T 3' overhang. Templates were 24 nt RNA or DNA or composite of both as indicated at top (Template 5-3'). RT proteins were Eure or BomoC(ed) as indicated (BomoC is used for labeling rather than BomoC(ed) for space considerations). Two concentrations of template were used: 0.4 or 4 micromolar as indicated. Lane +/−indicates presence or absence of RNase A after product denaturation, before denaturing PAGE and SYBR Gold staining. RNase A removes the non-extended strand of the primer duplex and the template, which migrates in a region of the gel below the DNA primer and products shown. "No enz" is the no enzyme control. "cDNA" indicates the product from primer extension by copying a single template, whereas "Concat" indicates primer extention by serial template copying.
Figure 9:
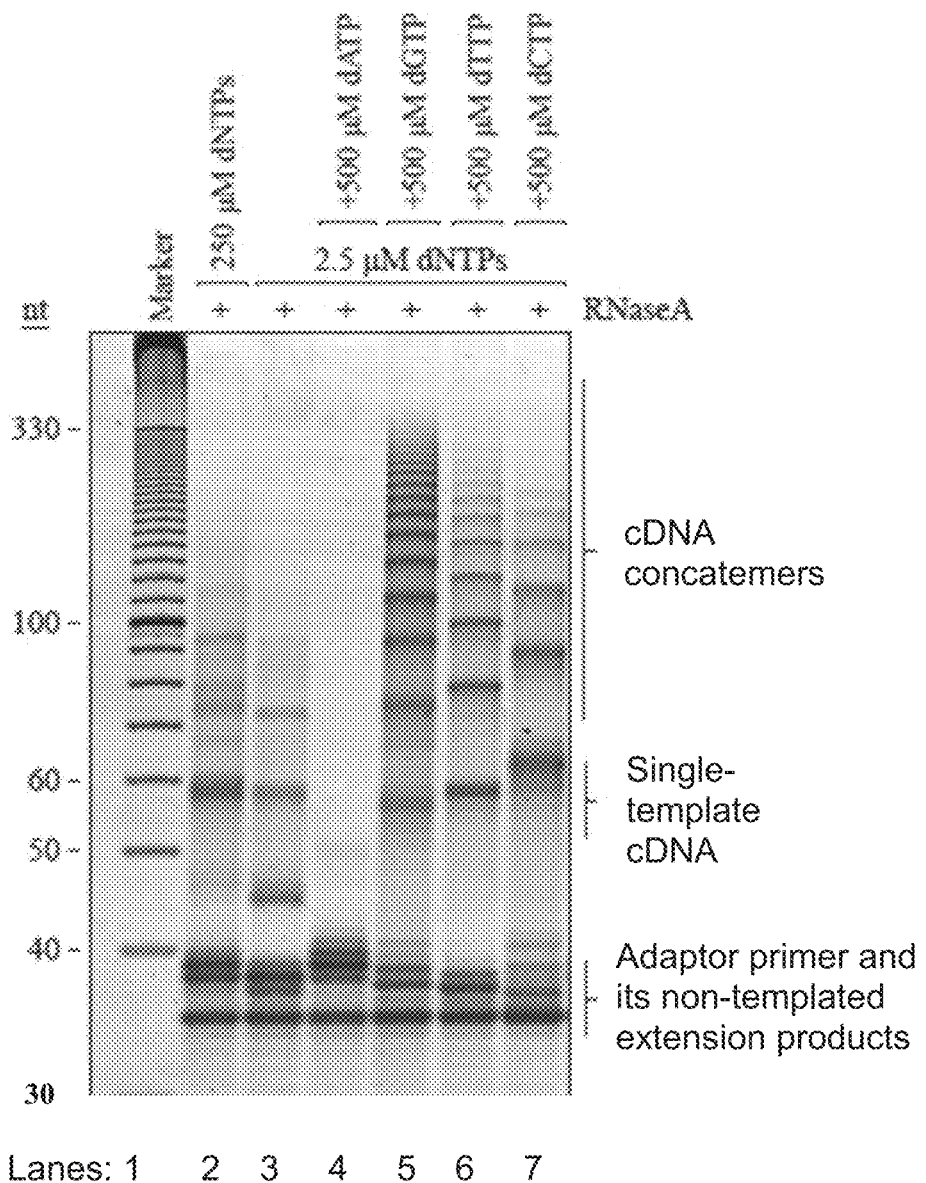
FIG. 9 is an image showing BomoC(ed) cDNA concatemerization by serial template copying, analyzed by denaturing PAGE and SYBR Gold staining. Reactions contained duplexed primer, a high concentration of one dNTP, and a template with 3' end complementary to the high-concentration dNTP. Template in reactions with equal dNTP concentrations was 3' C. "Single-template cDNA" is primer extended by copying one template, while concatamers are product from copying multiple template molecules. Because Primer extension by 2 to 4 non-templated nucleotides inactivates it for priming cDNA synthesis, generating the products migrating just below the 40 nt marker., Lane +indicates addition of RNase A after product denaturation, which removes the non-extended strand of the primer duplex and the templates.
Figure 10:
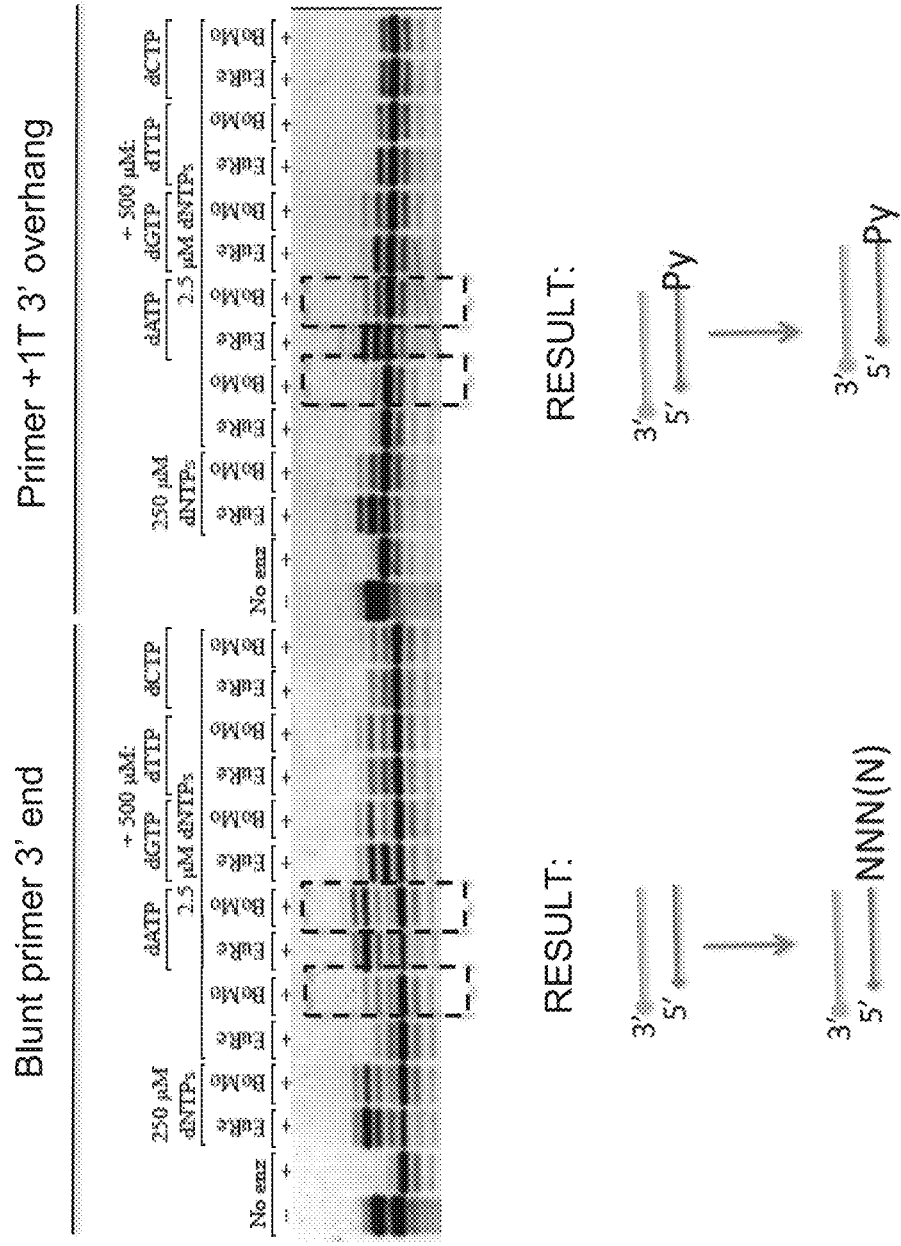
FIG. 10 is an image showing 3' tailing of the DNA primer strand of a primer duplex in cDNA synthesis reactions containing $Mg^{2+}$ but no $Mn^2$, analyzed by denaturing PAGE and SYBR Gold staining. Reactions contained duplexed primer with a blunt end (left side) or +1T overhang (right side) and the indicated dNTP concentrations: each reaction had 250 or 2.5 micromolar of the 4 dNTP mix, and some reactions were supplemented with 500 micromolar of an individual dNTP. Reactions contained either BomoC(ed) (indicated in this Figure as BoMo for space reasons) or Eure RT. "No enz" lanes are input duplex primer with one DNA strand and one RNA strand, the latter with a 3' block to extension. Lane +/−indicates presence or absence of RNase A after product denaturation. Particularly for BomoC(ed), +1T (more generally +1 pyrimidine) overhang on the primer strand suppresses non-templated nucleotide addition in reactions with all 4 dNTPs. This can be seen by comparing the products within dashed boxes against the respective "No enz"+RNase reaction, which provides a marker for the migration of input primer strand alone. The blunt primer end has several nucleotides added to it, but the +1T primer end is largely unchanged. This result is illustrated below the dashed boxes corresponding to the different input primers.
Figure 11:
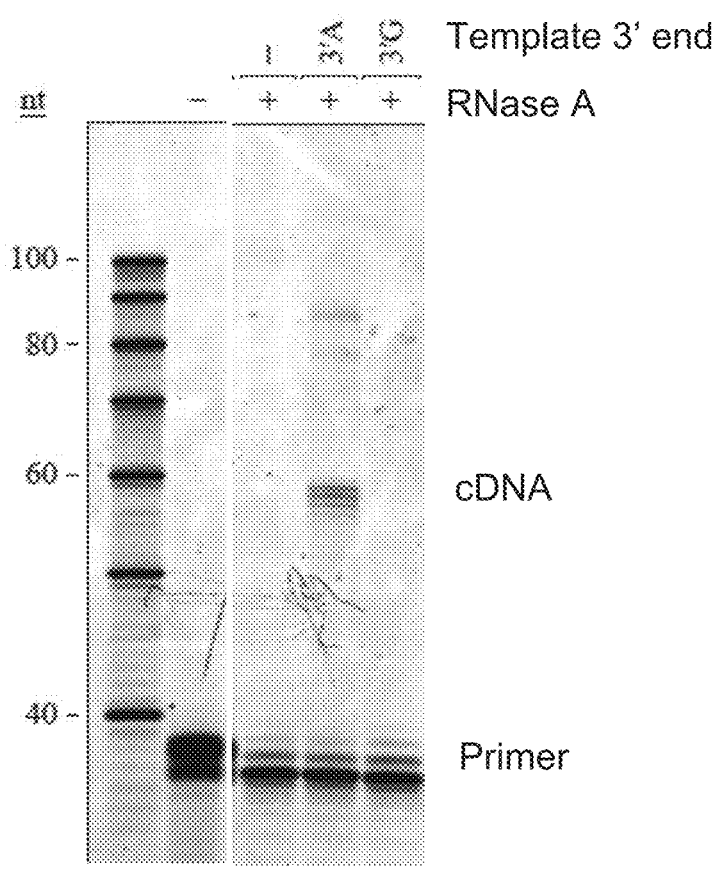
FIG. 11. Enforcement of a unique specificity of the first template relay. BomoC(ed) was assayed using a primer duplex with +1T overhang and templates ending in either 3'

R2 RT cDNA concatemerization efficiency varies with the concentration of dNTPs in the cDNA synthesis reaction (FIG. 9). These influences are determined at least in part by non-templated dNTP addition to a blunt-end primer or cDNA product 3' end (FIG. 10, reactions contain only duplex primer with a blunt or +1T 3' overhang, BomoC(ed), and dNTPs; products reflect non-templated nucleotide addition to the primer 3' end). A one-nucleotide overhang added to a primer or cDNA product 3' end favors use of a complementary template 3' end but inhibits use of templates with non-complementary 3' ends (FIG. 11). A two-nucleotide overhang generally decreases cDNA synthesis and a three or more nucleotide overhang is strongly inhibitory. Because R2 RT preferentially uses several dATP for non-templated extension of a blunt DNA end, typical dATP concentration for a polymerase reaction (for example 250-500 micromolar) inhibits R2 RT cDNA concatamerization relative to a reaction with 100-fold reduced dATP (FIG. 9, compare cDNA products in lane 2 with 250 micromolar dATP, lane 3 with 500 micromolar dATP, and lanes 3 and 5-7 with 2.5 micromolar dATP). In addition to dNTP concentrations, R2 RT efficiency of cDNA concatemerization depends on the 3' nucleotide of the template(s) to be copied. The template 5' nucleotide may also influence the first non-templated dNTP addition, based on results from high-throughput sequencing of R2 RT ordered template relay cDNA libraries. Furthermore, the nature of the template as RNA and/or DNA influences cDNA concatemerization: R2 RT can use RNA or DNA or hybrid DNA-RNA templates with similar efficiency, whereas intron RT is less efficient copying template with a DNA 3' end (FIG. 3).

For efficient concatemerization, a breadth of non-templated addition control strategies can be combined depending on experimental flexibility in the choice of template 3' ends. Under reaction conditions of 2.5 micromolar dNTPs+ 500 micromolar of a single dNTP, cDNA concatemerization reactions with a single template have the order of efficiency of templates with 3' end C>A>G and respectively elevated dGTP, dTTP, or dCTP (FIG. 9). Each reaction component, including salts, affects this preference but general principles of design include using lower than typical RT reaction concentration of dATP (for example, a maximum of 100 micromolar).

Example 5: Irreversible or Reversible cDNA Synthesis Termination cDNA libraries used for RNA-seq and other applications require distinct 5' and 3' adaptor sequence handles, which random-jumping order among possible templates mixed into a cDNA synthesis reaction does not provide. Also, inclusion of more than one template's cDNA between the adaptors precludes critical conclusions such as the location of cancer-causing chromosome translocation breakpoints, with false-positive fusions being a major artifact of current RNA-seq methods using retroviral RTs (Panagopoulos et al. *Int J Biochem Cell Biol.* 53:462-5, 2014). For control of the order of template use and the number of templates copied in tandem, it would be desirable to terminate cDNA synthesis after copying a 3' cDNA library adaptor sequence. Described herein are methods for this improvement.

Method 1

Termination that is irreversible without template removal is accomplished by using a cDNA 3' adaptor template with a 5' backbone modification or extension that allows complete template copying but not elongation-productive binding of another template molecule. The cDNA 3' adaptor template is synthesized with bulky or otherwise disruptive modification that can be an extension of the backbone (for example, 5' addition of biotin, Cy3 or Cy5, or other large group) or a sufficient length of backbone modification or extension comprised of linkages other than phosphodiester (for example, LNA or PNA) or a continued phosphodiester or phosphodiester-like backbone without bases (several tandem abasic sites). In addition to these covalently attached modifications, non-covalently attached modifications such as a tightly bound protein barrier or other impediment prevent additional template engagement.

Method 2

Sequential template use can also be blocked by 5' backbone extensions conditionally removed by non-enzymatic cleavage, for example PC Biotin (IDT) with a 300-350 nm irradiation photocleavable spacer between the biotin group and the oligonucleotide. Alternately, enzymatic 5' adenylylation (attachment of AMP) (Lama et al. *RNA*. 22(1):155-61, 2016) creates a highly efficient block to tandem template use, and this modification can be removed by enzymes with oligonucleotide pyrophosphatase activity such as RppH.

Results

Some candidate blocking groups attenuate tandem template use while others eliminate it (FIG. 12). Some blocking groups such as 5' adenylylation can be added to biological as well as synthetic adaptor templates. Termination that is ready reversible allows serial rounds of the combination of cDNA extension by added template and excess template removal; such reiterative combinatorial bar-coding would allow more multiplexing of mixed molecule pools and can be envisioned to provide higher resolution for spatial transcriptomics (Moor et al. *Curr Opin Biotechnol.* 46:126-133, 2017).

Example 6: Single-Reaction Double-Adaptor-Tagged cDNA Synthesis by Ordered Template Relay For many applications, the most efficient synthesis of a cDNA library would add both the 5' and 3' adaptors to a reverse-transcribed template-complementary sequence in the same reaction, with no reliance on user purification or other handling of a reaction intermediate. Furthermore, instead of adding these adaptors interchangeably in semi-random order without distinction among templates in a reaction pool (FIG. 13A), it would be advantageous to enforce an order of template use that places 5' and 3' adaptors on either side of a cDNA and does so with retained information about which end of the cDNA was the template 5' versus 3' end (FIG. 13B). Described herein are methods for this improvement (FIG. 13B), which can be exploited by other applications as well.

Methods

To enforce distinct specificity of the first and second template relay steps used to fuse 5' and 3' adaptors to a cDNA, the first-step and second-step primer and template 3' ends are of different identity (FIG. 13B). This demands a strategy for restraining the RT from recognizing the 5' adaptor primer 3' end in the same manner as the template-complementary cDNA product 3' end. Fortunately, with R2 RT but not intron RT, a primer+1 pyrimidine overhang suppresses additional 3' extension to the otherwise observed 3-4 nucleotide overhang (FIG. 10). This feature allows the initiating primer 3' end to be distinct from the 3' end of a cDNA, which will be subject to the blunt-end primer 3' end rules for non-templated dNTP addition. Templates with a purine nucleotide 3' end, for example A, that is cognate to a cDNA 5' adaptor primer with the cognate+1 overhang of a pyrimidine nucleotide, for example T, will be copied in preference to any other possible template molecules lacking the cognate 3' end to the primer+1T (FIG. 13B). However, because non-templated nucleotide addition occurs with strong preference for purine nucleotide incorporation (FIGS. 9 and 10), the template-complementary cDNA 3' end will not be able to engage another molecule from the 3'-purine template pool (FIG. 13B). Instead, if a cDNA 3' adaptor template with 3' pyrimidine, for example C, is also present in the reaction, it will be used for the second step of template relay (FIG. 13B).

Efficiency of the second step of template relay can be manipulated by suppressing non-productive 3' tailing of the cDNA intermediate, for example with dNTP concentration changes or dNTP analogs. Also efficiency can be manipulated by increasing local concentration of adaptor template, for example with droplet technologies or surface immobilization. In addition, other principles of enforcing different specificity of first versus second template relay step can be envisioned, for example using dNTP analogs. For example, the template pool could be 3'-extended using a non-templated addition reaction with iso-dG at high concentration, which would not be incorporated into the cDNA in the presence of template-cognate dNTPs but could be used for non-templated nucleotide addition to the cDNA 3' overhang; iso-dG will pair preferentially with iso-dC, which could be placed uniquely at the 3' end of the 3' adaptor template. These non-canonical nucleotides would lack templating fidelity when used in reactions with mismatch-tolerant polymerase (such as R2 RT) and canonical dNTPs only, but this can be readily accommodated in sequence analysis.

Results

Ordered template relay accomplishes the desired specificity of cDNA synthesis. Because the cDNA 3' adaptor template with 3' pyrimidine is not engaged by the cDNA 5' adaptor primer+1 pyrimidine, adaptor dimer is minimal, especially in presence of template pool with 3' nucleotide cognate to the primer+1 overhang nucleotide (FIG. 12, compare products from reactions lacking an adaptor template (lanes 4, 9) to products from reactions containing adaptor template (lanes 5-8, 10-13)). A 5' blocking group on the adaptor template halted serial template copying after addition of a single cDNA 3' adaptor sequence (FIG. 12, compare products from reactions lacking an adaptor template block (lanes 5-6 and 10-11) to reactions containing adaptor template 5' block (lanes 7-8 and 12-13)).

Example 7: Suppression of Template Loss and cDNA Synthesis Reaction Side-Products by Template 3' End Modification R2 RT preparations show ability to use a single-stranded RNA as primer for cDNA synthesis, even without complementarity of the RNA primer and template (Luan et al. *Mol. Cell Biol.* 16(9): 4726-4734, 1996; Bibillo et al. *J. Mol. Biol.* 316(3): 459-479, 2002). This results in a large amount of template use as primer for copying another template molecule, generating undesired duplex reaction products including sense-antisense template fusions, and/or depletion of template 3' ends from recognition by the RT as template. Ideally, a modification of intended template pool 3' ends would preclude destructive template use as primer while retaining ability of the molecules to be recognized as a template for cDNA synthesis from the intended duplex primer or product DNA 3' end. Provided herein is this improvement for both RNA and DNA templates.

Method 1: Template 3' Extension by R2 or Intron RT Addition of ddNTP

Combine nucleic acid substrates to be modified in a suitable buffer of the desired pH (typically in the range of pH 6 to pH 9, for example 20 mM Tris-HCl pH 7.5) with $MnCl_2$ (typically in the range of 0.5 to 5 mM, for example 2 mM). Add the ddNTP(s)+/−dNTP(s) intended to be utilized to extend the 3' OH group(s) of the substrate (for example, dTTP+dCTP+dGTP+dATP+ddATP or only ddATP or only ddGTP). Add non-retroviral RT enzyme (e.g., R2 RT or intron RT, typically to a final concentration of 0.2-1 micromolar, for example 0.5 micromolar). Other buffer additives are permissive and/or stimulating to the reaction, excepting chelators of $Mn^2$ such as EDTA. Incubate the assembled reaction at a convenient temperature (typically between 4° C. and 50° C., for example room temperature or 37° C.) for as long as necessary for reaction to proceed to the desired fraction of substrate acquisition of 3'H instead of 3'OH. Reactions may be stopped by addition of a chelator such as EDTA, thermal inactivation of the RT (for example, 5 min at 65° C.), or hydrolysis of the unused nucleotide substrates (for example, using shrimp alkaline phosphatase, NEB).

Method 2: DNA Template 3' Extension by TdT Addition of ddNTP

Combine nucleic acid substrates to be modified in a suitable buffer of the desired pH (typically in the range of pH 6 to pH 9, for example 20 mM Tris-HCl pH 7.5) with the appropriate divalent cations $MgCl_2$ and/or $MnCl_2$ (typically in the range of 1 to 5 mM, for example 2 mM). Add the ddNTP(s)+/−dNTP(s) or NTP(s) intended to extend the 3' OH group(s) of the substrate (for example, ddATP+/−dATP or ddGTP+/−dGTP or ATP+ddATP or other combination; TdT can incorporate a limited number of ribonucleotides). Add TdT at the manufacturer's recommended dilution. Incubate the reaction at a convenient temperature (typically about 37° C.) for as long as necessary for substrate acquisition of 3'H instead of 3'OH. Reactions may be stopped by addition of a chelator such as EDTA, thermal inactivation of TdT (for example 20 min at 75° C.), or hydrolysis of the unused nucleotide substrates (for example using shrimp alkaline phosphatase, NEB).

Results

Templates with a 3' terminal dideoxynucleotide are efficiently recognized for initiation by template relay. Because these templates lack an extendable 3' OH group, R2 RT reaction products detected directly by SYBR Gold staining after denaturing PAGE (FIG. 14A and FIG. 14B) lack the abundance of non-specific reaction products that otherwise predominate reactions containing templates of more than a few tens of base-pairs in length. These non-specific reaction products are largely invisible to reactions assayed indirectly by PCR with adaptor-sequence oligonucleotides; only resolution and direct detection of reaction products, not reaction product detection by PCR, revealed the full extent of the improvement in 3' dideoxynucleotide-tailed template use for cDNA synthesis. In particular, ddA templates were used efficiently when the cDNA 5' adaptor primer was the ~35 nt complement of Illumina Read2 sequence alone (FIG. 14A) or a full-length ~70 nt Illumina NGS adaptor comprised of the complement of P7, a bar code i7, and Read2 (FIG. 14B). With each of these 5' adaptor primers, ddA templates were converted to full-length cDNA libraries by the second template relay step using any of several 3' adaptor templates: a random sequence (Optimal), ~35 nt Universal 3' adaptor template with Illumina Read 1, or ~70 nt full-length Illumina NGS adaptor comprised of P5, a bar code i5, and Read 1 (FIG. 14A and FIG. 14B). Production of side-products including adaptor dimer was minimal (FIGS. 14A and 14B).

Example 8: PCR-Free Next-Generation Sequencing (NGS) cDNA Library Production in a Single Vessel, without Partitioning or Immobilization Steps The most efficient synthesis of a cDNA library for NGS sequencing using, for example, the market-predominant Illumina platform would add both the 5' and 3' adaptors to a reverse-transcribed sequence in the same reaction, with no reliance on user purification or other handling of an intermediate product. Furthermore, it would be ideal to use a method that can generate a library without the sample handling, time elapsed, hands-on time, non-quantitative representation, and other handicaps imposed by requirement for a PCR step. Provided herein are methods for this improvement, as well as other applications. Some applications of cDNA synthesis will benefit from a double-stranded DNA product, resulting from initial cDNA synthesis and second-strand synthesis of the initial cDNA complement. For example, the double-stranded product serves as a target for hybridization of both template sense- and antisense-strands. As another example, double-stranded product can be cloned into plasmid vectors using T4 DNA ligase and other common strategies. Provided herein are methods for this improvement.

Methods cDNA Synthesis

Dilute input templates in sterile water. Double-stranded DNA or RNA should be heat-denatured to generate a 3' single-stranded region. Protocol is scaled for final volume 20 μL, typical input ~1 pmole 3' ends. If templates are 3' $PO_4$, begin with STEP1. Reaction temperatures given as 37° C. are example temperatures within a large range of possible alternatives (typically between 4° C. and 50° C.).

STEP 1 (generate 3' OH) To 7.5 μL sample add 3 μL Input dilution buffer (4×). Add 1 μL buffer A1 (12×) and 0.5 μL T4 PNK (NEB, pre-diluted as 3 volumes water: 1 volume enzyme stock). Incubate at 37° C. ~10 min. Incubate at 65° C. ~20 min.

IF SKIP STEP 1: Dilute input to 12 μL. Add 1.4 μL buffer B2a (10×) and 0.7 μL buffer B1b (20×). Continue to STEP 2 after addition of B buffers.

STEP 2 (3' tail templates) Add 0.7 μL buffer B1a (20×). Add 0.7 μL buffer B1b (20×). Add 1 μL modified R2 RT.

Incubate at 37° C. ~20 min. Incubate at 65° C. ~5 min. Add 1 μL buffer C (16×) and 0.5 μL rSAP. Incubate at 37° C. ~15 min. Add 1 μL buffer D (20× for next step). Incubate at 65° C. ~5 min.

STEP 3 (cDNA synthesis). Add 1 μL cDNA prep mix (20×). Add 1 μL cDNA start mix (20×). Add 1 μL modified R2 RT. Incubate at 37° C. ~20 min. Incubate at 65° C. ~5 min.

Reagent list (store each at −20° C.):
Input dilution buffer (4×): 80 mM Bis-Tris (pH 6.0).
Buffer A1 (12×): 120 mM Bis-Tris (pH 6.0), 12 mM $MgCl_2$, 12 mM DTT
Buffer B1a (20×): 0.4 M Tris-HCl (pH 7.5), 0.4 M KOH, 3 M KCl
Buffer B1b (20×): 40 mM $MnCl_2$, 10 mM ddATP
Buffer B2a (10×): 0.2 M Tris-HCl (pH 7.5), 1.5 M KCl, 10 mM DTT
Buffer C (16×): 80 mM $MgCl_2$
Buffer D (20×): 100 mM EGTA
cDNA prep mix (20×): 10 mM $MgCl_2$, 900 mM KCl, 40% PEG-6000
cDNA start mix: combine equal volumes of the below to make 20× start mix
40× 'cDNA start mix' nucleotides: 20 mM each dGTP/dTTP/dCTP, 4 mM dATP
40× 'cDNA start mix' pool of oligonucleotides
Oligonucleotide preparation (synthesize, for example by ordering the below from IDT):
The no-PCR workflow uses ~70 nt adaptor primer and adaptor template annealed to ~30 nt complement strands for each: final concentration of each partial duplex is 90 nM. Indexes are underlined; these are the variable bar codes.
Adaptor primer partial duplex contains:

c5p(FL):
(SEQ ID NO: 15)
5'-CAAGCAGAAGACGGCATACGAGATGACGAGAGGTGACTGGAGTTCA
GACGTGTGCTCTTCCGATCT-3' c5pt:
(SEQ ID NO: 16)
5'rGrArUrCrGrGrArArGrArGrCrArCrArCrGrUrCrUrGrArAr
CrUrCrCrArGrU/3SpC3/-3'

Adaptor template partial duplex contains: IDC-27 DNA c3t(FL):
(SEQ ID NO: 17)
5'-/5AmMC6/AArUrGrArUACGGCGACrCrArCrCGAGATCTArCrA
rCrCGCAGACGArCrArCrUCTTTCCCTrArCrArCGACGCTCTrUrCr
CrGrArUrCrUrC-3' c3t_comp:
(SEQ ID NO: 18)
5'/c/rGrUrGrUrArGrArUrCrUrCrGrGrUrGrGrUrCrGrCrCrG
rUrArUrCrArUrU/3SpC3/-3'

(ii) Optional cDNA Synthesis Continuation to Double-Stranded cDNA

Method 1

Supplement double-ended cDNA adaptor addition reaction products with at least RNase H2 (nicks 5' to single ribonucleotide to leave DNA 3'OH in this application), with or without additional RNase H1 (nicks between $1^{st}$ and $2^{nd}$ of 4 ribonucleotides, which in this application leaves RNA 3'OH), and R2 RT or another DNA polymerase or RT. For this method, the cDNA 3' adaptor template 5' end should be DNA to remain associated with the cDNA product after RNase H treatment. If the cDNA template and/or other regions of 5' adaptor primer complement or 3' adaptor template are not removed (for example if they are DNA), the added DNA polymerase or RT should have strand displacement activity.

Method 2

Supplement double-ended cDNA adaptor addition reaction products with nucleases or otherwise dissociate the template and cDNA strands, for example by heat, in the region of at least the 5' end of the cDNA 3' adaptor template. Add a primer for second strand synthesis and a DNA polymerase or RT. If the cDNA template and/or regions of 5' adaptor primer complement or 3' adaptor template are not removed, the added DNA polymerase or RT should have strand displacement activity.

(iii) Additional Alternatives and Continuations of Method

The workflow may be performed only in part depending on the application. Samples can be pooled or split mid-workflow. The method may be preceded by RNA or DNA fragmentation in the same or a different container. Templates may or may not be denatured to remove secondary structure. Reactions may be supplemented with nucleic acid binding proteins or other compounds that favor template binding to or 3' end access to the enzyme active site. Reaction conditions may be adjusted to tune processivity. In the template 3' extension step, modified R2 RT can be supplemented with another non-retroviral RT to broaden the efficiency of template extension.

Enzyme fusions can provide additional binding affinity for substrates, for example by covalent or non-covalent joining of RT to single-stranded or double-stranded nucleic acid binding domain(s), enzymes that act to remove secondary structure, and others. Products can be amplified by PCR or other technique to increase amount of product, or to add or subtract or modify sequence, for example for immobilization or affinity purification of cDNA product using biotin and/or other affinity ligand in oligonucleotides.

Results

This generates single-stranded cDNA library that will bind the P5 oligonucleotide in the flow cell (FIG. 15A). Benchmarking by sequencing a commonly used commercial standard of 963 mixed miRNA (miRXplore) demonstrates that sequencing-ready cDNA libraries can be produced in less than 2 hours in a single-tube reaction workflow, then introduced to the Illumina NGS flow cell without PCR and without depletion or size selection to remove undesired side products generated in other protocols for miRNA library production. Analysis of reaction products by denaturing PAGE and SYBR Gold staining (FIG. 15B) indicates that the production of side-products including adaptor dimer is nearly undetectable relative to the predominant cDNA library (labeled "cDNA+adaptor template") and some cDNA product from copying of the miRNA template only (labeled "cDNA"). Quantification of read counts per each of the 963 miRNA demonstrates the capture of the entire inventory of 963 miRNA in less than 1 million mapped reads (FIG. 16B; X axis values are log 2-scale read counts for no-PCR library from less than 1 million mapped reads, and the apparent zero value has a non-zero value).

Template-strand nucleic acids can be released or removed, for example by heat denaturation, base hydrolysis, or nuclease degradation, for applications benefiting from single-stranded nature of the cDNA product. For some applications, cDNA will be purified from free and/or bound RNA, for example with RNase H and/or RNase A. For some applications, cDNA will be purified from other reaction components for example using precipitation, nucleic acid binding support, electrophoresis or other method. For some applications, cDNA will be converted to duplex DNA. For some applications, cDNA will be purified to enrich a particular size range, for example by differential precipitation, binding to or partitioning with a support, electrophoresis or other method.

With minimal additional sample handling or elapsed time, single-stranded cDNA generated by ordered template relay can be converted to double-stranded product. Flexibility in design of the composition of the ordered template relay 3' adaptor template provides numerous opportunities for approaches to second-strand synthesis.

Example 9: PCR Indexing of NGS cDNA Library in a Single Vessel, without Partitioning or Immobilization Steps The most efficient synthesis of a cDNA library for NGS sequencing using, for example, the market-predominant Illumina platform would add both 5' and 3' adaptors to a reverse-transcribed template-complementary sequence in the same reaction, with no reliance on user purification or other handling of an intermediate product. It is common practice to generate cDNA libraries with short flanking adaptors then use indexed PCR primers to distinguish cDNA pools prior to their combined sequencing (Park Y S, Kim S, Park D G, Kim D H, Yoon K W, Shin W, and Han K. *Genes Genomics*. Epub, Jul. 26 2019). This strategy reduces the maximal length of any individual synthetic oligonucleotide required. Invention here provides methods for the strategy of cDNA library construction employing a PCR reaction after an RT reaction.

Methods

Follow protocol described above in Example 8, except with different oligonucleotides and adding a final PCR step. The PCR-indexing workflow optimally uses ~35 nt oligos in the RT reaction: final concentration of each is 180 nM. Indexes are underlined; these are the variable bar codes.

Adaptor primer duplex contains:

c5p(uni):
(SEQ ID NO: 19)
5'-GTGACTGGAGTTCAGACGTGTGCTCTTCCGATCC-3' c5pt:
(SEQ ID NO: 20)
5'rGrArUrCrGrGrArArGrArGrCrArCrArCrGrUrCrUrGrArAr
CrUrCrCrArGrU/3SpC3/-3'

Adaptor template is:

c3t(uni):
(SEQ ID NO: 21)
5'-/5Phos/ACACTCTTTCCCTACACGACGCTCTTCCrGrArUrCrUr
C-3'

The PCR step parallels a standard Illumina library generation PCR reaction. PCR (for example 4-8 cycles of 98° C. 20 sec/65° C. 20 sec/72° C. 5 sec) with a thermostable DNA polymerase (for example Q5) using cDNA library as template and the primers below will add P5 and P7 adaptors.

P7:
(SEQ ID NO: 22)
5'-CAAGCAGAAGACGGCATACGAGATTCGATCCAGTGACTGGAGTTCA
GACGTG-3'

P5:
(SEQ ID NO: 23)
5'-AATGATACGGCGACCACCGAGATCTACACCGCAGACGACACTCTTT
CCCTACACGAC-3'

Results

This method generates double-stranded cDNA library (FIG. 16A). Benchmarking by sequencing a commonly used commercial standard of 963 mixed miRNA (miRXplore) demonstrates that sequencing-ready cDNA libraries can be produced in 2-3 hours. Comparison of read counts for each of the 963 miRNA in no-PCR library (X-axis values, single-stranded library) versus the low-cycle PCR library (Y axis values, double-stranded library) demonstrates similar performance, with both methods capturing the entire inventory of 963 miRNA in less than 1 million mapped reads (FIG. 16B). Perfect agreement would place each dot on the line that was fit through the actual data. The agreement between low-PCR and no-PCR (FIG. 16B) is comparable to the concordance between 2 replicates of low-PCR but less than the concordance of two replicates of no-PCR. Either the PCR-free or the low-cycle PCR ordered template relay protocol gave greater or equal number of miRNA identified, and lower coefficients of variation for read counts across the sequenced miRNAs, than obtained using any of 4 commercial miRNA or small RNA sequencing kits, based on parallel analysis of sequence reads deposited from a cross-comparison study (Coenen-Stass et al. *RNA Biology* 15(8) 1133-45 2018).

For some applications, cDNA will be enriched prior to PCR; this may involve DNA separation from templates, removal of dNTPs and oligonucleotides, concentration, or size fractionation among others. For some applications, DNA will be purified from other reaction components for example using precipitation, nucleic acid binding support, electrophoresis or other method. For some applications, DNA will be purified to enrich a particular size range, for example by differential precipitation, binding to or partitioning with a support, electrophoresis or other method.

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated eukaryotic non-long terminal repeat reverse transcriptase (non-LTR RT) protein comprising a truncated N-terminal region, an RNA binding domain, an RT domain, and an endonuclease domain, wherein the endonuclease domain comprises a mutation that abolishes endonuclease function, wherein the eukaryotic non-LTR RT protein is a *Bombyx mori* R2 RT protein, the truncated N-terminal region results in a deletion of 274 amino acids from the N-terminus of the non-LTR RT protein as compared to a corresponding full-length non-LTR RT protein having the amino acid sequence of SEQ ID NO: 1, and the mutation that abolishes endonuclease function is a substitution mutation at amino acid residue D996, D1009, or K1026 of full-length *Bombyx mori* R2 RT (SEQ ID NO:1).

2. The eukaryotic non-LTR RT protein of claim 1, wherein the substitution mutation is at amino acid residue D996.

3. The eukaryotic non-LTR RT protein of claim 2, wherein the amino acid residue D996 is substituted by any amino acid, except Glu (E).

4. The eukaryotic non-LTR RT protein of claim 3, wherein the substitution mutation is a D996A mutation.

5. The eukaryotic non-LTR RT protein of claim 1, wherein the substitution mutation is at amino acid residue D1009; amino acid residue D1009 is substituted by any amino acid, except Glu (E); the substitution mutation is a D1009A mutation; the substitution mutation is at amino acid residue K1026; the substitution mutation is a K1026A, K1026D, or K1026E mutation; the substitution mutation is a K1026A mutation; the mutation that abolishes endonuclease function are substitution mutations at amino acid residues K1026 and K1029; or the substitution mutations are K1026A and K1029A mutations.

6. The eukaryotic non-LTR RT protein of claim 1, further comprising a stabilizer protein, wherein the stabilizer protein is a maltose binding protein (MBP).

7. The eukaryotic non-LTR RT protein of claim 6, wherein the stabilizer protein is MBP and is connected to the N-terminus of the eukaryotic non-LTR RT protein.

8. The eukaryotic non-LTR RT protein of claim 1, further comprising a purification tag, wherein the purification tag is a histidine tag, a protein A tag, or a FLAG peptide tag.

9. The eukaryotic non-LTR RT protein of claim 8, wherein the histidine tag is a 6×-histidine tag.

10. The eukaryotic non-LTR RT protein of claim 8, wherein the purification tag is connected to the C-terminus of the eukaryotic non-LTR RT protein.

11. The eukaryotic non-LTR RT protein of claim 1, wherein the eukaryotic non-LTR RT protein comprises the amino acid sequence of SEQ ID NO: 2.

12. The eukaryotic non-LTR RT protein of claim 1, wherein the eukaryotic non-LTR RT protein comprises the amino acid sequence of SEQ ID NO: 3.

* * * * *

SEQUENCE LISTING

<160> NUMBER OF SEQ ID NOS: 23

<210> SEQ ID NO 1
<211> LENGTH: 1114
<212> TYPE: PRT
<213> ORGANISM: Bombyx mori

<400> SEQUENCE: 1

Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
                20                  25                  30

Arg Gly Pro Ser Ser Leu Ala Gly Thr Phe Gly Trp Gly Leu Ala Ile
            35                  40                  45

Pro Ala Gly Glu Pro Cys Gly Arg Val Cys Ser Pro Ala Thr Val Gly
    50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly
            115                 120                 125

Val His Lys Arg Arg Ala His Pro Val Glu Thr Asn Thr Asp Ala Ala
        130                 135                 140

Pro Met Met Val Lys Arg Arg Trp His Gly Glu Glu Ile Asp Leu Leu
145                 150                 155                 160

Ala Arg Thr Glu Ala Arg Leu Leu Ala Glu Arg Gly Gln Cys Ser Gly
                165                 170                 175

```
Gly Asp Leu Phe Gly Ala Leu Pro Gly Phe Arg Thr Leu Glu Ala
            180                 185                 190

Ile Lys Gly Gln Arg Arg Glu Pro Tyr Arg Ala Leu Val Gln Ala
        195                 200                 205

His Leu Ala Arg Phe Gly Ser Gln Pro Gly Ser Ser Gly Gly Cys
    210                 215                 220

Ser Ala Glu Pro Asp Phe Arg Arg Ala Ser Gly Ala Glu Ala Gly
225                 230                 235                 240

Glu Glu Arg Cys Ala Glu Asp Ala Ala Tyr Asp Pro Ser Ala Val
                245                 250                 255

Gly Gln Met Ser Pro Asp Ala Ala Arg Val Leu Ser Glu Leu Leu Glu
            260                 265                 270

Gly Ala Gly Arg Arg Arg Ala Cys Arg Ala Met Arg Pro Lys Thr Ala
            275                 280                 285

Gly Arg Arg Asn Asp Leu His Asp Asp Arg Thr Ala Ser Ala His Lys
            290                 295                 300

Thr Ser Arg Gln Lys Arg Arg Ala Glu Tyr Ala Arg Val Gln Glu Leu
305                 310                 315                 320

Tyr Lys Lys Cys Arg Ser Arg Ala Ala Ala Glu Val Ile Asp Gly Ala
                325                 330                 335

Cys Gly Gly Val Gly His Ser Leu Glu Glu Met Glu Thr Tyr Trp Arg
            340                 345                 350

Pro Ile Leu Glu Arg Val Ser Asp Ala Pro Gly Pro Thr Pro Glu Ala
            355                 360                 365

Leu His Ala Leu Gly Arg Ala Glu Trp His Gly Gly Asn Arg Asp Tyr
            370                 375                 380

Thr Gln Leu Trp Lys Pro Ile Ser Val Glu Glu Ile Lys Ala Ser Arg
385                 390                 395                 400

Phe Asp Trp Arg Thr Ser Pro Gly Pro Asp Gly Ile Arg Ser Gly Gln
                405                 410                 415

Trp Arg Ala Val Pro Val His Leu Lys Ala Glu Met Phe Asn Ala Trp
            420                 425                 430

Met Ala Arg Gly Glu Ile Pro Glu Ile Leu Arg Gln Cys Arg Thr Val
            435                 440                 445

Phe Val Pro Lys Val Glu Arg Pro Gly Gly Pro Gly Glu Tyr Arg Pro
450                 455                 460

Ile Ser Ile Ala Ser Ile Pro Leu Arg His Phe His Ser Ile Leu Ala
465                 470                 475                 480

Arg Arg Leu Leu Ala Cys Cys Pro Pro Asp Ala Arg Gln Arg Gly Phe
                485                 490                 495

Ile Cys Ala Asp Gly Thr Leu Glu Asn Ser Ala Val Leu Asp Ala Val
            500                 505                 510

Leu Gly Asp Ser Arg Lys Lys Leu Arg Glu Cys His Val Ala Val Leu
            515                 520                 525

Asp Phe Ala Lys Ala Phe Asp Thr Val Ser His Glu Ala Leu Val Glu
            530                 535                 540

Leu Leu Arg Leu Arg Gly Met Pro Glu Gln Phe Cys Gly Tyr Ile Ala
545                 550                 555                 560

His Leu Tyr Asp Thr Ala Ser Thr Thr Leu Ala Val Asn Asn Glu Met
                565                 570                 575

Ser Ser Pro Val Lys Val Gly Arg Gly Val Arg Gln Gly Asp Pro Leu
            580                 585                 590
```

```
Ser Pro Ile Leu Phe Asn Val Val Met Asp Leu Ile Leu Ala Ser Leu
        595                 600                 605
Pro Glu Arg Val Gly Tyr Arg Leu Glu Met Glu Leu Val Ser Ala Leu
        610                 615                 620
Ala Tyr Ala Asp Asp Leu Val Leu Leu Ala Gly Ser Lys Val Gly Met
625                 630                 635                 640
Gln Glu Ser Ile Ser Ala Val Asp Cys Val Gly Arg Gln Met Gly Leu
                645                 650                 655
Arg Leu Asn Cys Arg Lys Ser Ala Val Leu Ser Met Ile Pro Asp Gly
            660                 665                 670
His Arg Lys Lys His His Tyr Leu Thr Glu Arg Thr Phe Asn Ile Gly
        675                 680                 685
Gly Lys Pro Leu Arg Gln Val Ser Cys Val Glu Arg Trp Arg Tyr Leu
        690                 695                 700
Gly Val Asp Phe Glu Ala Ser Gly Cys Val Thr Leu Glu His Ser Ile
705                 710                 715                 720
Ser Ser Ala Leu Asn Asn Ile Ser Arg Ala Pro Leu Lys Pro Gln Gln
                725                 730                 735
Arg Leu Glu Ile Leu Arg Ala His Leu Ile Pro Arg Phe Gln His Gly
            740                 745                 750
Phe Val Leu Gly Asn Ile Ser Asp Asp Arg Leu Arg Met Leu Asp Val
        755                 760                 765
Gln Ile Arg Lys Ala Val Gly Gln Trp Leu Arg Leu Pro Ala Asp Val
        770                 775                 780
Pro Lys Ala Tyr Tyr His Ala Ala Val Gln Asp Gly Gly Leu Ala Ile
785                 790                 795                 800
Pro Ser Val Arg Ala Thr Ile Pro Asp Leu Ile Val Arg Arg Phe Gly
                805                 810                 815
Gly Leu Asp Ser Ser Pro Trp Ser Val Ala Arg Ala Ala Lys Ser
            820                 825                 830
Asp Lys Ile Arg Lys Leu Arg Trp Ala Trp Lys Gln Leu Arg Arg
        835                 840                 845
Phe Ser Arg Val Asp Ser Thr Thr Gln Arg Pro Ser Val Arg Leu Phe
850                 855                 860
Trp Arg Glu His Leu His Ala Ser Val Asp Gly Arg Glu Leu Arg Glu
865                 870                 875                 880
Ser Thr Arg Thr Pro Thr Ser Thr Lys Trp Ile Arg Glu Arg Cys Ala
                885                 890                 895
Gln Ile Thr Gly Arg Asp Phe Gln Phe Val His Thr His Ile Asn
            900                 905                 910
Ala Leu Pro Ser Arg Ile Arg Gly Ser Arg Gly Arg Gly Gly Gly
        915                 920                 925
Glu Ser Ser Leu Thr Cys Arg Ala Gly Cys Lys Val Arg Glu Thr Thr
930                 935                 940
Ala His Ile Leu Gln Gln Cys His Arg Thr His Gly Arg Ile Leu
945                 950                 955                 960
Arg His Asn Lys Ile Val Ser Phe Val Ala Lys Ala Met Glu Glu Asn
                965                 970                 975
Lys Trp Thr Val Glu Leu Glu Pro Arg Leu Arg Thr Ser Val Gly Leu
            980                 985                 990
Arg Lys Pro Asp Ile Ile Ala Ser Arg Asp Gly Val Gly Val Ile Val
        995                 1000                1005
Asp Val Gln Val Val Ser Gly Gln Arg Ser Leu Asp Glu Leu His
```

```
                1010                1015                1020

Arg Glu Lys Arg Asn Lys Tyr Gly Asn His Gly Glu Leu Val Glu
        1025                1030                1035

Leu Val Ala Gly Arg Leu Gly Leu Pro Lys Ala Glu Cys Val Arg
        1040                1045                1050

Ala Thr Ser Cys Thr Ile Ser Trp Arg Gly Val Trp Ser Leu Thr
        1055                1060                1065

Ser Tyr Lys Glu Leu Arg Ser Ile Ile Gly Leu Arg Glu Pro Thr
        1070                1075                1080

Leu Gln Ile Val Pro Ile Leu Ala Leu Arg Gly Ser His Met Asn
        1085                1090                1095

Trp Thr Arg Phe Asn Gln Met Thr Ser Val Met Gly Gly Gly Val
        1100                1105                1110

Gly

<210> SEQ ID NO 2
<211> LENGTH: 840
<212> TYPE: PRT
<213> ORGANISM: Artificial Sequence
<220> FEATURE:
<223> OTHER INFORMATION: synthetic construct

<400> SEQUENCE: 2

Gly Arg Arg Arg Ala Cys Arg Ala Met Arg Pro Lys Thr Ala Gly Arg
1               5                   10                  15

Arg Asn Asp Leu His Asp Asp Arg Thr Ala Ser Ala His Lys Thr Ser
            20                  25                  30

Arg Gln Lys Arg Arg Ala Glu Tyr Ala Arg Val Gln Glu Leu Tyr Lys
        35                  40                  45

Lys Cys Arg Ser Arg Ala Ala Ala Glu Val Ile Asp Gly Ala Cys Gly
    50                  55                  60

Gly Val Gly His Ser Leu Glu Glu Met Glu Thr Tyr Trp Arg Pro Ile
65                  70                  75                  80

Leu Glu Arg Val Ser Asp Ala Pro Gly Pro Thr Pro Glu Ala Leu His
                85                  90                  95

Ala Leu Gly Arg Ala Glu Trp His Gly Gly Asn Arg Asp Tyr Thr Gln
            100                 105                 110

Leu Trp Lys Pro Ile Ser Val Glu Glu Ile Lys Ala Ser Arg Phe Asp
        115                 120                 125

Trp Arg Thr Ser Pro Gly Pro Asp Gly Ile Arg Ser Gly Gln Trp Arg
    130                 135                 140

Ala Val Pro Val His Leu Lys Ala Glu Met Phe Asn Ala Trp Met Ala
145                 150                 155                 160

Arg Gly Glu Ile Pro Glu Ile Leu Arg Gln Cys Arg Thr Val Phe Val
                165                 170                 175

Pro Lys Val Glu Arg Pro Gly Gly Pro Gly Glu Tyr Arg Pro Ile Ser
            180                 185                 190

Ile Ala Ser Ile Pro Leu Arg His Phe His Ser Ile Leu Ala Arg Arg
        195                 200                 205

Leu Leu Ala Cys Cys Pro Pro Asp Ala Arg Gln Arg Gly Phe Ile Cys
    210                 215                 220

Ala Asp Gly Thr Leu Glu Asn Ser Ala Val Leu Asp Ala Val Leu Gly
225                 230                 235                 240

Asp Ser Arg Lys Lys Leu Arg Glu Cys His Val Ala Val Leu Asp Phe
                245                 250                 255
```

```
Ala Lys Ala Phe Asp Thr Val Ser His Glu Ala Leu Val Glu Leu Leu
            260                 265                 270

Arg Leu Arg Gly Met Pro Glu Gln Phe Cys Gly Tyr Ile Ala His Leu
            275                 280                 285

Tyr Asp Thr Ala Ser Thr Thr Leu Ala Val Asn Asn Glu Met Ser Ser
    290                 295                 300

Pro Val Lys Val Gly Arg Gly Val Arg Gln Gly Asp Pro Leu Ser Pro
305                 310                 315                 320

Ile Leu Phe Asn Val Val Met Asp Leu Ile Leu Ala Ser Leu Pro Glu
                325                 330                 335

Arg Val Gly Tyr Arg Leu Glu Met Glu Leu Val Ser Ala Leu Ala Tyr
            340                 345                 350

Ala Asp Asp Leu Val Leu Leu Ala Gly Ser Lys Val Gly Met Gln Glu
            355                 360                 365

Ser Ile Ser Ala Val Asp Cys Val Gly Arg Gln Met Gly Leu Arg Leu
    370                 375                 380

Asn Cys Arg Lys Ser Ala Val Leu Ser Met Ile Pro Asp Gly His Arg
385                 390                 395                 400

Lys Lys His His Tyr Leu Thr Glu Arg Thr Phe Asn Ile Gly Gly Lys
                405                 410                 415

Pro Leu Arg Gln Val Ser Cys Val Glu Arg Trp Arg Tyr Leu Gly Val
            420                 425                 430

Asp Phe Glu Ala Ser Gly Cys Val Thr Leu Glu His Ser Ile Ser Ser
            435                 440                 445

Ala Leu Asn Asn Ile Ser Arg Ala Pro Leu Lys Pro Gln Gln Arg Leu
            450                 455                 460

Glu Ile Leu Arg Ala His Leu Ile Pro Arg Phe Gln His Gly Phe Val
465                 470                 475                 480

Leu Gly Asn Ile Ser Asp Asp Arg Leu Arg Met Leu Asp Val Gln Ile
                485                 490                 495

Arg Lys Ala Val Gly Gln Trp Leu Arg Leu Pro Ala Asp Val Pro Lys
            500                 505                 510

Ala Tyr Tyr His Ala Ala Val Gln Asp Gly Gly Leu Ala Ile Pro Ser
            515                 520                 525

Val Arg Ala Thr Ile Pro Asp Leu Ile Val Arg Arg Phe Gly Gly Leu
            530                 535                 540

Asp Ser Ser Pro Trp Ser Val Ala Arg Ala Ala Lys Ser Asp Lys
545                 550                 555                 560

Ile Arg Lys Lys Leu Arg Trp Ala Trp Lys Gln Leu Arg Arg Phe Ser
                565                 570                 575

Arg Val Asp Ser Thr Thr Gln Arg Pro Ser Val Arg Leu Phe Trp Arg
            580                 585                 590

Glu His Leu His Ala Ser Val Asp Gly Arg Glu Leu Arg Glu Ser Thr
            595                 600                 605

Arg Thr Pro Thr Ser Thr Lys Trp Ile Arg Glu Arg Cys Ala Gln Ile
            610                 615                 620

Thr Gly Arg Asp Phe Val Gln Phe Val His Thr His Ile Asn Ala Leu
625                 630                 635                 640

Pro Ser Arg Ile Arg Gly Ser Arg Gly Arg Gly Gly Glu Ser
                645                 650                 655

Ser Leu Thr Cys Arg Ala Gly Cys Lys Val Arg Glu Thr Thr Ala His
            660                 665                 670
```

```
Ile Leu Gln Gln Cys His Arg Thr His Gly Gly Arg Ile Leu Arg His
            675                 680                 685

Asn Lys Ile Val Ser Phe Val Ala Lys Ala Met Glu Glu Asn Lys Trp
690                 695                 700

Thr Val Glu Leu Glu Pro Arg Leu Arg Thr Ser Val Gly Leu Arg Lys
705                 710                 715                 720

Pro Ala Ile Ile Ala Ser Arg Asp Gly Val Gly Val Ile Val Asp Val
                725                 730                 735

Gln Val Val Ser Gly Gln Arg Ser Leu Asp Glu Leu His Arg Glu Lys
            740                 745                 750

Arg Asn Lys Tyr Gly Asn His Gly Glu Leu Val Glu Leu Val Ala Gly
        755                 760                 765

Arg Leu Gly Leu Pro Lys Ala Glu Cys Val Arg Ala Thr Ser Cys Thr
770                 775                 780

Ile Ser Trp Arg Gly Val Trp Ser Leu Thr Ser Tyr Lys Glu Leu Arg
785                 790                 795                 800

Ser Ile Ile Gly Leu Arg Glu Pro Thr Leu Gln Ile Val Pro Ile Leu
                805                 810                 815

Ala Leu Arg Gly Ser His Met Asn Trp Thr Arg Phe Asn Gln Met Thr
            820                 825                 830

Ser Val Met Gly Gly Gly Val Gly
        835                 840

<210> SEQ ID NO 3
<211> LENGTH: 1228
<212> TYPE: PRT
<213> ORGANISM: Artificial Sequence
<220> FEATURE:
<223> OTHER INFORMATION: synthetic construct

<400> SEQUENCE: 3

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190
```

```
Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
    290                 295                 300

Leu Lys Ser Tyr Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Ala Ala Gln Thr Ala
            355                 360                 365

Ala Ala Ala Met Gly Arg Arg Ala Cys Arg Ala Met Arg Pro
    370                 375                 380

Lys Thr Ala Gly Arg Arg Asn Asp Leu His Asp Asp Arg Thr Ala Ser
385                 390                 395                 400

Ala His Lys Thr Ser Arg Gln Lys Arg Ala Glu Tyr Ala Arg Val
                405                 410                 415

Gln Glu Leu Tyr Lys Lys Cys Arg Ser Arg Ala Ala Ala Glu Val Ile
                420                 425                 430

Asp Gly Ala Cys Gly Gly Val Gly His Ser Leu Glu Glu Met Glu Thr
            435                 440                 445

Tyr Trp Arg Pro Ile Leu Glu Arg Val Ser Asp Ala Pro Gly Pro Thr
    450                 455                 460

Pro Glu Ala Leu His Ala Leu Gly Arg Ala Glu Trp His Gly Asn
465                 470                 475                 480

Arg Asp Tyr Thr Gln Leu Trp Lys Pro Ile Ser Val Glu Glu Ile Lys
                485                 490                 495

Ala Ser Arg Phe Asp Trp Arg Thr Ser Pro Gly Pro Asp Gly Ile Arg
                500                 505                 510

Ser Gly Gln Trp Arg Ala Val Pro Val His Leu Lys Ala Glu Met Phe
            515                 520                 525

Asn Ala Trp Met Ala Arg Gly Glu Ile Pro Glu Ile Leu Arg Gln Cys
    530                 535                 540

Arg Thr Val Phe Val Pro Lys Val Glu Arg Pro Gly Pro Gly Glu
545                 550                 555                 560

Tyr Arg Pro Ile Ser Ile Ala Ser Ile Pro Leu Arg His Phe His Ser
                565                 570                 575

Ile Leu Ala Arg Arg Leu Leu Ala Cys Cys Pro Pro Asp Ala Arg Gln
                580                 585                 590

Arg Gly Phe Ile Cys Ala Asp Gly Thr Leu Glu Asn Ser Ala Val Leu
            595                 600                 605

Asp Ala Val Leu Gly Asp Ser Arg Lys Lys Leu Arg Glu Cys His Val
```

-continued

```
            610                 615                 620
Ala Val Leu Asp Phe Ala Lys Ala Phe Asp Thr Val Ser His Glu Ala
625                 630                 635                 640

Leu Val Glu Leu Leu Arg Leu Arg Gly Met Pro Glu Gln Phe Cys Gly
                    645                 650                 655

Tyr Ile Ala His Leu Tyr Asp Thr Ala Ser Thr Thr Leu Ala Val Asn
                660                 665                 670

Asn Glu Met Ser Ser Pro Val Lys Val Gly Arg Gly Val Arg Gln Gly
                675                 680                 685

Asp Pro Leu Ser Pro Ile Leu Phe Asn Val Val Met Asp Leu Ile Leu
            690                 695                 700

Ala Ser Leu Pro Glu Arg Val Gly Tyr Arg Leu Glu Met Glu Leu Val
705                 710                 715                 720

Ser Ala Leu Ala Tyr Ala Asp Asp Leu Val Leu Ala Gly Ser Lys
                    725                 730                 735

Val Gly Met Gln Glu Ser Ile Ser Ala Val Asp Cys Val Gly Arg Gln
                740                 745                 750

Met Gly Leu Arg Leu Asn Cys Arg Lys Ser Ala Val Leu Ser Met Ile
                755                 760                 765

Pro Asp Gly His Arg Lys Lys His His Tyr Leu Thr Glu Arg Thr Phe
770                 775                 780

Asn Ile Gly Gly Lys Pro Leu Arg Gln Val Ser Cys Val Glu Arg Trp
785                 790                 795                 800

Arg Tyr Leu Gly Val Asp Phe Glu Ala Ser Gly Cys Val Thr Leu Glu
                    805                 810                 815

His Ser Ile Ser Ser Ala Leu Asn Asn Ile Ser Arg Ala Pro Leu Lys
                820                 825                 830

Pro Gln Gln Arg Leu Glu Ile Leu Arg Ala His Leu Ile Pro Arg Phe
                835                 840                 845

Gln His Gly Phe Val Leu Gly Asn Ile Ser Asp Asp Arg Leu Arg Met
850                 855                 860

Leu Asp Val Gln Ile Arg Lys Ala Val Gly Gln Trp Leu Arg Leu Pro
865                 870                 875                 880

Ala Asp Val Pro Lys Ala Tyr Tyr His Ala Ala Val Gln Asp Gly Gly
                885                 890                 895

Leu Ala Ile Pro Ser Val Arg Ala Thr Ile Pro Asp Leu Ile Val Arg
                900                 905                 910

Arg Phe Gly Gly Leu Asp Ser Ser Pro Trp Ser Val Ala Arg Ala Ala
                915                 920                 925

Ala Lys Ser Asp Lys Ile Arg Lys Lys Leu Arg Trp Ala Trp Lys Gln
930                 935                 940

Leu Arg Arg Phe Ser Arg Val Asp Ser Thr Thr Gln Arg Pro Ser Val
945                 950                 955                 960

Arg Leu Phe Trp Arg Glu His Leu His Ala Ser Val Asp Gly Arg Glu
                    965                 970                 975

Leu Arg Glu Ser Thr Arg Thr Pro Thr Ser Thr Lys Trp Ile Arg Glu
                980                 985                 990

Arg Cys Ala Gln Ile Thr Gly Arg Asp Phe Val Gln Phe Val His Thr
                995                 1000                1005

His Ile Asn Ala Leu Pro Ser Arg Ile Arg Gly Ser Arg Gly Arg
                1010                1015                1020

Arg Gly Gly Gly Glu Ser Ser Leu Thr Cys Arg Ala Gly Cys Lys
                1025                1030                1035
```

```
Val Arg Glu Thr Thr Ala His Ile Leu Gln Gln Cys His Arg Thr
    1040                1045                1050

His Gly Gly Arg Ile Leu Arg His Asn Lys Ile Val Ser Phe Val
    1055                1060                1065

Ala Lys Ala Met Glu Glu Asn Lys Trp Thr Val Glu Leu Glu Pro
    1070                1075                1080

Arg Leu Arg Thr Ser Val Gly Leu Arg Lys Pro Ala Ile Ile Ala
    1085                1090                1095

Ser Arg Asp Gly Val Gly Val Ile Val Asp Val Gln Val Val Ser
    1100                1105                1110

Gly Gln Arg Ser Leu Asp Glu Leu His Arg Glu Lys Arg Asn Lys
    1115                1120                1125

Tyr Gly Asn His Gly Glu Leu Val Glu Leu Val Ala Gly Arg Leu
    1130                1135                1140

Gly Leu Pro Lys Ala Glu Cys Val Arg Ala Thr Ser Cys Thr Ile
    1145                1150                1155

Ser Trp Arg Gly Val Trp Ser Leu Thr Ser Tyr Lys Glu Leu Arg
    1160                1165                1170

Ser Ile Ile Gly Leu Arg Glu Pro Thr Leu Gln Ile Val Pro Ile
    1175                1180                1185

Leu Ala Leu Arg Gly Ser His Met Asn Trp Thr Arg Phe Asn Gln
    1190                1195                1200

Met Thr Ser Val Met Gly Gly Val Gly Glu Asn Leu Tyr Phe
    1205                1210                1215

Gln Ser Gly Ser His His His His His
    1220                1225

<210> SEQ ID NO 4
<211> LENGTH: 427
<212> TYPE: PRT
<213> ORGANISM: Eubacterium rectale

<400> SEQUENCE: 4

Met Asp Thr Ser Asn Leu Met Glu Gln Ile Leu Ser Ser Asp Asn Leu
1               5                   10                  15

Asn Arg Ala Tyr Leu Gln Val Val Arg Asn Lys Gly Ala Glu Gly Val
            20                  25                  30

Asp Gly Met Lys Tyr Thr Glu Leu Lys Glu His Leu Ala Lys Asn Gly
        35                  40                  45

Glu Thr Ile Lys Gly Gln Leu Arg Thr Arg Lys Tyr Lys Pro Gln Pro
    50                  55                  60

Ala Arg Arg Val Glu Ile Pro Lys Pro Asp Gly Gly Val Arg Asn Leu
65                  70                  75                  80

Gly Val Pro Thr Val Thr Asp Arg Phe Ile Gln Gln Ala Ile Ala Gln
                85                  90                  95

Val Leu Thr Pro Ile Tyr Glu Glu Gln Phe His Asp His Ser Tyr Gly
            100                 105                 110

Phe Arg Pro Asn Arg Cys Ala Gln Gln Ala Ile Leu Thr Ala Leu Asn
        115                 120                 125

Ile Met Asn Asp Gly Asn Asp Trp Ile Val Asp Ile Asp Leu Glu Lys
    130                 135                 140

Phe Phe Asp Thr Val Asn His Asp Lys Leu Met Thr Leu Ile Gly Arg
145                 150                 155                 160

Thr Ile Lys Asp Gly Asp Val Ile Ser Ile Val Arg Lys Tyr Leu Val
```

```
            165                 170                 175
Ser Gly Ile Met Ile Asp Asp Glu Tyr Glu Asp Ser Ile Val Gly Thr
            180                 185                 190

Pro Gln Gly Gly Asn Leu Ser Pro Leu Leu Ala Asn Ile Met Leu Asn
        195                 200                 205

Glu Leu Asp Lys Glu Met Glu Lys Arg Gly Leu Asn Phe Val Arg Tyr
    210                 215                 220

Ala Asp Asp Cys Ile Ile Met Val Gly Ser Glu Met Ser Ala Asn Arg
225                 230                 235                 240

Val Met Arg Asn Ile Ser Arg Phe Ile Glu Glu Lys Leu Gly Leu Lys
                245                 250                 255

Val Asn Met Thr Lys Ser Lys Val Asp Arg Pro Ser Gly Leu Lys Tyr
            260                 265                 270

Leu Gly Phe Gly Phe Tyr Phe Asp Pro Arg Ala His Gln Phe Lys Ala
        275                 280                 285

Lys Pro His Ala Lys Ser Val Ala Lys Phe Lys Lys Arg Met Lys Glu
    290                 295                 300

Leu Thr Cys Arg Ser Trp Gly Val Ser Asn Ser Tyr Lys Val Glu Lys
305                 310                 315                 320

Leu Asn Gln Leu Ile Arg Gly Trp Ile Asn Tyr Phe Lys Ile Gly Ser
                325                 330                 335

Met Lys Thr Leu Cys Lys Glu Leu Asp Ser Arg Ile Arg Tyr Arg Leu
            340                 345                 350

Arg Met Cys Ile Trp Lys Gln Trp Lys Thr Pro Gln Asn Gln Glu Lys
        355                 360                 365

Asn Leu Val Lys Leu Gly Ile Asp Arg Asn Thr Ala Arg Arg Val Ala
    370                 375                 380

Tyr Thr Gly Lys Arg Ile Ala Tyr Val Cys Asn Lys Gly Ala Val Asn
385                 390                 395                 400

Val Ala Ile Ser Asn Lys Arg Leu Ala Ser Phe Gly Leu Ile Ser Met
                405                 410                 415

Leu Asp Tyr Tyr Ile Glu Lys Cys Val Thr Cys
            420                 425

<210> SEQ ID NO 5
<211> LENGTH: 1501
<212> TYPE: PRT
<213> ORGANISM: Artificial Sequence
<220> FEATURE:
<223> OTHER INFORMATION: synthetic construct

<400> SEQUENCE: 5

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
```

```
                100                 105                 110
Ala Leu Ser Leu Ile Tyr Asn Lys Asp Leu Pro Asn Pro Lys
            115                 120                 125

Thr Trp Glu Glu Ile Pro Ala Leu Asp Lys Glu Leu Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Ala Ala Ala Gln Thr Ala
        355                 360                 365

Ala Ala Ala Ala Met Met Ala Ser Thr Ala Leu Ser Leu Met Gly Arg
    370                 375                 380

Cys Asn Pro Asp Gly Cys Thr Arg Gly Lys His Val Thr Ala Ala Pro
385                 390                 395                 400

Met Asp Gly Pro Arg Gly Pro Ser Ser Leu Ala Gly Thr Phe Gly Trp
                405                 410                 415

Gly Leu Ala Ile Pro Ala Gly Glu Pro Cys Gly Arg Val Cys Ser Pro
            420                 425                 430

Ala Thr Val Gly Phe Phe Pro Val Ala Lys Lys Ser Asn Lys Glu Asn
        435                 440                 445

Arg Pro Glu Ala Ser Gly Leu Pro Leu Glu Ser Glu Arg Thr Gly Asp
    450                 455                 460

Asn Pro Thr Val Arg Gly Ser Ala Gly Ala Asp Pro Val Gly Gln Asp
465                 470                 475                 480

Ala Pro Gly Trp Thr Cys Gln Phe Cys Glu Arg Thr Phe Ser Thr Asn
                485                 490                 495

Arg Gly Leu Gly Val His Lys Arg Arg Ala His Pro Val Glu Thr Asn
            500                 505                 510

Thr Asp Ala Ala Pro Met Met Val Lys Arg Arg Trp His Gly Glu Glu
        515                 520                 525
```

-continued

```
Ile Asp Leu Leu Ala Arg Thr Glu Ala Arg Leu Leu Ala Glu Arg Gly
    530                 535                 540

Gln Cys Ser Gly Gly Asp Leu Phe Gly Ala Leu Pro Gly Phe Gly Arg
545                 550                 555                 560

Thr Leu Glu Ala Ile Lys Gly Gln Arg Arg Glu Pro Tyr Arg Ala
                565                 570                 575

Leu Val Gln Ala His Leu Ala Arg Phe Gly Ser Gln Pro Gly Pro Ser
            580                 585                 590

Ser Gly Gly Cys Ser Ala Glu Pro Asp Phe Arg Arg Ala Ser Gly Ala
        595                 600                 605

Glu Glu Ala Gly Glu Glu Arg Cys Ala Glu Asp Ala Ala Tyr Asp
610                 615                 620

Pro Ser Ala Val Gly Gln Met Ser Pro Asp Ala Ala Arg Val Leu Ser
625                 630                 635                 640

Glu Leu Leu Glu Gly Ala Gly Arg Arg Ala Cys Arg Ala Met Arg
                645                 650                 655

Pro Lys Thr Ala Gly Arg Arg Asn Asp Leu His Asp Asp Arg Thr Ala
                660                 665                 670

Ser Ala His Lys Thr Ser Arg Gln Lys Arg Ala Glu Tyr Ala Arg
        675                 680                 685

Val Gln Glu Leu Tyr Lys Lys Cys Arg Ser Arg Ala Ala Ala Glu Val
    690                 695                 700

Ile Asp Gly Ala Cys Gly Gly Val Gly His Ser Leu Glu Glu Met Glu
705                 710                 715                 720

Thr Tyr Trp Arg Pro Ile Leu Glu Arg Val Ser Asp Ala Pro Gly Pro
                725                 730                 735

Thr Pro Glu Ala Leu His Ala Leu Gly Arg Ala Glu Trp His Gly Gly
            740                 745                 750

Asn Arg Asp Tyr Thr Gln Leu Trp Lys Pro Ile Ser Val Glu Glu Ile
        755                 760                 765

Lys Ala Ser Arg Phe Asp Trp Arg Thr Ser Pro Gly Pro Asp Gly Ile
770                 775                 780

Arg Ser Gly Gln Trp Arg Ala Val Pro Val His Leu Lys Ala Glu Met
785                 790                 795                 800

Phe Asn Ala Trp Met Ala Arg Gly Glu Ile Pro Glu Ile Leu Arg Gln
                805                 810                 815

Cys Arg Thr Val Phe Val Pro Lys Val Glu Arg Pro Gly Gly Pro Gly
            820                 825                 830

Glu Tyr Arg Pro Ile Ser Ile Ala Ser Ile Pro Leu Arg His Phe His
        835                 840                 845

Ser Ile Leu Ala Arg Arg Leu Leu Ala Cys Cys Pro Pro Asp Ala Arg
850                 855                 860

Gln Arg Gly Phe Ile Cys Ala Asp Gly Thr Leu Glu Asn Ser Ala Val
865                 870                 875                 880

Leu Asp Ala Val Leu Gly Asp Ser Arg Lys Lys Leu Arg Glu Cys His
                885                 890                 895

Val Ala Val Leu Asp Phe Ala Lys Ala Phe Asp Thr Val Ser His Glu
            900                 905                 910

Ala Leu Val Glu Leu Leu Arg Leu Arg Gly Met Pro Glu Gln Phe Cys
        915                 920                 925

Gly Tyr Ile Ala His Leu Tyr Asp Thr Ala Ser Thr Thr Leu Ala Val
930                 935                 940
```

```
Asn Asn Glu Met Ser Ser Pro Val Lys Val Gly Arg Gly Val Arg Gln
945                 950                 955                 960

Gly Asp Pro Leu Ser Pro Ile Leu Phe Asn Val Val Met Asp Leu Ile
            965                 970                 975

Leu Ala Ser Leu Pro Glu Arg Val Gly Tyr Arg Leu Glu Met Glu Leu
            980                 985                 990

Val Ser Ala Leu Ala Tyr Ala Asp  Asp Leu Val Leu Leu  Ala Gly Ser
        995                 1000                1005

Lys Val  Gly Met Gln Glu Ser  Ile Ser Ala Val Asp  Cys Val Gly
    1010                1015                1020

Arg Gln  Met Gly Leu Arg Leu  Asn Cys Arg Lys Ser  Ala Val Leu
    1025                1030                1035

Ser Met  Ile Pro Asp Gly His  Arg Lys His His  Tyr Leu Thr
    1040                1045                1050

Glu Arg  Thr Phe Asn Ile Gly  Gly Lys Pro Leu Arg  Gln Val Ser
    1055                1060                1065

Cys Val  Glu Arg Trp Arg Tyr  Leu Gly Val Asp Phe  Glu Ala Ser
    1070                1075                1080

Gly Cys  Val Thr Leu Glu His  Ser Ile Ser Ser Ala  Leu Asn Asn
    1085                1090                1095

Ile Ser  Arg Ala Pro Leu Lys  Pro Gln Gln Arg Leu  Glu Ile Leu
    1100                1105                1110

Arg Ala  His Leu Ile Pro Arg  Phe Gln His Gly Phe  Val Leu Gly
    1115                1120                1125

Asn Ile  Ser Asp Asp Arg Leu  Arg Met Leu Asp Val  Gln Ile Arg
    1130                1135                1140

Lys Ala  Val Gly Gln Trp Leu  Arg Leu Pro Ala Asp  Val Pro Lys
    1145                1150                1155

Ala Tyr  Tyr His Ala Ala Val  Gln Asp Gly Gly Leu  Ala Ile Pro
    1160                1165                1170

Ser Val  Arg Ala Thr Ile Pro  Asp Leu Ile Val Arg  Arg Phe Gly
    1175                1180                1185

Gly Leu  Asp Ser Ser Pro Trp  Ser Val Ala Arg Ala  Ala Ala Lys
    1190                1195                1200

Ser Asp  Lys Ile Arg Lys Lys  Leu Arg Trp Ala Trp  Lys Gln Leu
    1205                1210                1215

Arg Arg  Phe Ser Arg Val Asp  Ser Thr Thr Gln Arg  Pro Ser Val
    1220                1225                1230

Arg Leu  Phe Trp Arg Glu His  Leu His Ala Ser Val  Asp Gly Arg
    1235                1240                1245

Glu Leu  Arg Glu Ser Thr Arg  Thr Pro Thr Ser Thr  Lys Trp Ile
    1250                1255                1260

Arg Glu  Arg Cys Ala Gln Ile  Thr Gly Arg Asp Phe  Val Gln Phe
    1265                1270                1275

Val His  Thr His Ile Asn Ala  Leu Pro Ser Arg Ile  Arg Gly Ser
    1280                1285                1290

Arg Gly  Arg Arg Gly Gly Gly  Glu Ser Ser Leu Thr  Cys Arg Ala
    1295                1300                1305

Gly Cys  Lys Val Arg Glu Thr  Thr Ala His Ile Leu  Gln Gln Cys
    1310                1315                1320

His Arg  Thr His Gly Gly Arg  Ile Leu Arg His Asn  Lys Ile Val
    1325                1330                1335

Ser Phe  Val Ala Lys Ala Met  Glu Glu Asn Lys Trp  Thr Val Glu
```

```
             1340                1345                1350

Leu Glu Pro Arg Leu Arg Thr Ser Val Gly Leu Arg Lys Pro Asp
        1355                1360                1365

Ile Ile Ala Ser Arg Asp Gly Val Gly Val Ile Val Asp Val Gln
    1370                1375                1380

Val Val Ser Gly Gln Arg Ser Leu Asp Glu Leu His Arg Glu Lys
1385                1390                1395

Arg Asn Lys Tyr Gly Asn His Gly Glu Leu Val Glu Leu Val Ala
        1400                1405                1410

Gly Arg Leu Gly Leu Pro Lys Ala Glu Cys Val Arg Ala Thr Ser
    1415                1420                1425

Cys Thr Ile Ser Trp Arg Gly Val Trp Ser Leu Thr Ser Tyr Lys
1430                1435                1440

Glu Leu Arg Ser Ile Ile Gly Leu Arg Glu Pro Thr Leu Gln Ile
        1445                1450                1455

Val Pro Ile Leu Ala Leu Arg Gly Ser His Met Asn Trp Thr Arg
    1460                1465                1470

Phe Asn Gln Met Thr Ser Val Met Gly Gly Val Gly Glu Asn
1475                1480                1485

Leu Tyr Phe Gln Ser Gly Ser His His His His His
        1490                1495                1500

<210> SEQ ID NO 6
<211> LENGTH: 1433
<212> TYPE: PRT
<213> ORGANISM: Artificial Sequence
<220> FEATURE:
<223> OTHER INFORMATION: synthetic construct

<400> SEQUENCE: 6

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
```

-continued

```
                195                 200                 205
Thr Asp Tyr Ser Ile Ala Glu Ala Ala Phe Asn Lys Gly Glu Thr Ala
210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
                260                 265                 270
Asn Lys Glu Leu Ala Lys Glu Phe Leu Glu Asn Tyr Leu Leu Thr Asp
                275                 280                 285
Glu Gly Leu Glu Ala Val Asn Lys Asp Lys Pro Leu Gly Ala Val Ala
290                 295                 300
Leu Lys Ser Tyr Glu Glu Leu Val Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
                340                 345                 350
Ser Gly Arg Gln Thr Val Asp Glu Ala Leu Ala Ala Ala Gln Thr Ala
                355                 360                 365
Ala Ala Ala Ala Met Lys Lys Ser Asn Lys Glu Asn Arg Pro Glu Ala
370                 375                 380
Ser Gly Leu Pro Leu Glu Ser Glu Arg Thr Gly Asp Asn Pro Thr Val
385                 390                 395                 400
Arg Gly Ser Ala Gly Ala Asp Pro Val Gly Gln Asp Ala Pro Gly Trp
                405                 410                 415
Thr Cys Gln Phe Cys Glu Arg Thr Phe Ser Thr Asn Arg Gly Leu Gly
                420                 425                 430
Val His Lys Arg Arg Ala His Pro Val Glu Thr Asn Thr Asp Ala Ala
                435                 440                 445
Pro Met Met Val Lys Arg Arg Trp His Gly Glu Glu Ile Asp Leu Leu
450                 455                 460
Ala Arg Thr Glu Ala Arg Leu Leu Ala Glu Arg Gly Gln Cys Ser Gly
465                 470                 475                 480
Gly Asp Leu Phe Gly Ala Leu Pro Gly Phe Gly Arg Thr Leu Glu Ala
                485                 490                 495
Ile Lys Gly Gln Arg Arg Glu Pro Tyr Arg Ala Leu Val Gln Ala
                500                 505                 510
His Leu Ala Arg Phe Gly Ser Gln Pro Gly Pro Ser Ser Gly Gly Cys
                515                 520                 525
Ser Ala Glu Pro Asp Phe Arg Arg Ala Ser Gly Ala Glu Glu Ala Gly
                530                 535                 540
Glu Glu Arg Cys Ala Glu Asp Ala Ala Tyr Asp Pro Ser Ala Val
545                 550                 555                 560
Gly Gln Met Ser Pro Asp Ala Ala Arg Val Leu Ser Glu Leu Leu Glu
                565                 570                 575
Gly Ala Gly Arg Arg Ala Cys Arg Ala Met Arg Pro Lys Thr Ala
                580                 585                 590
Gly Arg Arg Asn Asp Leu His Asp Asp Arg Thr Ala Ser Ala His Lys
                595                 600                 605
Thr Ser Arg Gln Lys Arg Ala Glu Tyr Ala Arg Val Gln Glu Leu
610                 615                 620
```

-continued

```
Tyr Lys Lys Cys Arg Ser Arg Ala Ala Glu Val Ile Asp Gly Ala
625                 630                 635                 640

Cys Gly Gly Val Gly His Ser Leu Glu Glu Met Glu Thr Tyr Trp Arg
            645                 650                 655

Pro Ile Leu Glu Arg Val Ser Asp Ala Pro Gly Pro Thr Pro Glu Ala
        660                 665                 670

Leu His Ala Leu Gly Arg Ala Glu Trp His Gly Gly Asn Arg Asp Tyr
            675                 680                 685

Thr Gln Leu Trp Lys Pro Ile Ser Val Glu Glu Ile Lys Ala Ser Arg
690                 695                 700

Phe Asp Trp Arg Thr Ser Pro Gly Pro Asp Gly Ile Arg Ser Gly Gln
705                 710                 715                 720

Trp Arg Ala Val Pro Val His Leu Lys Ala Glu Met Phe Asn Ala Trp
            725                 730                 735

Met Ala Arg Gly Glu Ile Pro Glu Ile Leu Arg Gln Cys Arg Thr Val
            740                 745                 750

Phe Val Pro Lys Val Glu Arg Pro Gly Gly Pro Gly Glu Tyr Arg Pro
        755                 760                 765

Ile Ser Ile Ala Ser Ile Pro Leu Arg His Phe His Ser Ile Leu Ala
770                 775                 780

Arg Arg Leu Leu Ala Cys Cys Pro Pro Asp Ala Arg Gln Arg Gly Phe
785                 790                 795                 800

Ile Cys Ala Asp Gly Thr Leu Glu Asn Ser Ala Val Leu Asp Ala Val
            805                 810                 815

Leu Gly Asp Ser Arg Lys Lys Leu Arg Glu Cys His Val Ala Val Leu
            820                 825                 830

Asp Phe Ala Lys Ala Phe Asp Thr Val Ser His Glu Ala Leu Val Glu
            835                 840                 845

Leu Leu Arg Leu Arg Gly Met Pro Glu Gln Phe Cys Gly Tyr Ile Ala
850                 855                 860

His Leu Tyr Asp Thr Ala Ser Thr Thr Leu Ala Val Asn Asn Glu Met
865                 870                 875                 880

Ser Ser Pro Val Lys Val Gly Arg Gly Val Arg Gln Gly Asp Pro Leu
            885                 890                 895

Ser Pro Ile Leu Phe Asn Val Val Met Asp Leu Ile Leu Ala Ser Leu
        900                 905                 910

Pro Glu Arg Val Gly Tyr Arg Leu Glu Met Glu Leu Val Ser Ala Leu
        915                 920                 925

Ala Tyr Ala Asp Asp Leu Val Leu Leu Ala Gly Ser Lys Val Gly Met
        930                 935                 940

Gln Glu Ser Ile Ser Ala Val Asp Cys Val Gly Arg Gln Met Gly Leu
945                 950                 955                 960

Arg Leu Asn Cys Arg Lys Ser Ala Val Leu Ser Met Ile Pro Asp Gly
            965                 970                 975

His Arg Lys Lys His His Tyr Leu Thr Glu Arg Thr Phe Asn Ile Gly
            980                 985                 990

Gly Lys Pro Leu Arg Gln Val Ser Cys Val Glu Arg Trp Arg Tyr Leu
        995                 1000                1005

Gly Val Asp Phe Glu Ala Ser Gly Cys Val Thr Leu Glu His Ser
        1010                1015                1020

Ile Ser Ser Ala Leu Asn Asn Ile Ser Arg Ala Pro Leu Lys Pro
        1025                1030                1035
```

```
Gln Gln Arg Leu Glu Ile Leu Arg Ala His Leu Ile Pro Arg Phe
    1040                1045                1050

Gln His Gly Phe Val Leu Gly Asn Ile Ser Asp Asp Arg Leu Arg
    1055                1060                1065

Met Leu Asp Val Gln Ile Arg Lys Ala Val Gly Gln Trp Leu Arg
    1070                1075                1080

Leu Pro Ala Asp Val Pro Lys Ala Tyr Tyr His Ala Ala Val Gln
    1085                1090                1095

Asp Gly Gly Leu Ala Ile Pro Ser Val Arg Ala Thr Ile Pro Asp
    1100                1105                1110

Leu Ile Val Arg Arg Phe Gly Gly Leu Asp Ser Ser Pro Trp Ser
    1115                1120                1125

Val Ala Arg Ala Ala Ala Lys Ser Asp Lys Ile Arg Lys Lys Leu
    1130                1135                1140

Arg Trp Ala Trp Lys Gln Leu Arg Arg Phe Ser Arg Val Asp Ser
    1145                1150                1155

Thr Thr Gln Arg Pro Ser Val Arg Leu Phe Trp Arg Glu His Leu
    1160                1165                1170

His Ala Ser Val Asp Gly Arg Glu Leu Arg Glu Ser Thr Arg Thr
    1175                1180                1185

Pro Thr Ser Thr Lys Trp Ile Arg Glu Arg Cys Ala Gln Ile Thr
    1190                1195                1200

Gly Arg Asp Phe Val Gln Phe Val His Thr His Ile Asn Ala Leu
    1205                1210                1215

Pro Ser Arg Ile Arg Gly Ser Arg Gly Arg Gly Gly Gly Glu
    1220                1225                1230

Ser Ser Leu Thr Cys Arg Ala Gly Cys Lys Val Arg Glu Thr Thr
    1235                1240                1245

Ala His Ile Leu Gln Gln Cys His Arg Thr His Gly Gly Arg Ile
    1250                1255                1260

Leu Arg His Asn Lys Ile Val Ser Phe Val Ala Lys Ala Met Glu
    1265                1270                1275

Glu Asn Lys Trp Thr Val Glu Leu Glu Pro Arg Leu Arg Thr Ser
    1280                1285                1290

Val Gly Leu Arg Lys Pro Asp Ile Ile Ala Ser Arg Asp Gly Val
    1295                1300                1305

Gly Val Ile Val Asp Val Gln Val Val Ser Gly Gln Arg Ser Leu
    1310                1315                1320

Asp Glu Leu His Arg Glu Lys Arg Asn Lys Tyr Gly Asn His Gly
    1325                1330                1335

Glu Leu Val Glu Leu Val Ala Gly Arg Leu Gly Leu Pro Lys Ala
    1340                1345                1350

Glu Cys Val Arg Ala Thr Ser Cys Thr Ile Ser Trp Arg Gly Val
    1355                1360                1365

Trp Ser Leu Thr Ser Tyr Lys Glu Leu Arg Ser Ile Ile Gly Leu
    1370                1375                1380

Arg Glu Pro Thr Leu Gln Ile Val Pro Ile Leu Ala Leu Arg Gly
    1385                1390                1395

Ser His Met Asn Trp Thr Arg Phe Asn Gln Met Thr Ser Val Met
    1400                1405                1410

Gly Gly Gly Val Gly Glu Asn Leu Tyr Phe Gln Ser Gly Ser His
    1415                1420                1425

His His His His
```

-continued

1430

<210> SEQ ID NO 7
<211> LENGTH: 1228
<212> TYPE: PRT
<213> ORGANISM: Artificial Sequence
<220> FEATURE:
<223> OTHER INFORMATION: synthetic construct

<400> SEQUENCE: 7

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Ala Ala Ala Gln Thr Ala
```

-continued

```
                355                 360                 365
Ala Ala Ala Ala Met Gly Arg Arg Ala Cys Arg Ala Met Arg Pro
            370                 375                 380
Lys Thr Ala Gly Arg Arg Asn Asp Leu His Asp Asp Arg Thr Ala Ser
385                     390                 395                 400
Ala His Lys Thr Ser Arg Gln Lys Arg Arg Ala Glu Tyr Ala Arg Val
                    405                 410                 415
Gln Glu Leu Tyr Lys Lys Cys Arg Ser Arg Ala Ala Glu Val Ile
                420                 425                 430
Asp Gly Ala Cys Gly Gly Val Gly His Ser Leu Glu Glu Met Glu Thr
            435                 440                 445
Tyr Trp Arg Pro Ile Leu Glu Arg Val Ser Asp Ala Pro Gly Pro Thr
        450                 455                 460
Pro Glu Ala Leu His Ala Leu Gly Arg Ala Glu Trp His Gly Gly Asn
465                 470                 475                 480
Arg Asp Tyr Thr Gln Leu Trp Lys Pro Ile Ser Val Glu Glu Ile Lys
                    485                 490                 495
Ala Ser Arg Phe Asp Trp Arg Thr Ser Pro Gly Pro Asp Gly Ile Arg
                500                 505                 510
Ser Gly Gln Trp Arg Ala Val Pro Val His Leu Lys Ala Glu Met Phe
            515                 520                 525
Asn Ala Trp Met Ala Arg Gly Glu Ile Pro Glu Ile Leu Arg Gln Cys
        530                 535                 540
Arg Thr Val Phe Val Pro Lys Val Glu Arg Pro Gly Gly Pro Gly Glu
545                 550                 555                 560
Tyr Arg Pro Ile Ser Ile Ala Ser Ile Pro Leu Arg His Phe His Ser
                    565                 570                 575
Ile Leu Ala Arg Arg Leu Leu Ala Cys Cys Pro Pro Asp Ala Arg Gln
                580                 585                 590
Arg Gly Phe Ile Cys Ala Asp Gly Thr Leu Glu Asn Ser Ala Val Leu
            595                 600                 605
Asp Ala Val Leu Gly Asp Ser Arg Lys Lys Leu Arg Glu Cys His Val
        610                 615                 620
Ala Val Leu Asp Phe Ala Lys Ala Phe Asp Thr Val Ser His Glu Ala
625                 630                 635                 640
Leu Val Glu Leu Leu Arg Leu Arg Gly Met Pro Glu Gln Phe Cys Gly
                    645                 650                 655
Tyr Ile Ala His Leu Tyr Asp Thr Ala Ser Thr Thr Leu Ala Val Asn
                660                 665                 670
Asn Glu Met Ser Ser Pro Val Lys Val Gly Arg Gly Val Arg Gln Gly
            675                 680                 685
Asp Pro Leu Ser Pro Ile Leu Phe Asn Val Val Met Asp Leu Ile Leu
        690                 695                 700
Ala Ser Leu Pro Glu Arg Val Gly Tyr Arg Leu Glu Met Glu Leu Val
705                 710                 715                 720
Ser Ala Leu Ala Tyr Ala Asp Asp Leu Val Leu Leu Ala Gly Ser Lys
                    725                 730                 735
Val Gly Met Gln Glu Ser Ile Ser Ala Val Asp Cys Val Gly Arg Gln
                740                 745                 750
Met Gly Leu Arg Leu Asn Cys Arg Lys Ser Ala Val Leu Ser Met Ile
            755                 760                 765
Pro Asp Gly His Arg Lys Lys His His Tyr Leu Thr Glu Arg Thr Phe
        770                 775                 780
```

```
Asn Ile Gly Gly Lys Pro Leu Arg Gln Val Ser Cys Val Glu Arg Trp
785                 790                 795                 800

Arg Tyr Leu Gly Val Asp Phe Glu Ala Ser Gly Cys Val Thr Leu Glu
            805                 810                 815

His Ser Ile Ser Ser Ala Leu Asn Asn Ile Ser Arg Ala Pro Leu Lys
                820                 825                 830

Pro Gln Gln Arg Leu Glu Ile Leu Arg Ala His Leu Ile Pro Arg Phe
            835                 840                 845

Gln His Gly Phe Val Leu Gly Asn Ile Ser Asp Asp Arg Leu Arg Met
        850                 855                 860

Leu Asp Val Gln Ile Arg Lys Ala Val Gly Gln Trp Leu Arg Leu Pro
865                 870                 875                 880

Ala Asp Val Pro Lys Ala Tyr Tyr His Ala Ala Val Gln Asp Gly Gly
                885                 890                 895

Leu Ala Ile Pro Ser Val Arg Ala Thr Ile Pro Asp Leu Ile Val Arg
            900                 905                 910

Arg Phe Gly Gly Leu Asp Ser Ser Pro Trp Ser Val Ala Arg Ala Ala
        915                 920                 925

Ala Lys Ser Asp Lys Ile Arg Lys Lys Leu Arg Trp Ala Trp Lys Gln
    930                 935                 940

Leu Arg Arg Phe Ser Arg Val Asp Ser Thr Thr Gln Arg Pro Ser Val
945                 950                 955                 960

Arg Leu Phe Trp Arg Glu His Leu His Ala Ser Val Asp Gly Arg Glu
                965                 970                 975

Leu Arg Glu Ser Thr Arg Thr Pro Thr Ser Thr Lys Trp Ile Arg Glu
            980                 985                 990

Arg Cys Ala Gln Ile Thr Gly Arg Asp Phe Val Gln Phe Val His Thr
        995                 1000                1005

His Ile Asn Ala Leu Pro Ser Arg Ile Arg Gly Ser Arg Gly Arg
   1010                1015                1020

Arg Gly Gly Gly Glu Ser Ser Leu Thr Cys Arg Ala Gly Cys Lys
   1025                1030                1035

Val Arg Glu Thr Thr Ala His Ile Leu Gln Gln Cys His Arg Thr
   1040                1045                1050

His Gly Gly Arg Ile Leu Arg His Asn Lys Ile Val Ser Phe Val
   1055                1060                1065

Ala Lys Ala Met Glu Glu Asn Lys Trp Thr Val Glu Leu Glu Pro
   1070                1075                1080

Arg Leu Arg Thr Ser Val Gly Leu Arg Lys Pro Asp Ile Ile Ala
   1085                1090                1095

Ser Arg Asp Gly Val Gly Val Ile Val Asp Val Gln Val Val Ser
   1100                1105                1110

Gly Gln Arg Ser Leu Asp Glu Leu His Arg Glu Lys Arg Asn Lys
   1115                1120                1125

Tyr Gly Asn His Gly Glu Leu Val Glu Leu Val Ala Gly Arg Leu
   1130                1135                1140

Gly Leu Pro Lys Ala Glu Cys Val Arg Ala Thr Ser Cys Thr Ile
   1145                1150                1155

Ser Trp Arg Gly Val Trp Ser Leu Thr Ser Tyr Lys Glu Leu Arg
   1160                1165                1170

Ser Ile Ile Gly Leu Arg Glu Pro Thr Leu Gln Ile Val Pro Ile
   1175                1180                1185
```

```
Leu Ala  Leu Arg Gly Ser His  Met Asn Trp Thr Arg  Phe Asn Gln
    1190             1195                1200

Met Thr  Ser Val Met Gly Gly  Val Gly Glu Asn  Leu Tyr Phe
    1205             1210                1215

Gln Ser  Gly Ser His His  His His His
    1220             1225
```

<210> SEQ ID NO 8
<211> LENGTH: 814
<212> TYPE: PRT
<213> ORGANISM: Artificial Sequence
<220> FEATURE:
<223> OTHER INFORMATION: synthetic construct

<400> SEQUENCE: 8

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Val Lys Asp Pro Arg Ile Ala Ala
305                 310                 315                 320
```

```
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
            340                 345                 350
Ser Gly Arg Gln Thr Val Asp Glu Ala Leu Ala Ala Gln Thr Ala
        355                 360                 365
Ala Ala Ala Ala Met Asp Thr Ser Asn Leu Met Glu Gln Ile Leu Ser
    370                 375                 380
Ser Asp Asn Leu Asn Arg Ala Tyr Leu Gln Val Val Arg Asn Lys Gly
385                 390                 395                 400
Ala Glu Gly Val Asp Gly Met Lys Tyr Thr Glu Leu Lys Glu His Leu
                405                 410                 415
Ala Lys Asn Gly Glu Thr Ile Lys Gly Gln Leu Arg Thr Arg Lys Tyr
            420                 425                 430
Lys Pro Gln Pro Ala Arg Arg Val Glu Ile Pro Lys Pro Asp Gly Gly
        435                 440                 445
Val Arg Asn Leu Gly Val Pro Thr Val Thr Asp Arg Phe Ile Gln Gln
    450                 455                 460
Ala Ile Ala Gln Val Leu Thr Pro Ile Tyr Glu Glu Gln Phe His Asp
465                 470                 475                 480
His Ser Tyr Gly Phe Arg Pro Asn Arg Cys Ala Gln Gln Ala Ile Leu
                485                 490                 495
Thr Ala Leu Asn Ile Met Asn Asp Gly Asn Asp Trp Ile Val Asp Ile
            500                 505                 510
Asp Leu Glu Lys Phe Phe Asp Thr Val Asn His Asp Lys Leu Met Thr
        515                 520                 525
Leu Ile Gly Arg Thr Ile Lys Asp Gly Asp Val Ile Ser Ile Val Arg
    530                 535                 540
Lys Tyr Leu Val Ser Gly Ile Met Ile Asp Asp Glu Tyr Glu Asp Ser
545                 550                 555                 560
Ile Val Gly Thr Pro Gln Gly Gly Asn Leu Ser Pro Leu Leu Ala Asn
                565                 570                 575
Ile Met Leu Asn Glu Leu Asp Lys Glu Met Glu Lys Arg Gly Leu Asn
            580                 585                 590
Phe Val Arg Tyr Ala Asp Asp Cys Ile Ile Met Val Gly Ser Glu Met
        595                 600                 605
Ser Ala Asn Arg Val Met Arg Asn Ile Ser Arg Phe Ile Glu Glu Lys
    610                 615                 620
Leu Gly Leu Lys Val Asn Met Thr Lys Ser Lys Val Asp Arg Pro Ser
625                 630                 635                 640
Gly Leu Lys Tyr Leu Gly Phe Gly Phe Tyr Phe Asp Pro Arg Ala His
                645                 650                 655
Gln Phe Lys Ala Lys Pro His Ala Lys Ser Val Ala Lys Phe Lys Lys
            660                 665                 670
Arg Met Lys Glu Leu Thr Cys Arg Ser Trp Gly Val Ser Asn Ser Tyr
        675                 680                 685
Lys Val Glu Lys Leu Asn Gln Leu Ile Arg Gly Trp Ile Asn Tyr Phe
    690                 695                 700
Lys Ile Gly Ser Met Lys Thr Leu Cys Lys Glu Leu Asp Ser Arg Ile
705                 710                 715                 720
Arg Tyr Arg Leu Arg Met Cys Ile Trp Lys Gln Trp Lys Thr Pro Gln
                725                 730                 735
Asn Gln Glu Lys Asn Leu Val Lys Leu Gly Ile Asp Arg Asn Thr Ala
```

```
                    740                 745                 750
Arg Arg Val Ala Tyr Thr Gly Lys Arg Ile Ala Tyr Val Cys Asn Lys
                755                 760                 765

Gly Ala Val Asn Val Ala Ile Ser Asn Lys Arg Leu Ala Ser Phe Gly
        770                 775                 780

Leu Ile Ser Met Leu Asp Tyr Tyr Ile Glu Lys Cys Val Thr Cys Glu
785                 790                 795                 800

Asn Leu Tyr Phe Gln Ser Gly Ser His His His His His His
                805                 810

<210> SEQ ID NO 9
<211> LENGTH: 1045
<212> TYPE: PRT
<213> ORGANISM: Bombyx mori

<400> SEQUENCE: 9

Lys Lys Ser Asn Lys Glu Asn Arg Pro Glu Ala Ser Gly Leu Pro Leu
1               5                   10                  15

Glu Ser Glu Arg Thr Gly Asp Asn Pro Thr Val Arg Gly Ser Ala Gly
            20                  25                  30

Ala Asp Pro Val Gly Gln Asp Ala Pro Gly Trp Thr Cys Gln Phe Cys
        35                  40                  45

Glu Arg Thr Phe Ser Thr Asn Arg Gly Leu Gly Val His Lys Arg Arg
50                  55                  60

Ala His Pro Val Glu Thr Asn Thr Asp Ala Ala Pro Met Met Val Lys
65                  70                  75                  80

Arg Arg Trp His Gly Glu Ile Asp Leu Leu Ala Arg Thr Glu Ala
                85                  90                  95

Arg Leu Leu Ala Glu Arg Gly Gln Cys Ser Gly Gly Asp Leu Phe Gly
            100                 105                 110

Ala Leu Pro Gly Phe Gly Arg Thr Leu Glu Ala Ile Lys Gly Gln Arg
        115                 120                 125

Arg Arg Glu Pro Tyr Arg Ala Leu Val Gln Ala His Leu Ala Arg Phe
130                 135                 140

Gly Ser Gln Pro Gly Pro Ser Gly Gly Cys Ser Ala Glu Pro Asp
145                 150                 155                 160

Phe Arg Arg Ala Ser Gly Ala Glu Glu Ala Gly Glu Arg Cys Ala
                165                 170                 175

Glu Asp Ala Ala Ala Tyr Asp Pro Ser Ala Val Gly Gln Met Ser Pro
            180                 185                 190

Asp Ala Ala Arg Val Leu Ser Glu Leu Leu Glu Gly Ala Gly Arg Arg
        195                 200                 205

Arg Ala Cys Arg Ala Met Arg Pro Lys Thr Ala Gly Arg Arg Asn Asp
210                 215                 220

Leu His Asp Asp Arg Thr Ala Ser Ala His Lys Thr Ser Arg Gln Lys
225                 230                 235                 240

Arg Arg Ala Glu Tyr Ala Arg Val Gln Glu Leu Tyr Lys Lys Cys Arg
                245                 250                 255

Ser Arg Ala Ala Ala Glu Val Ile Asp Gly Ala Cys Gly Gly Val Gly
            260                 265                 270

His Ser Leu Glu Glu Met Glu Thr Tyr Trp Arg Pro Ile Leu Glu Arg
        275                 280                 285

Val Ser Asp Ala Pro Gly Pro Thr Pro Glu Ala Leu His Ala Leu Gly
        290                 295                 300
```

```
Arg Ala Glu Trp His Gly Gly Asn Arg Asp Tyr Thr Gln Leu Trp Lys
305                 310                 315                 320

Pro Ile Ser Val Glu Glu Ile Lys Ala Ser Arg Phe Asp Trp Arg Thr
                325                 330                 335

Ser Pro Gly Pro Asp Gly Ile Arg Ser Gly Gln Trp Arg Ala Val Pro
                340                 345                 350

Val His Leu Lys Ala Glu Met Phe Asn Ala Trp Met Ala Arg Gly Glu
                355                 360                 365

Ile Pro Glu Ile Leu Arg Gln Cys Arg Thr Val Phe Val Pro Lys Val
370                 375                 380

Glu Arg Pro Gly Gly Pro Gly Glu Tyr Arg Pro Ile Ser Ile Ala Ser
385                 390                 395                 400

Ile Pro Leu Arg His Phe His Ser Ile Leu Ala Arg Arg Leu Leu Ala
                405                 410                 415

Cys Cys Pro Pro Asp Ala Arg Gln Arg Gly Phe Ile Cys Ala Asp Gly
                420                 425                 430

Thr Leu Glu Asn Ser Ala Val Leu Asp Ala Val Leu Gly Asp Ser Arg
                435                 440                 445

Lys Lys Leu Arg Glu Cys His Val Ala Val Leu Asp Phe Ala Lys Ala
            450                 455                 460

Phe Asp Thr Val Ser His Glu Ala Leu Val Glu Leu Arg Leu Arg
465                 470                 475                 480

Gly Met Pro Glu Gln Phe Cys Gly Tyr Ile Ala His Leu Tyr Asp Thr
                485                 490                 495

Ala Ser Thr Thr Leu Ala Val Asn Asn Glu Met Ser Ser Pro Val Lys
                500                 505                 510

Val Gly Arg Gly Val Arg Gln Gly Asp Pro Leu Ser Pro Ile Leu Phe
            515                 520                 525

Asn Val Val Met Asp Leu Ile Leu Ala Ser Leu Pro Glu Arg Val Gly
530                 535                 540

Tyr Arg Leu Glu Met Glu Leu Val Ser Ala Leu Ala Tyr Ala Asp Asp
545                 550                 555                 560

Leu Val Leu Leu Ala Gly Ser Lys Val Gly Met Gln Glu Ser Ile Ser
                565                 570                 575

Ala Val Asp Cys Val Gly Arg Gln Met Gly Leu Arg Leu Asn Cys Arg
                580                 585                 590

Lys Ser Ala Val Leu Ser Met Ile Pro Asp Gly His Arg Lys Lys His
            595                 600                 605

His Tyr Leu Thr Glu Arg Thr Phe Asn Ile Gly Gly Lys Pro Leu Arg
610                 615                 620

Gln Val Ser Cys Val Glu Arg Trp Arg Tyr Leu Gly Val Asp Phe Glu
625                 630                 635                 640

Ala Ser Gly Cys Val Thr Leu Glu His Ser Ile Ser Ser Ala Leu Asn
                645                 650                 655

Asn Ile Ser Arg Ala Pro Leu Lys Pro Gln Gln Arg Leu Glu Ile Leu
            660                 665                 670

Arg Ala His Leu Ile Pro Arg Phe Gln His Gly Phe Val Leu Gly Asn
            675                 680                 685

Ile Ser Asp Asp Arg Leu Arg Met Leu Asp Val Gln Ile Arg Lys Ala
            690                 695                 700

Val Gly Gln Trp Leu Arg Leu Pro Ala Asp Val Pro Lys Ala Tyr Tyr
705                 710                 715                 720

His Ala Ala Val Gln Asp Gly Gly Leu Ala Ile Pro Ser Val Arg Ala
```

```
                    725                 730                 735
Thr Ile Pro Asp Leu Ile Val Arg Arg Phe Gly Gly Leu Asp Ser Ser
                740                 745                 750

Pro Trp Ser Val Ala Arg Ala Ala Lys Ser Asp Lys Ile Arg Lys
            755                 760                 765

Lys Leu Arg Trp Ala Trp Lys Gln Leu Arg Arg Phe Ser Arg Val Asp
        770                 775                 780

Ser Thr Thr Gln Arg Pro Ser Val Arg Leu Phe Trp Arg Glu His Leu
785                 790                 795                 800

His Ala Ser Val Asp Gly Arg Glu Leu Arg Glu Ser Arg Thr Pro
            805                 810                 815

Thr Ser Thr Lys Trp Ile Arg Glu Arg Cys Ala Gln Ile Thr Gly Arg
                820                 825                 830

Asp Phe Val Gln Phe Val His Thr His Ile Asn Ala Leu Pro Ser Arg
            835                 840                 845

Ile Arg Gly Ser Arg Gly Arg Gly Gly Glu Ser Ser Leu Thr
850                 855                 860

Cys Arg Ala Gly Cys Lys Val Arg Glu Thr Thr Ala His Ile Leu Gln
865                 870                 875                 880

Gln Cys His Arg Thr His Gly Gly Arg Ile Leu Arg His Asn Lys Ile
                885                 890                 895

Val Ser Phe Val Ala Lys Ala Met Glu Glu Asn Lys Trp Thr Val Glu
            900                 905                 910

Leu Glu Pro Arg Leu Arg Thr Ser Val Gly Leu Arg Lys Pro Asp Ile
        915                 920                 925

Ile Ala Ser Arg Asp Gly Val Gly Val Ile Val Asp Val Gln Val Val
    930                 935                 940

Ser Gly Gln Arg Ser Leu Asp Glu Leu His Arg Glu Leu Arg Asn Lys
945                 950                 955                 960

Tyr Gly Asn His Gly Glu Leu Val Glu Leu Val Ala Gly Arg Leu Gly
                965                 970                 975

Leu Pro Lys Ala Glu Cys Val Arg Ala Thr Ser Cys Thr Ile Ser Trp
            980                 985                 990

Arg Gly Val Trp Ser Leu Thr Ser Tyr Lys Glu Leu Arg Ser Ile Ile
        995                1000                1005

Gly Leu Arg Glu Pro Thr Leu Gln Ile Val Pro Ile Leu Ala Leu
    1010                1015                1020

Arg Gly Ser His Met Asn Trp Thr Arg Phe Asn Gln Met Thr Ser
    1025                1030                1035

Val Met Gly Gly Gly Val Gly
    1040                1045
```

<210> SEQ ID NO 10
<211> LENGTH: 840
<212> TYPE: PRT
<213> ORGANISM: Bombyx mori

<400> SEQUENCE: 10

```
Gly Arg Arg Arg Ala Cys Arg Ala Met Arg Pro Lys Thr Ala Gly Arg
1               5                  10                  15

Arg Asn Asp Leu His Asp Asp Arg Thr Ala Ser Ala His Lys Thr Ser
                20                  25                  30

Arg Gln Lys Arg Ala Glu Tyr Ala Arg Val Gln Glu Leu Tyr Lys
            35                  40                  45
```

-continued

```
Lys Cys Arg Ser Arg Ala Ala Glu Val Ile Asp Gly Ala Cys Gly
 50                  55                  60
Gly Val Gly His Ser Leu Glu Glu Met Glu Thr Tyr Trp Arg Pro Ile
 65                  70                  75                  80
Leu Glu Arg Val Ser Asp Ala Pro Gly Pro Thr Pro Glu Ala Leu His
                 85                  90                  95
Ala Leu Gly Arg Ala Glu Trp His Gly Gly Asn Arg Asp Tyr Thr Gln
            100                 105                 110
Leu Trp Lys Pro Ile Ser Val Glu Ile Lys Ala Ser Arg Phe Asp
        115                 120                 125
Trp Arg Thr Ser Pro Gly Pro Asp Gly Ile Arg Ser Gly Gln Trp Arg
    130                 135                 140
Ala Val Pro Val His Leu Lys Ala Glu Met Phe Asn Ala Trp Met Ala
145                 150                 155                 160
Arg Gly Glu Ile Pro Glu Ile Leu Arg Gln Cys Arg Thr Val Phe Val
                165                 170                 175
Pro Lys Val Glu Arg Pro Gly Gly Pro Gly Tyr Arg Pro Ile Ser
            180                 185                 190
Ile Ala Ser Ile Pro Leu Arg His Phe His Ser Ile Leu Ala Arg Arg
        195                 200                 205
Leu Leu Ala Cys Cys Pro Pro Asp Ala Arg Gln Arg Gly Phe Ile Cys
210                 215                 220
Ala Asp Gly Thr Leu Glu Asn Ser Ala Val Leu Asp Ala Val Leu Gly
225                 230                 235                 240
Asp Ser Arg Lys Lys Leu Arg Glu Cys His Val Ala Val Leu Asp Phe
                245                 250                 255
Ala Lys Ala Phe Asp Thr Val Ser His Glu Ala Leu Val Glu Leu Leu
            260                 265                 270
Arg Leu Arg Gly Met Pro Glu Gln Phe Cys Gly Tyr Ile Ala His Leu
        275                 280                 285
Tyr Asp Thr Ala Ser Thr Thr Leu Ala Val Asn Asn Glu Met Ser Ser
    290                 295                 300
Pro Val Lys Val Gly Arg Gly Val Arg Gln Gly Asp Pro Leu Ser Pro
305                 310                 315                 320
Ile Leu Phe Asn Val Val Met Asp Leu Ile Leu Ala Ser Leu Pro Glu
                325                 330                 335
Arg Val Gly Tyr Arg Leu Glu Met Glu Leu Val Ser Ala Leu Ala Tyr
            340                 345                 350
Ala Asp Asp Leu Val Leu Leu Ala Gly Ser Lys Val Gly Met Gln Glu
        355                 360                 365
Ser Ile Ser Ala Val Asp Cys Val Gly Arg Gln Met Gly Leu Arg Leu
    370                 375                 380
Asn Cys Arg Lys Ser Ala Val Leu Ser Met Ile Pro Asp Gly His Arg
385                 390                 395                 400
Lys Lys His His Tyr Leu Thr Glu Arg Thr Phe Asn Ile Gly Gly Lys
                405                 410                 415
Pro Leu Arg Gln Val Ser Cys Val Glu Arg Trp Arg Tyr Leu Gly Val
            420                 425                 430
Asp Phe Glu Ala Ser Gly Cys Val Thr Leu Glu His Ser Ile Ser Ser
        435                 440                 445
Ala Leu Asn Asn Ile Ser Arg Ala Pro Leu Lys Pro Gln Gln Arg Leu
    450                 455                 460
Glu Ile Leu Arg Ala His Leu Ile Pro Arg Phe Gln His Gly Phe Val
```

```
                465                 470                 475                 480
Leu Gly Asn Ile Ser Asp Asp Arg Leu Arg Met Leu Asp Val Gln Ile
                    485                 490                 495
Arg Lys Ala Val Gly Gln Trp Leu Arg Leu Pro Ala Asp Val Pro Lys
            500                 505                 510
Ala Tyr Tyr His Ala Ala Val Gln Asp Gly Leu Ala Ile Pro Ser
        515                 520                 525
Val Arg Ala Thr Ile Pro Asp Leu Ile Val Arg Phe Gly Gly Leu
    530                 535                 540
Asp Ser Ser Pro Trp Ser Val Ala Arg Ala Ala Lys Ser Asp Lys
545                 550                 555                 560
Ile Arg Lys Lys Leu Arg Trp Ala Trp Lys Gln Leu Arg Arg Phe Ser
                565                 570                 575
Arg Val Asp Ser Thr Thr Gln Arg Pro Ser Val Arg Leu Phe Trp Arg
            580                 585                 590
Glu His Leu His Ala Ser Val Asp Gly Arg Glu Leu Arg Glu Ser Thr
        595                 600                 605
Arg Thr Pro Thr Ser Thr Lys Trp Ile Arg Glu Arg Cys Ala Gln Ile
    610                 615                 620
Thr Gly Arg Asp Phe Val Gln Phe Val His Thr His Ile Asn Ala Leu
625                 630                 635                 640
Pro Ser Arg Ile Arg Gly Ser Arg Gly Arg Gly Gly Glu Ser
                645                 650                 655
Ser Leu Thr Cys Arg Ala Gly Cys Lys Val Arg Glu Thr Thr Ala His
            660                 665                 670
Ile Leu Gln Gln Cys His Arg Thr His Gly Gly Arg Ile Leu Arg His
        675                 680                 685
Asn Lys Ile Val Ser Phe Val Ala Lys Ala Met Glu Glu Asn Lys Trp
    690                 695                 700
Thr Val Glu Leu Glu Pro Arg Leu Arg Thr Ser Val Gly Leu Arg Lys
705                 710                 715                 720
Pro Asp Ile Ile Ala Ser Arg Asp Gly Val Gly Val Ile Val Asp Val
                725                 730                 735
Gln Val Val Ser Gly Gln Arg Ser Leu Asp Glu Leu His Arg Glu Lys
            740                 745                 750
Arg Asn Lys Tyr Gly Asn His Gly Glu Leu Val Glu Leu Val Ala Gly
        755                 760                 765
Arg Leu Gly Leu Pro Lys Ala Glu Cys Val Arg Ala Thr Ser Cys Thr
    770                 775                 780
Ile Ser Trp Arg Gly Val Trp Ser Leu Thr Ser Tyr Lys Glu Leu Arg
785                 790                 795                 800
Ser Ile Ile Gly Leu Arg Glu Pro Thr Leu Gln Ile Val Pro Ile Leu
                805                 810                 815
Ala Leu Arg Gly Ser His Met Asn Trp Thr Arg Phe Asn Gln Met Thr
            820                 825                 830
Ser Val Met Gly Gly Gly Val Gly
        835                 840

<210> SEQ ID NO 11
<211> LENGTH: 811
<212> TYPE: PRT
<213> ORGANISM: Artificial Sequence
<220> FEATURE:
<223> OTHER INFORMATION: synthetic construct
```

```
<400> SEQUENCE: 11

Lys Thr Ser Arg Gln Lys Arg Ala Glu Tyr Ala Arg Val Gln Glu
1               5                   10                  15

Leu Tyr Lys Lys Cys Arg Ser Arg Ala Ala Glu Val Ile Asp Gly
            20                  25                  30

Ala Cys Gly Gly Val Gly His Ser Leu Glu Glu Met Glu Thr Tyr Trp
        35                  40                  45

Arg Pro Ile Leu Glu Arg Val Ser Asp Ala Pro Gly Pro Thr Pro Glu
    50                  55                  60

Ala Leu His Ala Leu Gly Arg Ala Glu Trp His Gly Gly Asn Arg Asp
65                  70                  75                  80

Tyr Thr Gln Leu Trp Lys Pro Ile Ser Val Glu Glu Ile Lys Ala Ser
                85                  90                  95

Arg Phe Asp Trp Arg Thr Ser Pro Gly Pro Asp Gly Ile Arg Ser Gly
            100                 105                 110

Gln Trp Arg Ala Val Pro Val His Leu Lys Ala Glu Met Phe Asn Ala
        115                 120                 125

Trp Met Ala Arg Gly Glu Ile Pro Glu Ile Leu Arg Gln Cys Arg Thr
130                 135                 140

Val Phe Val Pro Lys Val Glu Arg Pro Gly Gly Pro Gly Glu Tyr Arg
145                 150                 155                 160

Pro Ile Ser Ile Ala Ser Ile Pro Leu Arg His Phe His Ser Ile Leu
                165                 170                 175

Ala Arg Arg Leu Leu Ala Cys Cys Pro Pro Asp Ala Arg Gln Arg Gly
            180                 185                 190

Phe Ile Cys Ala Asp Gly Thr Leu Glu Asn Ser Ala Val Leu Asp Ala
        195                 200                 205

Val Leu Gly Asp Ser Arg Lys Lys Leu Arg Glu Cys His Val Ala Val
210                 215                 220

Leu Asp Phe Ala Lys Ala Phe Asp Thr Val Ser His Glu Ala Leu Val
225                 230                 235                 240

Glu Leu Leu Arg Leu Arg Gly Met Pro Glu Gln Phe Cys Gly Tyr Ile
                245                 250                 255

Ala His Leu Tyr Asp Thr Ala Ser Thr Thr Leu Ala Val Asn Asn Glu
            260                 265                 270

Met Ser Ser Pro Val Lys Val Gly Arg Gly Val Arg Gln Gly Asp Pro
        275                 280                 285

Leu Ser Pro Ile Leu Phe Asn Val Val Met Asp Leu Ile Leu Ala Ser
290                 295                 300

Leu Pro Glu Arg Val Gly Tyr Arg Leu Glu Met Glu Leu Val Ser Ala
305                 310                 315                 320

Leu Ala Tyr Ala Asp Asp Leu Val Leu Leu Ala Gly Ser Lys Val Gly
                325                 330                 335

Met Gln Glu Ser Ile Ser Ala Val Asp Cys Val Gly Arg Gln Met Gly
            340                 345                 350

Leu Arg Leu Asn Cys Arg Lys Ser Ala Val Leu Ser Met Ile Pro Asp
        355                 360                 365

Gly His Arg Lys Lys His Tyr Leu Thr Arg Thr Phe Asn Ile
370                 375                 380

Gly Gly Lys Pro Leu Arg Gln Val Ser Cys Val Glu Arg Trp Arg Tyr
385                 390                 395                 400

Leu Gly Val Asp Phe Glu Ala Ser Gly Cys Val Thr Leu Glu His Ser
                405                 410                 415
```

-continued

```
Ile Ser Ser Ala Leu Asn Asn Ile Ser Arg Ala Pro Leu Lys Pro Gln
            420                 425                 430

Gln Arg Leu Glu Ile Leu Arg Ala His Leu Ile Pro Arg Phe Gln His
            435                 440                 445

Gly Phe Val Leu Gly Asn Ile Ser Asp Asp Arg Leu Arg Met Leu Asp
            450                 455                 460

Val Gln Ile Arg Lys Ala Val Gly Gln Trp Leu Arg Leu Pro Ala Asp
465                 470                 475                 480

Val Pro Lys Ala Tyr Tyr His Ala Ala Val Gln Asp Gly Gly Leu Ala
                    485                 490                 495

Ile Pro Ser Val Arg Ala Thr Ile Pro Asp Leu Ile Val Arg Arg Phe
                500                 505                 510

Gly Gly Leu Asp Ser Ser Pro Trp Ser Val Arg Ala Ala Lys
            515                 520                 525

Ser Asp Lys Ile Arg Lys Lys Leu Arg Trp Ala Trp Lys Gln Leu Arg
    530                 535                 540

Arg Phe Ser Arg Val Asp Ser Thr Thr Gln Arg Pro Ser Val Arg Leu
545                 550                 555                 560

Phe Trp Arg Glu His Leu His Ala Ser Val Asp Gly Arg Glu Leu Arg
                565                 570                 575

Glu Ser Thr Arg Thr Pro Thr Ser Thr Lys Trp Ile Arg Glu Arg Cys
                580                 585                 590

Ala Gln Ile Thr Gly Arg Asp Phe Val Gln Phe Val His Thr His Ile
                595                 600                 605

Asn Ala Leu Pro Ser Arg Ile Arg Gly Ser Arg Gly Arg Gly Gly
            610                 615                 620

Gly Glu Ser Ser Leu Thr Cys Arg Ala Gly Cys Lys Val Arg Glu Thr
625                 630                 635                 640

Thr Ala His Ile Leu Gln Gln Cys His Arg Thr His Gly Gly Arg Ile
                645                 650                 655

Leu Arg His Asn Lys Ile Val Ser Phe Val Ala Lys Ala Met Glu Glu
            660                 665                 670

Asn Lys Trp Thr Val Glu Leu Glu Pro Arg Leu Arg Thr Ser Val Gly
            675                 680                 685

Leu Arg Lys Pro Ala Ile Ile Ala Ser Arg Asp Gly Val Gly Val Ile
            690                 695                 700

Val Asp Val Gln Val Val Ser Gly Gln Arg Ser Leu Asp Glu Leu His
705                 710                 715                 720

Arg Glu Lys Arg Asn Lys Tyr Gly Asn His Gly Glu Leu Val Glu Leu
                    725                 730                 735

Val Ala Gly Arg Leu Gly Leu Pro Lys Ala Glu Cys Val Arg Ala Thr
                740                 745                 750

Ser Cys Thr Ile Ser Trp Arg Gly Val Trp Ser Leu Thr Ser Tyr Lys
            755                 760                 765

Glu Leu Arg Ser Ile Ile Gly Leu Arg Glu Pro Thr Leu Gln Ile Val
            770                 775                 780

Pro Ile Leu Ala Leu Arg Gly Ser His Met Asn Trp Thr Arg Phe Asn
785                 790                 795                 800

Gln Met Thr Ser Val Met Gly Gly Val Gly
                805                 810

<210> SEQ ID NO 12
<211> LENGTH: 1199
```

```
<212> TYPE: PRT
<213> ORGANISM: Artificial Sequence
<220> FEATURE:
<223> OTHER INFORMATION: synthetic construct

<400> SEQUENCE: 12

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
290                 295                 300

Leu Lys Ser Tyr Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Ala Ala Ala Gln Thr Ala
        355                 360                 365

Ala Ala Ala Ala Met Lys Thr Ser Arg Gln Lys Arg Ala Glu Tyr
370                 375                 380
```

```
Ala Arg Val Gln Glu Leu Tyr Lys Lys Cys Arg Ser Arg Ala Ala Ala
385                 390                 395                 400

Glu Val Ile Asp Gly Ala Cys Gly Gly Val Gly His Ser Leu Glu Glu
            405                 410                 415

Met Glu Thr Tyr Trp Arg Pro Ile Leu Glu Arg Val Ser Asp Ala Pro
        420                 425                 430

Gly Pro Thr Pro Glu Ala Leu His Ala Leu Gly Arg Ala Glu Trp His
        435                 440                 445

Gly Gly Asn Arg Asp Tyr Thr Gln Leu Trp Lys Pro Ile Ser Val Glu
    450                 455                 460

Glu Ile Lys Ala Ser Arg Phe Asp Trp Arg Thr Ser Pro Gly Pro Asp
465                 470                 475                 480

Gly Ile Arg Ser Gly Gln Trp Arg Ala Val Pro Val His Leu Lys Ala
            485                 490                 495

Glu Met Phe Asn Ala Trp Met Ala Arg Gly Glu Ile Pro Glu Ile Leu
        500                 505                 510

Arg Gln Cys Arg Thr Val Phe Val Pro Lys Val Glu Arg Pro Gly Gly
        515                 520                 525

Pro Gly Glu Tyr Arg Pro Ile Leu Ile Ala Ser Ile Pro Leu Arg His
    530                 535                 540

Phe His Ser Ile Leu Ala Arg Arg Leu Leu Ala Cys Cys Pro Pro Asp
545                 550                 555                 560

Ala Arg Gln Arg Gly Phe Ile Cys Ala Asp Gly Thr Leu Glu Asn Ser
            565                 570                 575

Ala Val Leu Asp Ala Val Leu Gly Asp Ser Arg Lys Lys Leu Arg Glu
        580                 585                 590

Cys His Val Ala Val Leu Asp Phe Ala Lys Ala Phe Asp Thr Val Ser
        595                 600                 605

His Glu Ala Leu Val Glu Leu Leu Arg Leu Arg Gly Met Pro Glu Gln
    610                 615                 620

Phe Cys Gly Tyr Ile Ala His Leu Tyr Asp Thr Ala Ser Thr Thr Leu
625                 630                 635                 640

Ala Val Asn Asn Glu Met Ser Ser Pro Val Lys Val Gly Arg Gly Val
            645                 650                 655

Arg Gln Gly Asp Pro Leu Ser Pro Ile Leu Phe Asn Val Val Met Asp
        660                 665                 670

Leu Ile Leu Ala Ser Leu Pro Glu Arg Val Gly Tyr Arg Leu Glu Met
        675                 680                 685

Glu Leu Val Ser Ala Leu Ala Tyr Ala Asp Asp Leu Val Leu Leu Ala
    690                 695                 700

Gly Ser Lys Val Gly Met Gln Glu Ser Ile Ser Ala Val Asp Cys Val
705                 710                 715                 720

Gly Lys Gln Met Gly Leu Arg Leu Asn Cys Arg Lys Ser Ala Val Leu
            725                 730                 735

Ser Met Ile Pro Asp Gly His Arg Lys Lys His Tyr Leu Thr Glu
        740                 745                 750

Arg Thr Phe Asn Ile Gly Gly Lys Pro Leu Arg Gln Val Ser Cys Val
        755                 760                 765

Glu Arg Trp Arg Tyr Leu Gly Val Asp Phe Glu Ala Ser Gly Cys Val
    770                 775                 780

Thr Leu Glu His Ser Ile Ser Ser Ala Leu Asn Asn Ile Ser Arg Ala
785                 790                 795                 800

Pro Leu Lys Pro Gln Gln Arg Leu Glu Ile Leu Arg Ala His Leu Ile
```

```
                805                 810                 815
Pro Arg Phe Gln His Gly Phe Val Leu Gly Asn Ile Ser Asp Asp Arg
                820                 825                 830

Leu Arg Met Leu Asp Val Gln Ile Arg Lys Ala Val Gly Gln Trp Leu
                835                 840                 845

Arg Leu Pro Ala Asp Val Pro Lys Ala Tyr Tyr His Ala Ala Val Gln
                850                 855                 860

Asp Gly Gly Leu Ala Ile Pro Ser Val Arg Ala Thr Ile Pro Asp Leu
865                 870                 875                 880

Ile Val Arg Arg Phe Gly Gly Leu Asp Ser Ser Pro Trp Ser Val Ala
                885                 890                 895

Arg Ala Ala Ala Lys Ser Asp Lys Ile Arg Lys Lys Leu Arg Trp Ala
                900                 905                 910

Trp Lys Gln Leu Arg Arg Phe Ser Arg Val Asp Ser Thr Thr Gln Arg
                915                 920                 925

Pro Ser Val Arg Leu Phe Trp Arg Glu His Leu His Ala Ser Val Asp
                930                 935                 940

Gly Arg Glu Leu Arg Glu Ser Thr Arg Thr Pro Thr Ser Thr Lys Trp
945                 950                 955                 960

Ile Arg Glu Arg Cys Ala Gln Ile Thr Gly Arg Asp Phe Val Gln Phe
                965                 970                 975

Val His Thr His Ile Asn Ala Leu Pro Ser Arg Ile Arg Gly Ser Arg
                980                 985                 990

Gly Arg Arg Gly Gly Gly Glu Ser  Ser Leu Thr Cys Arg  Ala Gly Cys
                995                 1000                1005

Lys Val  Arg Glu Thr Thr Ala  His Ile Leu Gln Gln  Cys His Arg
     1010                1015                1020

Thr His  Gly Gly Arg Ile Leu  Arg His Asn Lys Ile  Val Ser Phe
     1025                1030                1035

Val Ala  Lys Ala Met Glu Glu  Asn Lys Trp Thr Val  Glu Leu Glu
     1040                1045                1050

Pro Arg  Leu Arg Thr Ser Val  Gly Leu Arg Lys Pro  Ala Ile Ile
     1055                1060                1065

Ala Ser  Arg Asp Gly Val Gly  Val Ile Val Asp Val  Gln Val Val
     1070                1075                1080

Ser Gly  Gln Arg Ser Leu Asp  Glu Leu His Arg Glu  Lys Arg Asn
     1085                1090                1095

Lys Tyr  Gly Asn His Gly Glu  Leu Val Glu Leu Val  Ala Gly Arg
     1100                1105                1110

Leu Gly  Leu Pro Lys Ala Glu  Cys Val Arg Ala Thr  Ser Cys Thr
     1115                1120                1125

Ile Ser  Trp Arg Gly Val Trp  Ser Leu Thr Ser Tyr  Lys Glu Leu
     1130                1135                1140

Arg Ser  Ile Ile Gly Leu Arg  Glu Pro Thr Leu Gln  Ile Val Pro
     1145                1150                1155

Ile Leu  Ala Leu Arg Gly Ser  His Met Asn Trp Thr  Arg Phe Asn
     1160                1165                1170

Gln Met  Thr Ser Val Met Gly  Gly Gly Val Gly Glu  Asn Leu Tyr
     1175                1180                1185

Phe Gln  Ser Gly Ser His His  His His His
     1190                1195

<210> SEQ ID NO 13
```

<211> LENGTH: 1433
<212> TYPE: PRT
<213> ORGANISM: Artificial Sequence
<220> FEATURE:
<223> OTHER INFORMATION: synthetic construct

<400> SEQUENCE: 13

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
290                 295                 300

Leu Lys Ser Tyr Glu Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Ala Ala Ala Gln Thr Ala
        355                 360                 365

Ala Ala Ala Ala Met Lys Lys Ser Asn Lys Glu Asn Arg Pro Glu Ala
370                 375                 380

```
Ser Gly Leu Pro Leu Glu Ser Glu Arg Thr Gly Asp Asn Pro Thr Val
385                 390                 395                 400

Arg Gly Ser Ala Gly Ala Asp Pro Val Gly Gln Asp Ala Pro Gly Trp
            405                 410                 415

Thr Cys Gln Phe Cys Glu Arg Thr Phe Ser Thr Asn Arg Gly Leu Gly
                420                 425                 430

Val His Lys Arg Arg Ala His Pro Val Glu Thr Asn Thr Asp Ala Ala
        435                 440                 445

Pro Met Met Val Lys Arg Trp His Gly Glu Glu Ile Asp Leu Leu
    450                 455                 460

Ala Arg Thr Glu Ala Arg Leu Leu Ala Glu Arg Gly Gln Cys Ser Gly
465                 470                 475                 480

Gly Asp Leu Phe Gly Ala Leu Pro Gly Phe Gly Arg Thr Leu Glu Ala
                485                 490                 495

Ile Lys Gly Gln Arg Arg Arg Glu Pro Tyr Arg Ala Leu Val Gln Ala
                500                 505                 510

His Leu Ala Arg Phe Gly Ser Gln Pro Gly Pro Ser Ser Gly Gly Cys
        515                 520                 525

Ser Ala Glu Pro Asp Phe Arg Arg Ala Ser Gly Ala Glu Glu Ala Gly
530                 535                 540

Glu Glu Arg Cys Ala Glu Asp Ala Ala Tyr Asp Pro Ser Ala Val
545                 550                 555                 560

Gly Gln Met Ser Pro Asp Ala Ala Arg Val Leu Ser Glu Leu Leu Glu
                565                 570                 575

Gly Ala Gly Arg Arg Arg Ala Cys Arg Ala Met Arg Pro Lys Thr Ala
                580                 585                 590

Gly Arg Arg Asn Asp Leu His Asp Asp Arg Thr Ala Ser Ala His Lys
                595                 600                 605

Thr Ser Arg Gln Lys Arg Arg Ala Glu Tyr Ala Arg Val Gln Glu Leu
        610                 615                 620

Tyr Lys Lys Cys Arg Ser Arg Ala Ala Ala Glu Val Ile Asp Gly Ala
625                 630                 635                 640

Cys Gly Gly Val Gly His Ser Leu Glu Glu Met Glu Thr Tyr Trp Arg
                645                 650                 655

Pro Ile Leu Glu Arg Val Ser Asp Ala Pro Gly Pro Thr Pro Glu Ala
                660                 665                 670

Leu His Ala Leu Gly Arg Ala Glu Trp His Gly Gly Asn Arg Asp Tyr
        675                 680                 685

Thr Gln Leu Trp Lys Pro Ile Ser Val Glu Glu Ile Lys Ala Ser Arg
        690                 695                 700

Phe Asp Trp Arg Thr Ser Pro Gly Pro Asp Gly Ile Arg Ser Gly Gln
705                 710                 715                 720

Trp Arg Ala Val Pro Val His Leu Lys Ala Glu Met Phe Asn Ala Trp
                725                 730                 735

Met Ala Arg Gly Glu Ile Pro Glu Ile Leu Arg Gln Cys Arg Thr Val
            740                 745                 750

Phe Val Pro Lys Val Glu Arg Pro Gly Gly Pro Gly Glu Tyr Arg Pro
        755                 760                 765

Ile Ser Ile Ala Ser Ile Pro Leu Arg His Phe His Ser Ile Leu Ala
        770                 775                 780

Arg Arg Leu Leu Ala Cys Cys Pro Pro Asp Ala Arg Gln Arg Gly Phe
785                 790                 795                 800
```

```
Ile Cys Ala Asp Gly Thr Leu Glu Asn Ser Ala Val Leu Asp Ala Val
                805                 810                 815

Leu Gly Asp Ser Arg Lys Lys Leu Arg Glu Cys His Val Ala Val Leu
            820                 825                 830

Asp Phe Ala Lys Ala Phe Asp Thr Val Ser His Glu Ala Leu Val Glu
            835                 840                 845

Leu Leu Arg Leu Arg Gly Met Pro Glu Gln Phe Cys Gly Tyr Ile Ala
850                 855                 860

His Leu Tyr Asp Thr Ala Ser Thr Thr Leu Ala Val Asn Asn Glu Met
865                 870                 875                 880

Ser Ser Pro Val Lys Val Gly Arg Gly Val Arg Gln Gly Asp Pro Leu
                885                 890                 895

Ser Pro Ile Leu Phe Asn Val Val Met Asp Leu Ile Leu Ala Ser Leu
            900                 905                 910

Pro Glu Arg Val Gly Tyr Arg Leu Glu Met Glu Leu Val Ser Ala Leu
            915                 920                 925

Ala Tyr Ala Asp Asp Leu Val Leu Leu Ala Gly Ser Lys Val Gly Met
930                 935                 940

Gln Glu Ser Ile Ser Ala Val Asp Cys Val Gly Arg Gln Met Gly Leu
945                 950                 955                 960

Arg Leu Asn Cys Arg Lys Ser Ala Val Leu Ser Met Ile Pro Asp Gly
                965                 970                 975

His Arg Lys Lys His His Tyr Leu Thr Glu Arg Thr Phe Asn Ile Gly
                980                 985                 990

Gly Lys Pro Leu Arg Gln Val Ser Cys Val Glu Arg Trp Arg Tyr Leu
            995                 1000                1005

Gly Val Asp Phe Glu Ala Ser Gly Cys Val Thr Leu Glu His Ser
        1010                1015                1020

Ile Ser Ser Ala Leu Asn Asn Ile Ser Arg Ala Pro Leu Lys Pro
    1025                1030                1035

Gln Gln Arg Leu Glu Ile Leu Arg Ala His Leu Ile Pro Arg Phe
    1040                1045                1050

Gln His Gly Phe Val Leu Gly Asn Ile Ser Asp Asp Arg Leu Arg
    1055                1060                1065

Met Leu Asp Val Gln Ile Arg Lys Ala Val Gly Gln Trp Leu Arg
    1070                1075                1080

Leu Pro Ala Asp Val Pro Lys Ala Tyr Tyr His Ala Ala Val Gln
    1085                1090                1095

Asp Gly Gly Leu Ala Ile Pro Ser Val Arg Ala Thr Ile Pro Asp
    1100                1105                1110

Leu Ile Val Arg Arg Phe Gly Gly Leu Asp Ser Ser Pro Trp Ser
    1115                1120                1125

Val Ala Arg Ala Ala Ala Lys Ser Asp Lys Ile Arg Lys Lys Leu
    1130                1135                1140

Arg Trp Ala Trp Lys Gln Leu Arg Arg Phe Ser Arg Val Asp Ser
    1145                1150                1155

Thr Thr Gln Arg Pro Ser Val Arg Leu Phe Trp Arg Glu His Leu
    1160                1165                1170

His Ala Ser Val Asp Gly Arg Glu Leu Arg Glu Ser Thr Arg Thr
    1175                1180                1185

Pro Thr Ser Thr Lys Trp Ile Arg Glu Arg Cys Ala Gln Ile Thr
    1190                1195                1200

Gly Arg Asp Phe Val Gln Phe Val His Thr His Ile Asn Ala Leu
```

```
                  1205                1210                1215

Pro Ser Arg Ile Arg Gly Ser Arg Gly Arg Arg Gly Gly Gly Glu
        1220                1225                1230

Ser Ser Leu Thr Cys Arg Ala Gly Cys Lys Val Arg Glu Thr Thr
    1235                1240                1245

Ala His Ile Leu Gln Gln Cys His Arg Thr His Gly Gly Arg Ile
1250                1255                1260

Leu Arg His Asn Lys Ile Val Ser Phe Val Ala Lys Ala Met Glu
    1265                1270                1275

Glu Asn Lys Trp Thr Val Glu Leu Glu Pro Arg Leu Arg Thr Ser
        1280                1285                1290

Val Gly Leu Arg Lys Pro Ala Ile Ile Ala Ser Arg Asp Gly Val
    1295                1300                1305

Gly Val Ile Val Asp Val Gln Val Val Ser Gly Gln Arg Ser Leu
    1310                1315                1320

Asp Glu Leu His Arg Glu Lys Arg Asn Lys Tyr Gly Asn His Gly
    1325                1330                1335

Glu Leu Val Glu Leu Val Ala Gly Arg Leu Gly Leu Pro Lys Ala
    1340                1345                1350

Glu Cys Val Arg Ala Thr Ser Cys Thr Ile Ser Trp Arg Gly Val
    1355                1360                1365

Trp Ser Leu Thr Ser Tyr Lys Glu Leu Arg Ser Ile Ile Gly Leu
    1370                1375                1380

Arg Glu Pro Thr Leu Gln Ile Val Pro Ile Leu Ala Leu Arg Gly
    1385                1390                1395

Ser His Met Asn Trp Thr Arg Phe Asn Gln Met Thr Ser Val Met
    1400                1405                1410

Gly Gly Gly Val Gly Glu Asn Leu Tyr Phe Gln Ser Gly Ser His
    1415                1420                1425

His His His His His
    1430

<210> SEQ ID NO 14
<211> LENGTH: 1045
<212> TYPE: PRT
<213> ORGANISM: Artificial Sequence
<220> FEATURE:
<223> OTHER INFORMATION: synthetic construct

<400> SEQUENCE: 14

Lys Lys Ser Asn Lys Glu Asn Arg Pro Glu Ala Ser Gly Leu Pro Leu
1               5                   10                  15

Glu Ser Glu Arg Thr Gly Asp Asn Pro Thr Val Arg Gly Ser Ala Gly
            20                  25                  30

Ala Asp Pro Val Gly Gln Asp Ala Pro Gly Trp Thr Cys Gln Phe Cys
        35                  40                  45

Glu Arg Thr Phe Ser Thr Asn Arg Gly Leu Gly Val His Lys Arg Arg
    50                  55                  60

Ala His Pro Val Glu Thr Asn Thr Asp Ala Ala Pro Met Met Val Lys
65                  70                  75                  80

Arg Arg Trp His Gly Glu Glu Ile Asp Leu Leu Ala Arg Thr Glu Ala
                85                  90                  95

Arg Leu Leu Ala Glu Arg Gly Gln Cys Ser Gly Gly Asp Leu Phe Gly
            100                 105                 110

Ala Leu Pro Gly Phe Gly Arg Thr Leu Glu Ala Ile Lys Gly Gln Arg
```

```
            115                 120                 125
Arg Arg Glu Pro Tyr Arg Ala Leu Val Gln Ala His Leu Ala Arg Phe
130                 135                 140

Gly Ser Gln Pro Gly Pro Ser Ser Gly Gly Cys Ser Ala Glu Pro Asp
145                 150                 155                 160

Phe Arg Arg Ala Ser Gly Ala Glu Glu Ala Gly Glu Glu Arg Cys Ala
                165                 170                 175

Glu Asp Ala Ala Ala Tyr Asp Pro Ser Ala Val Gly Gln Met Ser Pro
            180                 185                 190

Asp Ala Ala Arg Val Leu Ser Glu Leu Leu Glu Gly Ala Gly Arg Arg
            195                 200                 205

Arg Ala Cys Arg Ala Met Arg Pro Lys Thr Ala Gly Arg Arg Asn Asp
210                 215                 220

Leu His Asp Asp Arg Thr Ala Ser Ala His Lys Thr Ser Arg Gln Lys
225                 230                 235                 240

Arg Arg Ala Glu Tyr Ala Arg Val Gln Glu Leu Tyr Lys Lys Cys Arg
                245                 250                 255

Ser Arg Ala Ala Ala Glu Val Ile Asp Gly Ala Cys Gly Gly Val Gly
            260                 265                 270

His Ser Leu Glu Glu Met Glu Thr Tyr Trp Arg Pro Ile Leu Glu Arg
            275                 280                 285

Val Ser Asp Ala Pro Gly Pro Thr Pro Glu Ala Leu His Ala Leu Gly
290                 295                 300

Arg Ala Glu Trp His Gly Gly Asn Arg Asp Tyr Thr Gln Leu Trp Lys
305                 310                 315                 320

Pro Ile Ser Val Glu Glu Ile Lys Ala Ser Arg Phe Asp Trp Arg Thr
                325                 330                 335

Ser Pro Gly Pro Asp Gly Ile Arg Ser Gly Gln Trp Arg Ala Val Pro
            340                 345                 350

Val His Leu Lys Ala Glu Met Phe Asn Ala Trp Met Ala Arg Gly Glu
            355                 360                 365

Ile Pro Glu Ile Leu Arg Gln Cys Arg Thr Val Phe Val Pro Lys Val
370                 375                 380

Glu Arg Pro Gly Gly Pro Gly Glu Tyr Arg Pro Ile Ser Ile Ala Ser
385                 390                 395                 400

Ile Pro Leu Arg His Phe His Ser Ile Leu Ala Arg Arg Leu Leu Ala
                405                 410                 415

Cys Cys Pro Pro Asp Ala Arg Gln Arg Gly Phe Ile Cys Ala Asp Gly
            420                 425                 430

Thr Leu Glu Asn Ser Ala Val Leu Asp Ala Val Leu Gly Asp Ser Arg
            435                 440                 445

Lys Lys Leu Arg Glu Cys His Val Ala Val Leu Asp Phe Ala Lys Ala
450                 455                 460

Phe Asp Thr Val Ser His Glu Ala Leu Val Glu Leu Leu Arg Leu Arg
465                 470                 475                 480

Gly Met Pro Glu Gln Phe Cys Gly Tyr Ile Ala His Leu Tyr Asp Thr
                485                 490                 495

Ala Ser Thr Thr Leu Ala Val Asn Asn Glu Met Ser Ser Pro Val Lys
            500                 505                 510

Val Gly Arg Gly Val Arg Gln Gly Asp Pro Leu Ser Pro Ile Leu Phe
            515                 520                 525

Asn Val Val Met Asp Leu Ile Leu Ala Ser Leu Pro Glu Arg Val Gly
530                 535                 540
```

```
Tyr Arg Leu Glu Met Glu Leu Val Ser Ala Leu Ala Tyr Ala Asp Asp
545                 550                 555                 560

Leu Val Leu Leu Ala Gly Ser Lys Val Gly Met Gln Glu Ser Ile Ser
                565                 570                 575

Ala Val Asp Cys Val Gly Arg Gln Met Gly Leu Arg Leu Asn Cys Arg
            580                 585                 590

Lys Ser Ala Val Leu Ser Met Ile Pro Asp Gly His Arg Lys Lys His
        595                 600                 605

His Tyr Leu Thr Glu Arg Thr Phe Asn Ile Gly Gly Lys Pro Leu Arg
    610                 615                 620

Gln Val Ser Cys Val Glu Arg Trp Arg Tyr Leu Gly Val Asp Phe Glu
625                 630                 635                 640

Ala Ser Gly Cys Val Thr Leu Glu His Ser Ile Ser Ser Ala Leu Asn
                645                 650                 655

Asn Ile Ser Arg Ala Pro Leu Lys Pro Gln Gln Arg Leu Glu Ile Leu
            660                 665                 670

Arg Ala His Leu Ile Pro Arg Phe Gln His Gly Phe Val Leu Gly Asn
        675                 680                 685

Ile Ser Asp Asp Arg Leu Arg Met Leu Asp Val Gln Ile Arg Lys Ala
    690                 695                 700

Val Gly Gln Trp Leu Arg Leu Pro Ala Asp Val Pro Lys Ala Tyr Tyr
705                 710                 715                 720

His Ala Ala Val Gln Asp Gly Gly Leu Ala Ile Pro Ser Val Arg Ala
                725                 730                 735

Thr Ile Pro Asp Leu Ile Val Arg Arg Phe Gly Gly Leu Asp Ser Ser
            740                 745                 750

Pro Trp Ser Val Ala Arg Ala Ala Lys Ser Asp Lys Ile Arg Lys
        755                 760                 765

Lys Leu Arg Trp Ala Trp Lys Gln Leu Arg Arg Phe Ser Arg Val Asp
    770                 775                 780

Ser Thr Thr Gln Arg Pro Ser Val Arg Leu Phe Trp Arg Glu His Leu
785                 790                 795                 800

His Ala Ser Val Asp Gly Arg Glu Leu Arg Glu Ser Thr Arg Thr Pro
                805                 810                 815

Thr Ser Thr Lys Trp Ile Arg Glu Arg Cys Ala Gln Ile Thr Gly Arg
            820                 825                 830

Asp Phe Val Gln Phe Val His Thr His Ile Asn Ala Leu Pro Ser Arg
        835                 840                 845

Ile Arg Gly Ser Arg Gly Arg Gly Gly Glu Ser Ser Leu Thr
    850                 855                 860

Cys Arg Ala Gly Cys Lys Val Arg Glu Thr Thr Ala His Ile Leu Gln
865                 870                 875                 880

Gln Cys His Arg Thr His Gly Arg Ile Leu Arg His Asn Lys Ile
                885                 890                 895

Val Ser Phe Val Ala Lys Ala Met Glu Glu Asn Lys Trp Thr Val Glu
            900                 905                 910

Leu Glu Pro Arg Leu Arg Thr Ser Val Gly Leu Arg Lys Pro Ala Ile
        915                 920                 925

Ile Ala Ser Arg Asp Gly Val Gly Val Ile Asp Val Gln Val Val
    930                 935                 940

Ser Gly Gln Arg Ser Leu Asp Glu Leu His Arg Glu Lys Arg Asn Lys
945                 950                 955                 960
```

-continued

```
Tyr Gly Asn His Gly Glu Leu Val Glu Leu Val Ala Gly Arg Leu Gly
            965                 970                 975
Leu Pro Lys Ala Glu Cys Val Arg Ala Thr Ser Cys Thr Ile Ser Trp
        980                 985                 990
Arg Gly Val Trp Ser Leu Thr Ser  Tyr Lys Glu Leu Arg  Ser Ile Ile
    995                 1000                1005
Gly Leu  Arg Glu Pro Thr Leu  Gln Ile Val Pro Ile  Leu Ala Leu
    1010                1015                1020
Arg Gly  Ser His Met Asn Trp  Thr Arg Phe Asn Gln  Met Thr Ser
    1025                1030                1035
Val Met  Gly Gly Gly Val Gly
    1040                1045

<210> SEQ ID NO 15
<211> LENGTH: 66
<212> TYPE: DNA
<213> ORGANISM: Artificial Sequence
<220> FEATURE:
<223> OTHER INFORMATION: synthetic construct

<400> SEQUENCE: 15
caagcagaag acggcatacg agatgacgag aggtgactgg agttcagacg tgtgctcttc      60
cgatct                                                                66

<210> SEQ ID NO 16
<211> LENGTH: 30
<212> TYPE: RNA
<213> ORGANISM: Artificial Sequence
<220> FEATURE:
<223> OTHER INFORMATION: synthetic construct

<400> SEQUENCE: 16
gaucggaaga gcacacgucu gaacuccagu                                       30

<210> SEQ ID NO 17
<211> LENGTH: 71
<212> TYPE: DNA
<213> ORGANISM: Artificial Sequence
<220> FEATURE:
<223> OTHER INFORMATION: synthetic construct

<400> SEQUENCE: 17
aatgatacgg cgaccaccga gatctacacc gcagacgaca ctctttccct acacgacgct      60
cttccgatct c                                                          71

<210> SEQ ID NO 18
<211> LENGTH: 29
<212> TYPE: RNA
<213> ORGANISM: Artificial Sequence
<220> FEATURE:
<223> OTHER INFORMATION: synthetic construct

<400> SEQUENCE: 18
guguagaucu cgguggucgc cguaucauu                                        29

<210> SEQ ID NO 19
<211> LENGTH: 34
<212> TYPE: DNA
<213> ORGANISM: Artificial Sequence
<220> FEATURE:
<223> OTHER INFORMATION: synthetic construct

<400> SEQUENCE: 19
```

```
gtgactggag ttcagacgtg tgctcttccg atcc                                  34

<210> SEQ ID NO 20
<211> LENGTH: 30
<212> TYPE: RNA
<213> ORGANISM: Artificial Sequence
<220> FEATURE:
<223> OTHER INFORMATION: synthetic construct

<400> SEQUENCE: 20
gaucggaaga gcacacgucu gaacuccagu                                       30

<210> SEQ ID NO 21
<211> LENGTH: 34
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: 5' Phosphorylation
<220> FEATURE:
<221> NAME/KEY: modified_base
<222> LOCATION: (1)..(1)

<400> SEQUENCE: 21
acactctttc cctacacgac gctcttccga tctc                                  34

<210> SEQ ID NO 22
<211> LENGTH: 52
<212> TYPE: DNA
<213> ORGANISM: Artificial Sequence
<220> FEATURE:
<223> OTHER INFORMATION: synthetic construct

<400> SEQUENCE: 22
caagcagaag acggcatacg agattcgatc cagtgactgg agttcagacg tg              52

<210> SEQ ID NO 23
<211> LENGTH: 57
<212> TYPE: DNA
<213> ORGANISM: Artificial Sequence
<220> FEATURE:
<223> OTHER INFORMATION: synthetic construct

<400> SEQUENCE: 23
aatgatacgg cgaccaccga gatctacacc gcagacgaca ctctttccct acacgac         57
```